US012762151B2

(12) United States Patent
Gao et al.

(10) Patent No.: US 12,762,151 B2
(45) Date of Patent: Oct. 13, 2026

(54) VARIANT PATHOGENICITY SCORING AND CLASSIFICATION AND USES THEREOF

(71) Applicant: ILLUMINA, INC., San Diego, CA (US)

(72) Inventors: Hong Gao, Santa Clara, CA (US); Kai-How Farh, Santa Clara, CA (US); Jeremy Francis McRae, San Diego, CA (US)

(73) Assignee: ILLUMINA, INC., San Diego, CA (US)

( * ) Notice: Subject to any disclaimer, the term of this patent is extended or adjusted under 35 U.S.C. 154(b) by 1221 days.

(21) Appl. No.: 17/381,819

(22) Filed: Jul. 21, 2021

(65) Prior Publication Data

US 2022/0027388 A1 Jan. 27, 2022

Related U.S. Application Data

(60) Provisional application No. 63/055,724, filed on Jul. 23, 2020.

(51) Int. Cl.
*G06F 16/28* (2019.01)
*G06N 3/02* (2006.01)
*G16B 20/20* (2019.01)
*G16B 40/20* (2019.01)

(52) U.S. Cl.
CPC ............. *G06F 16/285* (2019.01); *G06N 3/02* (2013.01); *G16B 20/20* (2019.02); *G16B 40/20* (2019.02)

(58) Field of Classification Search
None
See application file for complete search history.

(56) References Cited

U.S. PATENT DOCUMENTS 6,060,033 A 5/2000 Cheng
6,269,934 B2 8/2001 Baker
8,762,072 B2 6/2014 Janevski et al.
9,677,477 B2 6/2017 Oba
10,068,557 B1 9/2018 Engel et al.
10,185,803 B2 1/2019 Frey et al.
10,216,895 B2 2/2019 Liu
10,323,197 B2 6/2019 Scott
10,410,118 B2 9/2019 Xiong et al.
10,423,861 B2 9/2019 Gao et al.
10,489,684 B2 11/2019 Choi et al.
10,540,591 B2 1/2020 Gao et al.
10,552,663 B2 2/2020 Smith et al.
10,558,915 B2 2/2020 Gao et al.
10,770,169 B2 9/2020 Vaske et al.
11,288,576 B2 3/2022 Dutta et al.
11,315,016 B2 4/2022 Sundaram et al.
2002/0055100 A1 5/2002 Kawashima et al.
2003/0187587 A1 10/2003 Swindells et al.
2006/0228728 A1 10/2006 Cox et al.
2007/0166754 A1 7/2007 Mohanlal
2008/0065675 A1 3/2008 Bozich et al.
2011/0004110 A1 1/2011 Shusterman
2011/0294681 A1 12/2011 Hinds et al.
2013/0110407 A1 5/2013 Baccash et al.
2013/0203053 A1 8/2013 Princen et al.
2013/0296175 A1 11/2013 Rafnar et al.
2013/0332081 A1 12/2013 Reese et al.
2014/0129152 A1 5/2014 Beer et al.
2014/0304204 A1 10/2014 Cameron et al.
2015/0324519 A1 11/2015 Liu
2015/0337388 A1 11/2015 Garner et al.
2016/0004814 A1 1/2016 Stamatoyannopoulos
2016/0068915 A1 3/2016 Kennedy et al.
2016/0085910 A1 3/2016 Bruand et al.
2016/0132637 A1 5/2016 Varadan et al.
2016/0140289 A1 5/2016 Gibiansky et al.
2016/0145516 A1 5/2016 Scott
2016/0196479 A1 7/2016 Chertok et al.
2016/0201564 A1 7/2016 Oba
2016/0201565 A1 7/2016 Grose et al.
2016/0275239 A1 9/2016 Devogelaere et al.
2016/0357903 A1 12/2016 Sendure et al.
2016/0364522 A1 12/2016 Frey et al.
2016/0364545 A1 12/2016 Das et al.
2016/0371431 A1 12/2016 Haque et al.

(Continued)

FOREIGN PATENT DOCUMENTS

AU 2021313211 A1 1/2022
CA 2894317 A1 12/2016

(Continued)

OTHER PUBLICATIONS

Van der Velde, K.J., de Boer, E.N., van Diemen, C.C. et al. GAVIN: Gene-Aware Variant INterpretation for medical sequencing. Genome Biol 18, 6 (2017). https://doi.org/10.1186/s13059-016-1141-7 (Year: 2017).*
Sundaram, L., Gao, H., Padigepati, S.R. et al. Predicting the clinical impact of human mutation with deep neural networks. Nat Genet 50, 1161-1170 (2018). https://doi.org/10.1038/s41588-018-0167-z (Year: 2018).*
Kabsch, Wolfgang, et al.; "Pattern Recognition of Hydrogen-Bonded and Geometrical Features", Dictionary of Protein Secondary Structure 1983; pp. 2578-2637.
Brookes, Anthony J.; "The Essence of SNPs", Gene 234 (1999); pp. 177-186.

(Continued)

*Primary Examiner* — G. Steven Vanni
(74) *Attorney, Agent, or Firm* — Fletcher Yoder, P.C.

(57) ABSTRACT

Derivation and use of pathogenicity scores for gene variants are described herein. Applications, uses, and variations of the pathogenicity scoring process include, but are not limited to, the derivation and use of thresholds to characterize a variant as pathogenic or benign, the estimation of selection effects associated with a gene variant, the estimation of genetic disease prevalence using pathogenicity scores, and the recalibration of methods used to assess pathogenicity scores.

21 Claims, 43 Drawing Sheets

(56) References Cited

U.S. PATENT DOCUMENTS

| | | | |
|---|---|---|---|
| 2017/0168866 | A1 | 6/2017 | Kono |
| 2017/0169313 | A1 | 6/2017 | Choi |
| 2017/0199961 | A1 | 7/2017 | Yelensky et al. |
| 2017/0286594 | A1 | 10/2017 | Reid et al. |
| 2018/0032232 | A1 | 2/2018 | Sharma |
| 2018/0107927 | A1 | 4/2018 | Frey |
| 2018/0197067 | A1 | 7/2018 | Mody et al. |
| 2018/0322327 | A1 | 11/2018 | Smith et al. |
| 2018/0330824 | A1 | 11/2018 | Athey et al. |
| 2018/0350451 | A1 | 12/2018 | Ohnemus et al. |
| 2019/0060428 | A1 | 2/2019 | Fritsch |
| 2019/0114511 | A1 | 4/2019 | Gao et al. |
| 2019/0114544 | A1 | 4/2019 | Sundaram et al. |
| 2019/0206521 | A1 | 7/2019 | Walpole et al. |
| 2019/0219599 | A1 | 7/2019 | O'Bryant et al. |
| 2019/0220704 | A1 | 7/2019 | Schultz-Trieglaff et al. |
| 2019/0232592 | A1 | 8/2019 | Tran et al. |
| 2019/0236447 | A1 | 8/2019 | Cohen et al. |
| 2019/0249258 | A1 | 8/2019 | Dietrich |
| 2019/0259499 | A1 | 8/2019 | Hong et al. |
| 2019/0266491 | A1 | 8/2019 | Gao et al. |
| 2019/0266493 | A1 | 8/2019 | Gao et al. |
| 2020/0065675 | A1 | 2/2020 | Sundaram et al. |
| 2020/0097835 | A1 | 3/2020 | Silver et al. |
| 2020/0098465 | A1 | 3/2020 | Jiang et al. |
| 2020/0227137 | A1 | 7/2020 | Sanborn |
| 2020/0243167 | A1 | 7/2020 | Will et al. |
| 2020/0279157 | A1 | 9/2020 | Gao et al. |
| 2020/0370124 | A1 | 11/2020 | Hall et al. |
| 2020/0411199 | A1 | 12/2020 | Shrager et al. |
| 2021/0020293 | A1 | 1/2021 | Richards |
| 2022/0027388 | A1 | 1/2022 | Gao et al. |

FOREIGN PATENT DOCUMENTS

| | | | |
|---|---|---|---|
| CN | 103679185 | A | 3/2014 |
| CN | 105378104 | A | 3/2016 |
| CN | 106575321 | A | 4/2017 |
| CN | 110010201 | A | 7/2019 |
| EP | 4186061 | A1 | 5/2023 |
| JP | 2003527698 | A | 9/2003 |
| JP | 2007052774 | A | 3/2007 |
| JP | 2008216557 | A | 9/2008 |
| JP | 2012032163 | A | 2/2012 |
| JP | 2012504761 | A | 2/2012 |
| JP | 2015501974 | A | 1/2015 |
| JP | 2017111830 | A | 6/2017 |
| JP | 2017520821 | A | 7/2017 |
| JP | 2017151679 | A | 8/2017 |
| JP | 2017168866 | A | 9/2017 |
| JP | 2018504784 | A | 2/2018 |
| JP | 2018527647 | A | 9/2018 |
| JP | 2002505741 | A | 2/2019 |
| RU | 2470998 | C2 | 12/2012 |
| WO | 9705552 | A1 | 2/1997 |
| WO | 9854669 | A1 | 12/1998 |
| WO | 2010/038173 | A1 | 4/2010 |
| WO | 2011139345 | A2 | 11/2011 |
| WO | 2013070634 | A1 | 5/2013 |
| WO | 2015/173222 | A1 | 11/2015 |
| WO | WO 2016201564 | A1 | 12/2015 |
| WO | 2016061396 | A1 | 4/2016 |
| WO | WO 2016145516 | A1 | 9/2016 |
| WO | 2016/201049 | A2 | 12/2016 |
| WO | 2016/209999 | A1 | 12/2016 |
| WO | 2017/172958 | A1 | 10/2017 |
| WO | 2019/079166 | A1 | 4/2019 |
| WO | 2019/079180 | A1 | 4/2019 |
| WO | 2019/079182 | A1 | 4/2019 |
| WO | 2019079198 | A1 | 4/2019 |
| WO | 2019/136284 | A1 | 7/2019 |
| WO | 2019/140402 | A1 | 7/2019 |
| WO | 2022020487 | A1 | 1/2022 |
| WO | 2022020492 | A1 | 1/2022 |

OTHER PUBLICATIONS

Carter, Hannah, et al.; "Cancer Research", The Journal of Cancer Research (1916-1930) | The American Journal of Cancer (1931-1940), Publisherd Online Aug. 4, 2009; pp. 1-9.

Gao, Tingting, et al.; "Identifying translation initiation sites in prokaryotes using support vector machine", Journal of Theoretical Biology 262, 2010; pp. 644-649.

Bi, Yingtao, et al.; "Tree-Based Position Weight Matrix Approach to Model Transcription Factor Biding Site Profiles", PLOS One, Open Access, Sep. 2011, vol. 6 Issue 9; pp. 1-14.

Chang, Chia-Yun, et al.; "Oversampling to Overcome Overfitting: Exploring the Relationship between Data Set Composition, Molecular Descriptors, and Predictive Modeling Methods", Journal of Chemical Information and Modeling 2013, 53; pp. 958-971.

Wei, Qiong, et al.; "The Role of Balanced Training and Testing Data Sets for Binary Classifiers in Bioinformatics", PLOS One, Open Access, Jul. 2013, vol. 8, Issue 7; pp. 1-12.

Wei, Qiong, et al.; "Prediction of phenotyes of missense mutations in human proteins from biological assemblies", National Institutes of Health (NIH), Public Access, Feb. 2013; 81(2); pp. 1-28.

Prakash, V. Jothi, et al.; "A Survey on Semi-Supervised Learning Techniques", International Journal of Computer Trends and Technology (UCTT), vol. 8, No. 1, Feb. 2014; pp. 25-29.

Stanescu, Ana, et al.; Ensemble-based semi-supervised learning approaches for imbalanced splice site datasets, IEEE International Conference on Bioinformatics and Biomedicine 2014; pp. 432-437.

Duggirala, Ravindranath, et al.; "Genome Mapping and Genomics in Animals", Springer Science+Business Media, vol. 5, Library of Congress (control #2015932067), 2015; pp. 1-305.

Ionita-Laza, Iuliana, et al.; Eigen homepage, Columbia University 2015; p. 1.

Korhonen, Janne H., et al.; "Fast motif matching revisited: high-order PWMs, SNPs and idels", Bioinformatics 2017; pp. 514-521.

Reed, Scott E., et al.; "Training Deep Neural Networks on Noisy Labels with Bootstrapping", ICLR 2015; pp. 1-11.

Stanescu, Ana, et al.; "An empirical study of ensemble-based semi-supervised learning approaches for imbalanced splice site datasets", BMC Systems Biology 2015; pp. 1-12.

Vikram, Sharad, et al.; "SSCM: A method to analyze and predict the pathogenicity of sequence variants", bioRxiv, University of California, Jun. 18, 2015; pp. 1-30.

Wong, Sebastien, et al.; "Understanding data augmentation for classification: when to warp?", IEEE 2016; pp. 1-6.

Bahar; "Proteins Change Through Evolutionary Processes", Proteins Evolve, Chapter 7, 2017; pp. 165-166.

Karczewski, Konrad, et al.; "The genome Aggregation Database (gnomAD)", MacArthur Lab, 2017; pp. 1-19.

Martin-Navarro, Antonio, et al.; "Machine learning classifier for identification of damaging missense mutations exclusive to human mitochondrial DNA-encoded polypeptides", BMC Bioinformatics, 2017 18:158; pp. 1-11.

Zhang, Jun, et al.; PSFM-DBT: Identifying DNA-Binding Proteins by Combing Position Specific Frequency Matrix and Distance-Bigram Transformation, International Journal of Molecular Sciences 2017, 18, 1856; pp. 1-16.

Zhang, Yi, et al.; Discerning novel splice junctions derived from RNA-seq alignment: a deep learning approach, BMC Genomics 2018 19:971; pp. 1-13.

Email to Roland Dunbrack from Sikander Mohammed Khan dated Feb. 3, 2019 in re Question about Paper entitled "The Role of Balanced Training and Testing Data Sets for Binary Classifiers in Bioinformatics"; pp. 1-3.

UniProtKB—P04217 (A1BG_Human), https://www.uniprot.org/uniprot/P04217; downloaded Mar. 13, 2019; pp. 1-12.

PCT/US2018-055840, 2019, Article 34; pp. 1-18.

PCT/US2018-055840, 2019, International Search Report; pp. 1-18.

PCT/US2018-055840, 2020, International Preliminary Report on Patentability; pp. 1-26.

PCT/US2018-055878, 2019, International Search Report; pp. 1-20.

PCT/US2018-055878, Aug. 2019, Article 34; pp. 1-36.

PCT/US2018-055878, Dec. 2019, Article 34; pp. 1-31.

(56) References Cited

OTHER PUBLICATIONS

PCT/US2018-055878, Mar. 2019, Article 34; pp. 1-44.
PCT/US2018-055878, 2020, International Preliminary Report on Patentability; pp. 1-38.
PCT/US2018-055881, 2019, International Search Report; pp. 1-17.
PCT/US2018-055881, Dec. 2019, Article 34, pp. 1-41.
PCT/US2018-055881, Oct. 2019, Article 34, pp. 1-25.
PCT/US2018-055881, 2020, International Preliminary Report on Patentability, pp. 1-40.
PCT/US2019/031621, 2019, International Search Report, pp. 1-17.
Srivastava, Rupesh Kumar, et al.; "Highway Networks", The Swiss AI Lab IDSIA, 2015; pp. 1-6.
Bhande, Anup; "What is underfitting and overfitting in machine learning and how to deal with it", Medium, Mar. 11, 2018; 10 pages.
Despois, Julien; "Memorizing is not learning!—6 tricks to prevent overfitting in machine learnin", Mar. 20, 2018, 16 pages.
Dunbrack, Rokand; "Re: Question about your Paper titled The Role of Balanced Training and Testing Data Sets for Binary Classifiers in Bioinformatics", Email message to Sikander Mohammed Khan, Feb. 3, 2019, 3 Pages.
Geeks for Geeks , "Underfitting and Overfitting in Machine Learning", https://www.geeksforgeeks.org/underfitting-and-overfitting-in-machine-learning/, Aug. 26, 2019, 2 pages.
Krizhevsky, Alex, et al., "ImageNet Classification with Deep Convolutional Neural Networks", Advances in neural information processing systems, 2012, 1097-1105.
Leung, Michael K.K., et al.; "Machine Learning in Genomic Medicine: A Review of Computational Problems and Data Sets", IEEE, vol. 104, No. 1, Jan. 2016, 176-197.
Li, Gangmin, et al.; "Classification of Genetic Mutations for Cancer Treatment with Machine Learning Approaches", International Journal of Design, Analysis and Tools for Integrated Circuits and Systems, vol. 7, No. 1, Oct. 1, 2018; pp. 1-5.
Lin, Sheng, et al.; "Computational identification and characterization of primate-specific microRNAs in human genome", Computational Biology and Chemistry 34, Aug. 1, 2010, 232-241.
Smedley, Damian, et al.; "A whole-genome analysis framework for effective identification of pathogenic regulatory variants in mendelian disease", American Journal of Human Genetics 99, Sep. 2016, 595-606.
Douville , et al., "Assessing the Pathogenicity of Insertion and Deletion Variants with the Variant Effect Scoring Tool (VEST-Indel)", Human Mutation, Oct. 7, 2015, 28-35.
Canadian Search Report for Application No. 3,184,399 mailed May 30, 2024, 6 pages.
Application No. 2021-084634; JP Office Action dated May 26, 2022; 15 pgs.
Chen, Hua; "A Computational Approach for Modeling the Allele Frequency Spectrum of Populations with Arbitrarily Varying Size", Genomics Proteomics and Bioinformatics, 2019, vol. 17, No. 6; pp. 635-644.
"dbSNP re2241788", (retrieved on Mar. 13, 2019) from the internet <https://www.ncbi.nlm.nih.gov/snp/re2241788>, 3 pgs. Oct. 2, 2018.
ChIP-seq analysis, BaRC Hot Topics, Bioinformatics and Research Computing, Whitehead Institute, 30 pgs. Feb. 23, 2016.
Bailey, et al., "Practical Guidelines for the Comprehensive Analysis of ChIP-seq Data", PLoS Comput Biol 9(11): e1003326, 25 pgs., Nov. 14, 2013.
Furey, T., "ChIP-seq and beyond: new and improved methodologies to detect and characterize protein-DNA interactions", Nature Reviews Genetics vol. 13, (2012), Oct. 23, 2012, pp. 840-852.
Gandolfi, et al., "A Computational Approach for the Functional Classification of the Epigenome", Epigenetics & Chromatin, 2017, 24 pages.
Gehring, J., et al., "Convolutional Sequence to Sequence Learning", Proceedings of the 34th International Conference on Machine Learning, PMLR 70, 2017, 1243-1252.
Holder, et al., "Machine Learning for Epigenetics and Future Medical Applications", Epigenetics, May 19, 2017, 505-514.
Jaganathan, K., et al., "Predicting Splicing from Primary Sequence with Deep Learning", Cell, Jan. 24, 2016, 535-548 (77 pgs.).
Karczewski, K., et al., "The mutational constraint spectrum quantified from variation in 141,456 humans", Nature, MacMillan Journals Ltd., etc., London, vol. 581, No. 7809;, 2020, 1-24.
Kimura, H., "Histone modifications for human epigenome analysis", Journal of Human Genetics, 58, 2013, 439-445.
Lee, et al., "A method to predict the impact of regulatory variants from DNA sequence", Nature Genetics, Jun. 15, 2015, 955-961.
Quang, et al., "DanQ: a hybrid convolutional and recurrent deep neural network for quantifying the function of DNA sequences", Nucleic Acids Research, Apr. 15, 2016, 6 pages.
Ritchie, et al., "Functional annotation of noncoding sequence variants", Nature Methods, Feb. 2, 2014, 294-296.
Schubach, et al., "Imbalance-Aware Machine Learning for Predicting Rare and Common Disease-Associated Non-Coding Variants", Scientific Reports, Jun. 7, 2017, 12 pages.
Zhou, et al., "Predicting effects of noncoding variants with deep learning-based sequence model", Nature Methods, Oct. 2015, 931-934, (15 pgs.).
Ohta, et al.; "Slightly Deleterious Mutant Sugstitutions in Evolution"; Nature Publishing Group, vol. 248, Nov. 9, 1973; pp. 96-98.
Grantham, R.; "Amino Acid Difference Formula to Help Explain Protein Evolution"; Science, vol. 185, Sep. 6, 1974; pp. 862-864.
Kabsch, Wolfgang, et al.; "Dictionary of Protein Secondary Structure: Pattern Recognition of Hydrogen-Bonded and Geometrical Features", Biopolymers, vol. 22 (1983), pp. 2577-2637.
Li, Wen-Hsiung, et al.; "Nonrandomness of Point Mutation as Reflected in Nucleotide Substitutions in Pseudogenes and its Evolutionary Implications", Journal of Molecular Evolution, 1984, 21:58-71.
Henikoff, Steven, et al.; "Amino Acid Substitution Matrices from Protein Blocks", Proc. Natl. Acad. Sci. USA, vol. 89, Nov. 1992; pp. 10915-10919.
Klein, Jan, et al.; "The Molecular Descent of the Major Histocompatibility Complex", Annu. Rev. Immunol. 1993; 11:269-295.
Takahata, Naoyuki; "Allelic Genealogy and Human Evolution", Mol. Biol. Evol. 10(1):2-22 1993.
Brandon, E.P., et al.; Targeting the mouse genome: a compendium of knockouts (part II), Current Biology 1995, vol. 5, No. 7; pp. 758-765.
Lecun, Yann, et al.; "Gradient-based learning applied to document recognition", Proc. Of the IEEE, Nov. 1998; pp. 1-46.
Ng, Pauline C., et al.; "Predicting Deleterious Amino Acid Substitutions", Genome Research, 2001, 863-874.
Reich, David E., et al.; "On the allelic spectrum of human disease", Trends in Genetics, vol. 17, No. 9, Sep. 2001; pp. 502-510.
Sherry, S.T., et al.; "dbsNP: the NCBI database of genetic variation", Nucleic Acids Research, 2001, vol. 29, No. , pp. 308-311.
Kent, W. James, et al.; "The Human Genome Browser at UCSC", Genome Research, 2002; pp. 996-1006.
Schrago, Carlos G., et al.; "Timing the Origin of New World Monkeys", Mol. Biol. Evol. 20(10):1620-1625, 2003.
Asthana, Saurabh, et al.; "A limited role for balancing selection", Trends in Genetics, vol. 21, No. 1, 2004, pp. 30-32.
Chimpanzee Sequencing and Analysis Consortium; "Initial sequence of the chimpanzee genome and comparison with the human genome", Nature vol. 437, Sep. 2005; pp. 69-87.
Bazykin, Georgii A., et al.; "Extensive parallelism in protein evolution", BioMed Central, Biology Direct 2007, 2:20; pp. 1-13.
Horaitis, Ourania, et al.; "A database of locus-specific databases", Nature Publishing Group, Nature Genetics, vol. 39, No. 4, Apr. 2007; p. 425.
Lieschke, Graham, et al.; "Animal models of human disease: zebrafish swim into view", Nature Publishing Group, Nature Reviews|Genetics vol. 8, May 2007; pp. 353-367.
Rogers, Jeffrey, et al.; "Evolutionary and Biomedical Insights from the Rhesus Macaque Genome", Research Article, Rhesus Macaque Genome Sequencing and Analysis Consortium, Science vol. 316, Apr. 13, 2007; pp. 222-234.
Wang, Dianhui, et al.; "MISCORE: Mismatch-Based Matrix Similarity Scores for DNA Motif Detection", ICONIP 2008, Part I, LNCS 5506; pp. 478-485.

(56) References Cited

OTHER PUBLICATIONS

Chun, Sung, et al.; "Identification of deleterious mutations within three human genomes", Genome Research, 2009; pp. 1-10.
Li, Biao, et al.; "Automated inference of molecular mechanisms of disease from amino acid substitutions", BioInformatics vol. 25, No. 21, 2009; pp. 2744-2750.
Adzhubei, Ivan A., et al.; "A method and server for predicting damaging missense mutations", HHS Public Access Author manuscript, Nat Methods 2010:7(4): 248-249.
Joosten, Robbie P., et al.; "A series of PDB related databases for everyday needs", Nucleic Acids Research, 2011, vol. 39, Database issue, pp. D411-D419.
Schwarz, Jana Marie, et al.; "MutationTaster evaluates disease-causing potential of sequence alterations", Nature Methods, vol. 7, No. 8, Aug. 2010; pp. 575-576.
Bamshad, Michael J., et al.; "Exome sequencing as a tool for Mendelian disease gene discovery", Translational Genetics, Nature Reviews, vol. 12, Nov. 2011; pp. 745-755.
Bell, Callum J., et al.; "Carrier Testing for Severe Childhood Recessive Diseases by Next-Generation Sequencing", Sci Transl Med., Jan. 12, 2011; pp. 1-28.
Liu, Xiaoming, et al.; "dbNSFP: A lightweight Database of Human Nonsynonymous SNPs and Their Functional Predictions", Human Mutation Offical Journalk HGV§ 2011, vol. 32, No. 8; pp. 894-899.
Locke, Devin P., et al.; "Comparative and demographic analysis of orang-utan genomes", Research Letter, 2011 Macmillan Publishers Limited, vol. 469; pp. 529-533.
Reva, Boris, et al.; "Predicing the functional impact of protein mutations application to cancer genomics", Nucleic Acids Research, 2011, vol. 39, No. 17; pp. 1-14.
Choi, Yongwook, et al.; "Predicting the Functional Effect of Amino Acid Substitutions and Indels", PLOS One, Oct. 2012, vol. 7, Issue 10; pp. 1-13.
DeLigt, Joep, et al.; Diagnostic Exome Sequencing in Persons with Severe Intellectual Disability, The New England Journal of Medicine 367;20, Nov. 15, 2012; pp. 1921-1929.
Leffler, Ellen M., et al.; Revisiting an Old Riddle: What Determines Genetic Diversity Levels within Species?, PLOS Biology, Sep. 2012, vol. 10, Issue 9; pp. 1-9.
Iossifov, Ivan, et al.; "De Novo Gene Disruptions in Children on the Autistic Spectrum", Neuron 74, 2012; pp. 285-299.
O'Roak, Brian J., et al.; "Sporadic autism exomes reveal a highly interconnected protein network of de novo mutations", Nature, vol. 485, 2012; pp. 246-252.
Payandeh, Jian, et al.; "The Crystal Structure of a Voltage-gated Sodium Channel", Nature 475, 2012; pp. 1-20.
Rauch, Anita, et al.; "Range of genetic mutations associated with severe non-syndromic sporadic intellectual disability: an exome sequencing study", Lancet 2012, vol. 380; pp. 1674-1682.
Shihab, Hashem A., et al.; "Predicting the Functional, Molecular, and Phenotypic Consequences of Amino Acid Substitutions using Hidden Markov Models", Human Mutation, vol. 34, No. 1, 2012; pp. 57-65.
Allen, Andrew S., et al.; "De novo mutations in the classic epileptic encephalopathies", Nature 501(7466): 217-221, 2013; pp. 1-16.
Carter, Hannah, et al.; "Identifying Mendelian disease genes with the Variant Effect Scoring Tool", BMC Genomics 2013, 14(Suppl 3):53; pp. 1-16.
Leffler, Ellen M., et al.; "Multiple instances of acient balancing selection shared between humans and chimpanzees", Science 2013; 339(6127); pp. 1578-1582.
Nakamura, Kazuyuki, et al.; "Clinical spectrum of SCN2A mutations expanding to Ohtahara syndrome", American Academy of Neurology, 2013; pp. 1-9.
Neale, Benjamin M., et al.; "Patterns and rates of exonic de novo mutations in autism spectrum disorders", Nature; 485(7397): 242-245, 2013, pp. 1-13.
Prado-Martinez, Javier, et al.; "Great ape genetic diversity and population history", Nature, vol. 499, 2013; pp. 471-475.
Sanders, Stephan J., et al.; "De novo mutations revealed by whole exome sequencing are strongly associated with autism", Nature:485(7397): 237-241, 2013; pp. 1-14.
Appenzeller, Silke, et al.; "De Novo Mutations in Synaptic Transmission Genes Including DNM1 Cause Epileptic Encephalopathies", The American Journal of Human Genetics 95, 2014; pp. 360-370.
Famiglietti, Maria Livia, et al.; "Genetic Variations and Diseases in UniProtKB/Swiss-Prot: The Ins and Outs of Expert Manual Curation", Human Mutation Official Journal HGV§, 2014, vol. 35, No. 8; pp. 927-935.
Gilissen, Christian, et al.; "Genome sequencing identifies major causes of severe intellectual disability", Nature 2014; pp. 1-14.
Iossifov, Ivan, et al.; "The contribution of de novo coding mutatios to autism spectrum disorder", Nature vol. 515, 2014; pp. 1-17.
Kircher, Martin, et al.; "A general framework for estimating the relative pathogenicity of human genetic variants", Nature Genetics, vol. 46, No. 3, Mar. 2014; pp. 310-315 (online methods 2 pgs).
Leung, Michael K.K., et al.; "Deep learning of the tissue-related splicing code", Bioinformatics, vol. 30, ISMB 2014; pp. i121-i129.
Macarthur, D.G., et al.; "Guidelines for investigating causality of sequence variants in human disease", Nature, vol. 508, Apr. 2014; pp. 469-476.
Quang, Daniel, et al.; "DANN: a deep learning approach for annotating the pathogenicity of genetic variants", Bioinformatics, 31(5), 2015; pp. 761-763.
Samocha, Kaitlin E., et al.; "A framework for the interpretation of de novo mutation in human disease", Nat. Genet., 2014; 46(9):944-950; pp. 1-19.
Stenson, Peter D., et al.; "The Human Gene Mutation Database: building a comprehensive mutation repository for clinical and molecular genetics, diagnostic testing and personalized genomic medicine", Hum Genet (2014) 133; pp. 1-9.
Szegedy, Christian, et al.; "Going deeper with convolutions", IEEE Conference on Computer Vision and Pattern Recognition in 2014, pp. 1-12.
Zhu, Xiaolin, et al.; "One gene, many neuropsychiatric disorders: lessions from Mendelian diseases", Nature Neuroscience, vol. 17, No. 6, Jun. 2014; pp. 773-781.
Alberts, Bruse, et al.; "How Cells Read the Genome: From DNA to Protein", Molecular Biology of The Cell, Garland Science, 6th Edition, 2015; pp. 1-3.
Alipanahi, Babak, et al.; "Predicting the sequence specificities of DNA- and RNA-binding proteins by deep learning", Nature Biotechnology, vol. 33, No. 8, 2015; pp. 831-839.
Auton, Adam, et al.; "A global reference for human genetic variation", Nature, 2015, vol. 526; pp. 1-20.
DeRubeis, Silvia, et al.; "Synaptic, transcriptional, and chromatin genes disrupted in autism", Nature, 2015; pp. 1-27.
Dong, Chengliang, et al.; "Comparison and integration of deleteriousness prediction methods for nonsynonymous SNVs in whole exome sequencing studies", Human Molecular Genetics, 2015, vol. 24, No. 8; pp. 2125-2137.
Fitzgerald, T.W., et al.; "Large-scale discovery of novel genetic causes of developmental disorders", Nature, vol. 519, Mar. 2015; pp. 1-15.
Gulko, Brad, et al.; "Probabilities of Fitness Consequences for Point Mutations Across the Human Genome", Nat Genet. 2015; 47(3): 276-283; pp. 1-24.
He, Kaiming, et al.; "Deep Residual Learning for Image Recognition", IEEE Conference on Computer Vision and Pattern Recognition (CVPR), 2015; pp. 1-12.
Heffernan, Rhys, et al.; "Improving prediction of secondary structure, local backbone angles, and solvent accessible surfact area of proteins by iterative deep learning", Scientific Reports | 5:11476, 2015; pp. 1-11.
Ioffe, Sergey, et al.; "Batch Normalization: Accelerating Deep Network Training by Reducing Internal Covariate Shift", Proceedings of Machine Learning Research, 2015, vol. 37:448-456; pp. 1-11.
Ionita-Laza, Iuliana, et al.; "A Spectral Approach Integrating Functional Genomic Annotations for Coding and Noncoding Variants", Nat Genet 2016; 48(2); pp. 1-24.

(56) References Cited

OTHER PUBLICATIONS

Landrum, Melissa J., et al.; "ClinVar: public archive of interpretations of clinically relevant variants", Nucleic Acids Research, 2016, vol. 44, Database issue; pp. D862-D868.
Lu, Qiongshi, et al.; "A Statistical Framework to Predict Functional Non-Coding Regions in the Human Genome Through Integrated Analysis of Annotation Data", Scientific Reports, 2015, pp. 1-13.
Park, Yongjin, et al.; "Deep learning for regulatory genomics", Nature Biotechnology, 2015, vol. 33, No. 8; pp. 825-826.
Rehm, Heidi L., et al.; "ClinGen—The Clinical Genome Resource Special Report", The New England Journal of Medicine, 372;23, 2015; pp. 2235-2242.
Richards, Sue, PhD., et al.; "Standards and guidelines for the interpretation of sequence variants: a joint consensus recommendation of the American College of Medical Genetics and Genomics and the Association for Molecular Pathology", Genetics in Medicine, vol. 17, No. 5, May 2015; pp. 405-424.
Shihab, Hashem A., et al.; "An integrative approach to predicting the functional effects of non-coding and coding sequence variation", Bioinformatics, 31(10), 2015; pp. 1536-1543.
Srivastava, Rupesh Kumar, et al.; "Highway Networks" The Swiss AI Lab IDSIA, 2015; p. 1 (incomplete).
Angermueller, Christof, et al.; "Accurate prediction of single-cell DNA methylation states using deep learning", Genome Biology, 2016, doi: https://doi.org/10.1101/055715; pp. 1-33.
Angermueller, Christof, et al.; "Deep learning for computational biology", Molecular Systems Biology 12:878, 2016; pp. 1-16.
DeManuel, Marc, et al.; "Chimpanzee genomic diversity reveals ancient admixture with bonobos", Research Reports, Oct. 2016, vol. 354, Issue 6311, pp. 477-482.
Goodfellow; "Deep Learning Book, Chapter 9, Convolutional Networks", 2016; pp. 1-41.
Harpak, Arbel, et al.; "Mutation Rate Variation is a Primary Determinant of the Distribution of Allele Frequencies in Humans", PLOS Genetics, 2016; pp. 1-22.
He, Kaiming, et al.; "Identity Mappings in Deep Residual Networks", Computer Science, v3, 2016; pp. 1-15.
Ioannidis, Nilah M., et al.; "REVEL: An Ensemble Method for Predicting the Pathogenicity of Rare Missense Variants", The American Journal of Human Genetics 99, Oct. 6, 2016; pp. 877-885.
Jagadeesh, Karthik A., et al.; "M-CAP eliminates a majority of variants of uncertain significance in clinical exomes at high sensitivity", Nature Genetics, vol. 48, No. 12, 2016; pp. 1-8.
Lek, Monkol, et al.; "Analysis of protein-coding genetic variation in 60,706 humans", Nature vol. 536, Aug. 2016; pp. 285-291.
Lelieveld, Stefan, et al.; "Meta-analysis of 2,104 trios provided support for 10 new genes for intellectual disability", Nature Neuroscience 2016 article; pp. 1-6.
Leung, Michael K.K., et al.; "Machine Learning in Genomic Medicine: A Review of Computational Proglems and Data Sets", Proceedings of the IEEE, vol. 104, No. 1, Jan. 2016; pp. 176-197.
Mallick, Sawpan, et al.; "The Simons Genome Diversity Project: 300 genomes from 142 diverse populations", Nature article, vol. 538, Oct. 2016; pp. 1-14.
Min, Seonwoo, et al.; "Deep Learning in Bioinformatics", Briefings in Bioinformatics, vol. 18, Issue 5, Sep. 2017; pp. 851-869.
Piqueras, Laura Cabello; "Autogressive Model Based on a Deep Convolutional Neural Network for Audio Generation", Master of Science thesis 2017; pp. 1-58.
Sittig, Laura J., et al.; "Genetic Background Limits Generalizability of Genotype-Phenotype Relationships", Neuron Report 91, Sep. 2016; pp. 1253-1259.
Smedley, Damian, et al.; "A Whole-Genome Analysis Framework for Effective Identification of Pathogenic Regulatory Variants in Mendelian Disease", The American Journal of Human Genetics , 2016; pp. 595-606.
Tyner, Cath, et al.; "The UCSC Genome Browser database: 2017 update", Nucleic Acids Research, 2017, vol. 45, database issue; pp. D626-D634.
Van Den Oord, Aaron, et al.; "WaveNet: A Generative Model for Raw Audio", arXiv preprint arXiv:1609.03499 (2016); pp. 1-15.
Vissers, Lisenka E.L.M., et al.; "Genetic studies in intellectual disability and related disorders", Applications of Next-Generation Sequencing, Nature Reviews, vol. 17, 2016; p. 9-18.
Wang, Sheng, et al.; "Protein Secondary Structure Prediction Using Deep Convolutional Nural Fields", Nature Scientific Reports, Jan. 2016; pp. 1-11.
Xiong, Hui Y., et al.; "The Human Splicing Code Reveals New Insights into the Genetic Determinants of Disease", Jan. 2016; pp. 1-20.
Yuen, Ryan KC, et al.; "Genome-wide characteristics of de novo mutations in autism", Nature, NPJ Genomic Medicine (2016) 1, 16027; pp. 1-10.
Arik, Sercan Ö., et al.; "Deep Voice: Real-time Neural Text-to-Speech", Neural TTS, Proceedings of the 34$^{th}$ International Conference on Machine Learning, 2017, pp. 1-17.
Estrada, Alejandro, et al.; "Impending extinction crisis of the world's primates: Why primates matter", Science Advances Review, 2017, pp. 1-17.
Fu, Haoyue, et al.; Noncoding Variants Functional Prioritization Methods Based on Predicted Regulatory Factor Binding Sites, Current Genomics, 2017, 18; pp. 322-331.
Gu, Jiuxiang, et al.; "Recent Advances in Convolutional Neural Networks", DOI: 10.1016/j.patcog.2017.10.013; pp. 1-37.
Huang, Gao, et al.; "Densely Connected Convolutional Networks", Computer Vision Foundation, 2017; pp. 1-9.
Jain, Shantanu, et al.; "Recovering True Classifier Performance in Positive-Unlabeled Learning", 31$^{st}$ Conference on Artificial Intelligence (AAAI-17), 2017; pp. 2066-2072.
Karydis, Thrasyvoulos; "Learning hierarchical motif embeddings for protein engineering", Massachusetts Institute of Technology 2017; pp. 1-79.
Lanchantin, Jack, et al.; "Prototype matching networks for large-scale multi-label genomic sequence classification", arXiv preprint arXiv:1710.11238, 2017; pp. 1-15.
Leung, Michael K.K., et al.; "Inference of Human Polyadenylation Code", Department of Electrical and Computer Engineering, University of Toronto, 2017; pp. 1-13.
Libbrecht, Maxwell W., et al.; "Machine learning in genetics and genomics", Nat Rev Genet, 2017; pp. 1-30.
Liu, Xiaoming, et al.; "dbNSFP v3.0: A One-stop database of functional predictions and annotations for human non-synonymous and splice site SNVs", Hum Mutat, 2017, pp. 1-15.
Rehm, Heidi L.; "Evolving health care through personal genomics", Nature Reviews, vol. 18, Apr. 2017; pp. 259-267.
Shen, Huaizong, et al.; Structure of eukaryotic voltage-gated sodium channel at near-atomic resolution, Science, research article, 2017; pp. 1-19.
Torng, Wen, et al.; "3D deep convolutional neural networks for amino acid environment similarity analysis", BMC Bioinformatics, 2017; pp. 1-23.
Whiffin, Nicola, et al.; "Using high-resolution variant frequencies to empower clinical genome interpretation", Genetics in Medicine, vol. 19, No. 10, Oct. 2017; pp. 1151-1158.
Wolterink, Jelmer, et al.; "Dilated Convolutional Neural Networks for Cardiovascular MR Segmentation in Congenital Heart Disease", Computer Science, Computer Vision and Pattern Recognition, 2017; pp. 1-9.
Wu, Jianxin; "Introduction to Convolutional Neural Networks", National Key Lab for Novel Software Technology, Nanjing University, China, 2017; pp. 1-16.
Ahmed, M., et al.; Prevalence and architecture of de novo mutations in developemental disorders, Nature 2017; pp. 1-31.
Chen, Kathleen M., et al.; "Selene: a PyTorch-based deep learning library for sequence-level data", National Library of Medicine, National Center for Biotechnology Information, first posted online 2018; p. 1-15.
Chen, Liang-Chieh, et al.; "DeepLab: Semantic Image Segmentation with Deep Convolution Nets, Atrous Convolution, and Fully Connected CRFs", IEEE Transactions of Pattern Analysis and Machine Intelligence, vol. 40, No. 4, Apr. 2018; p. 834-848.

(56) References Cited

OTHER PUBLICATIONS

Ching, Travers, et al.; "Opportunities and obstacles for deep learning in biology and medicine", J.R. Soc. Interface 15, 2018; pp. 1-47.
Ching, Travers, et al.; "Opportunities and obstacles for deep learning in biology and medicine", J.R. Soc. 2018; https://doi.org/10.1101/142760; pp. 1-123.
Groß, C., et al.; "Predicting variant deleteriousness in non-human species: applying the CADD approach in mouse", BMC Bioinformatics, 2018; pp. 1-10.
Li, Yanjun, et al.; "FoldingZero: Protein Folding from Scratch in Hydrophobic-Polar Model", 32nd Conference on Neural Information Processing Systems, 2018, Montreal, Canada; 1-11.
Rentzsch, Philipp, et al.; "CADD: predicting the deleteriousness of variants throughout the human genome", Nucleic Acids Research, 2018; pp. 1-9.
Sundaram, Laksshman, et al.; "Predicting the clinical impact of human mutation with deep neural networks", Natural Genetics, vol. 50, Aug. 2018; pp. 1-15.
Yue, Tianwei, et al.; "Deep Learning for Genomics: A Concise Overview", Quantitative Biology Cornell University, submitted Feb. 2018; pp. 1-40.
Zou, James, et al.; "A primer on deep learning in genomics", Nature Genetics Perspective, 2018, pp. 1-7.
Karbassi , et al., "A Standardized DNA Variant Scoring System for Pathogenicity Assessments in Mendelian Disorders", Wiley Online Library, Oct. 7, 2015, 8 pages.
Flygare, Steven, et al.; "The VAAST Variant Prioritizer (VVP): ultrafast, easy to use whole genome variant prioritization tool", BMC Bioinformatics, 2018) 19:57; pp. 1-13.
Van der Velde, K. Joeri, et al.; "GAVIN: Gene-Aware Variant Interpretation for Medical Sequencing", Genome Biology, 2017, 18:6; pp. 1-10.
Caron, Barthelemy, et al.; "NCBoost classifies pathogenic non-coding variants in Mendelian diseases through supervised learning on purifying selection signals in humans", Genome Biology, 2019, 20:32; pp. 1-22.
International Search Report and Written Opinion mailed Oct. 25, 2021; Application No. PCT/US2021/0042599; pp. 1-14.
Davydov , et al., "Identifying a high fraction of the human genome to be under selective constraint using GERP++", PLoS Comput Biol., 2010, 13 pages.
Grimm, D. , "The evaluation of tools used to predict the impact of missense variants is hindered by two types of circularity", Human. Mutat, 2015, 513-523.
Worley , et al., "The common marmoset genome provides insight into primate biology and evolution", Nature Genetics, 2014, 850-857.
Gelfman , et al., "Annotating Pathogenic Non-coding Variants in Genic Regions", Nature Communications, 2017, 11 pages.
Yates , et al., "SuSPect: Enhanced Prediction of Single Amino Acid Variant (SAV) Phenotype Using Network Features", Journal of Molecular Biology, Academic Press, 2014, 2692-2701.

* cited by examiner

VARIANT PATHOGENICITY SCORING AND CLASSIFICATION AND USES THEREOF

CROSS-REFERENCE TO RELATED APPLICATION(S)

This application claims priority to U.S. Provisional Patent Application No. 63/055,724, filed on Jul. 23, 2020, which is herein incorporated by reference in its entirety for all purposes.

FIELD OF THE TECHNOLOGY DISCLOSED

The technology disclosed relates to the use of machine learning techniques, which may be referred to as artificial intelligence, implemented on computers and digital data processing systems for the purpose of assessing the pathogenicity of biological sequence variants and deriving other pathogenicity related data using the pathogenicity assessments. These approaches may include or utilize corresponding data processing methods and products for emulation of intelligence (i.e., knowledge based systems, reasoning systems, and knowledge acquisition systems) and/or systems for reasoning with uncertainty (e.g., fuzzy logic systems), adaptive systems, machine learning systems, and artificial neural networks. In particular, the technology disclosed relates to using deep learning-based techniques for training deep convolutional neural networks for pathogenicity assessment as well as the use or refinement of such pathogenicity information.

BACKGROUND

The subject matter discussed in this section should not be assumed to be prior art merely as a result of its mention in this section. Similarly, a problem mentioned in this section or associated with the subject matter provided as background should not be assumed to have been previously recognized in the prior art. The subject matter in this section merely represents different approaches, which in and of themselves can also correspond to implementations of the claimed technology.

Genetic variations can help explain many diseases. Every human being has a unique genetic code and there are many genetic variants within a group of individuals. Many or most genetic variants that are deleterious have been depleted from genomes by natural selection. However, it is still difficult to identify which genetic variations are likely to be of clinical interest.

Further, modeling the properties and functional effects (e.g., pathogenicity) of variants is a challenging task in the field of genomics. Despite the rapid advancement of functional genomic sequencing technologies, interpretation of the functional consequences of variants remains a great challenge due to the complexity of cell type-specific transcription regulation systems.

BRIEF DESCRIPTION

Systems, methods, and articles of manufacture are described for constructing a variant pathogenicity classifier and for using or refining such pathogenicity classifier information. Such implementations may include or utilize non-transitory computer readable storage medium storing instructions executable by a processor to perform actions of the system and methodology described herein. One or more features of an implementation can be combined with the base implementation or other implementations, even if not explicitly listed or described. Further, implementations that are not mutually exclusive are taught to be combinable such that one or more features of an implementation can be combined with other implementations. This disclosure periodically may reminds the user of these options. However, omission from some implementations of recitations that repeat these options should not be taken as limiting the potential combinations taught in the following sections. Instead, these recitations are hereby incorporated forward by reference into each of the following implementations.

This system implementation and other systems disclosed optionally include some or all of the features as discussed herein. The system can also include features described in connection with methods disclosed. In the interest of conciseness, alternative combinations of system features are not individually enumerated. Further, features applicable to systems, methods, and articles of manufacture are not repeated for each statutory class set of base features. The reader will understand how features identified can readily be combined with base features in other statutory classes.

In one aspect of the discussed subject matter, methodologies and systems are described that train a convolutional neural network-based variant pathogenicity classifier, which runs on numerous processors coupled to memory. Alternatively, in other system implementations trained or suitably parameterized statistical models or techniques and/or other machine learning approaches may be employed in addition to or in the alternative of neural network-based classifiers. The system uses benign training examples and pathogenic training examples of protein sequence pairs generated from benign variants and pathogenic variants. The benign variants include common human missense variants and non-human primate missense variants occurring on alternative non-human primate codon sequences that share matching reference codon sequences with humans. The sampled humans may belong to different human subpopulations which may include or be characterized as: African/African American (abbreviated AFR), American (abbreviated AMR), Ashkenazi Jewish (abbreviated ASJ), East Asian (abbreviated EAS), Finnish (abbreviated FIN), Non-Finnish European (abbreviated NFE), South Asian (abbreviated SAS), and Others (abbreviated OTH). The non-human primate missense variants include missense variants from a plurality of non-human primate species, including, but not necessarily limited to: Chimpanzee, Bonobo, Gorilla, B. Orangutan, S. Orangutan, Rhesus, and Marmoset.

As discussed herein, a deep convolutional neural network, running on the numerous processors, may be trained to classify a variant amino acid sequence as benign or pathogenic. Thus, an output of such a deep convolutional neural network may include, but is not limited to, a pathogenicity score or classification for the variant amino acid sequence. As may be appreciated, in certain implementations suitably parameterized statistical models or techniques and/or other machine learning approaches may be employed in addition to or in the alternative of neural network-based approaches.

In certain embodiments discussed herein, the pathogenicity processing and/or scoring operations may include further features or aspects. By way of example, various pathogenicity scoring thresholds may be employed as part of the evaluation or assessment process, such as to assess or score a variant as benign or pathogenic. By way of example, in certain implementations, a suitable percentile of a pathogenicity score per gene for use as a threshold for likely pathogenic variants may be in the range from 51% to 99%, such as, but not limited to, the 51st, 55th, 65th, 70th, 75th, 80th, 85th, 90th, 95th, or 99th percentile. Conversely, a suitable percentile of the pathogenicity score per gene for use as a threshold for likely benign variants may be in the range from 1% to 49%, such as, but not limited to, the 1st, 5th, 10th, 15th, 20th, 25th, 30th, 35th, 40th, or 45th percentile.

In further embodiments, the pathogenicity processing and/or scoring operations may include further features or aspects that allow selection effects to be estimated. In such embodiments, forward time simulation of allele frequencies within a given population, using suitable inputs characterizing mutation rates and/or selection, may be employed to generate an allele frequency spectrum at a gene of interest. Depletion metrics may then be calculated for variants of interest, such as by comparing allele frequency spectra with and without selection, and a corresponding selection-depletion function fitted or characterized. Based on a given pathogenicity score and this selection-depletion function, a selection coefficient can be determined for a given variant based on the pathogenicity score generated for the variant.

In additional aspects, the pathogenicity processing and/or scoring operations may include further features or aspects that allow genetic disease prevalence to be estimated using pathogenicity scores. With respect to calculating a genetic disease prevalence metric for each gene, in a first methodology the trinucleotide context configurations of a set of deleterious variants is initially obtained. For each trinucleotide context in this set, a forward-time simulation assuming certain selection coefficients (e.g. 0.01) is performed to generate the expected allele frequency spectrum (AFS) for that trinucleotide context. Summing up AFS across the trinucleotides weighted by frequencies of trinucleotides in a gene produces the expected AFS for the gene. The genetic disease prevalence metric in accordance with this approach may be defined as the expected cumulative allele frequencies of variants having pathogenicity scores exceeding the threshold for that gene.

In a further aspect, the pathogenicity processing and/or scoring operations may include features or methodology to recalibrate the pathogenicity scoring. With respect to such as recalibration, in one example embodiment, a recalibration approach may focus on the percentiles of pathogenicity scores of variants, as these may be more robust and less affected by selection pressure exerted on the whole genes. In accordance with one implementation, a survival probability for each percentile of pathogenicity scores is calculated, which constitutes a survival probability correction factor that implies that the higher the percentile of pathogenicity scores, the less chance the variant survives purifying selection. The survival probability correction factor may be employed to perform a recalibration so as to help mitigate the effects of noise on the estimation of selection coefficients in missense variants.

The preceding description is presented to enable the making and use of the technology disclosed. Various modifications to the disclosed implementations will be apparent, and the general principles defined herein may be applied to other implementations and applications without departing from the spirit and scope of the technology disclosed. Thus, the technology disclosed is not intended to be limited to the implementations shown, but is to be accorded the widest scope consistent with the principles and features disclosed herein. The scope of the technology disclosed is defined by the appended claims.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
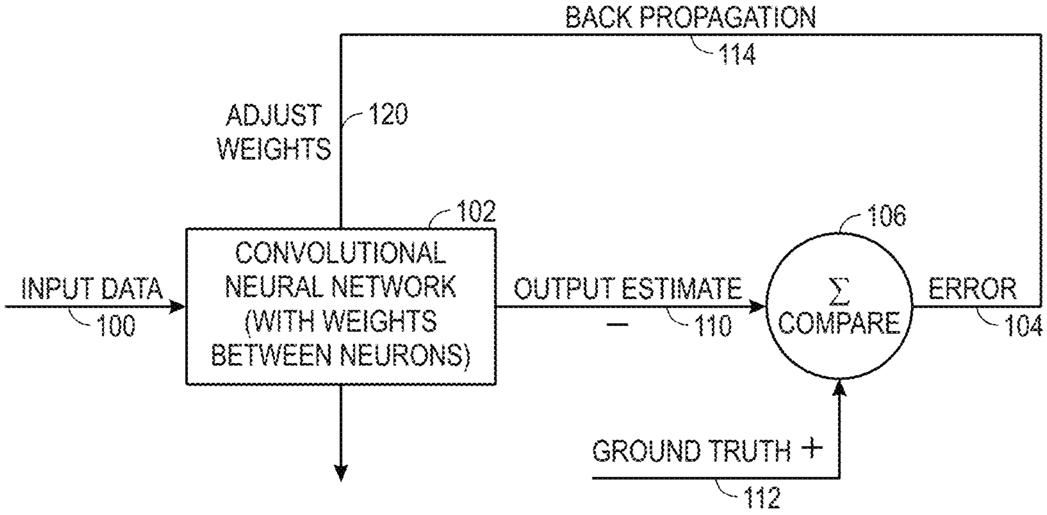
FIG. 1 depicts a block diagram of aspects of training a convolutional neural network in accordance with one implementation of the technology disclosed.

The following discussion is presented to enable any person skilled in the art to make and use the technology disclosed, and is provided in the context of a particular application and its requirements. Various modifications to the disclosed implementations will be readily apparent to those skilled in the art, and the general principles defined herein may be applied to other implementations and applications without departing from the spirit and scope of the technology disclosed. Thus, the technology disclosed is not intended to be limited to the implementations shown, but is to be accorded the widest scope consistent with the principles and features disclosed herein.

I. Introduction

The following discussion includes aspects related to the training and use of neural networks, including convolutional neural networks, which may be used to implement certain of the analytics discussed below, such as the generation of variant pathogenicity scores or classifications and the derivation of useful clinical analytics or metrics based on such pathogenicity scores or classifications. With this in mind, certain aspects and features of such neural networks may be mentioned or referenced in describing the present techniques. To streamline discussion, a baseline knowledge of such neural networks is presumed in describing the present techniques. However, additional information and description of relevant neural network concepts is provided toward the end of the description for those wanting additional explanation of the relevant neural network concepts. Further, it should also be appreciated that, though neural networks are primarily discussed herein to provide a useful example and to facilitate explanation, other implementations may be employed in place of or in addition to neural network approaches, including but not limited to trained or suitably parameterized statistical models or techniques and/or other machine learning approaches.

In particular, the following discussion may utilize certain concepts related to neural networks (e.g., convolutional neural networks) in implementations used to analyze certain genomic data of interest. With that in mind, certain aspects of the underlying biological and genetic problems of interest are outlined here to provide a useful context to the problems being addressed herein, for which the neural network techniques discussed herein may be utilized.

Genetic variations can help explain many diseases. Every human being has a unique genetic code and there are many genetic variants within a group of individuals. Many or most genetic variants that are deleterious have been depleted from genomes by natural selection. However, it is still desirable to identify which genetics variations are likely to be pathogenic or deleterious. In particular, such knowledge may help researchers focus on the likely pathogenic genetic variants and accelerate the pace of diagnosis and cure of many diseases.

Modeling the properties and functional effects (e.g., pathogenicity) of variants is an important but challenging task in the field of genomics. Despite the rapid advancement of functional genomic sequencing technologies, interpretation of the functional consequences of variants remains a great challenge due to the complexity of cell type-specific transcription regulation systems. Therefore, a powerful computational model for predicting the pathogenicity of variants can have substantial benefits for both basic science and translational research.

Further, advances in biochemical technologies over the past decades have given rise to next generation sequencing (NGS) platforms that quickly produce genomic data at much lower costs than ever before, resulting in ever increasing amounts of genomic data being generated. Such overwhelmingly large volumes of sequenced DNA remain difficult to annotate. Supervised machine learning algorithms typically perform well when large amounts of labeled data are available. However, in bioinformatics and many other data-rich disciplines, the process of labeling instances is costly. Conversely, unlabeled instances are inexpensive and readily available. For a scenario in which the amount of labeled data is relatively small and the amount of unlabeled data is substantially larger, semi-supervised learning represents a cost-effective alternative to manual labeling. This therefore presents an opportunity to use semi-supervised algorithms to construct deep learning-based pathogenicity classifiers that accurately predict pathogenicity of variants. Databases of pathogenic variants that are free from human ascertainment bias may result.

Regarding machine-learning based pathogenicity classifiers, deep neural networks are a type of artificial neural networks that use multiple nonlinear and complex transforming layers to successively model high-level features. Deep neural networks provide feedback via backpropagation which carries the difference between observed and predicted output to adjust parameters. Deep neural networks have evolved with the availability of large training datasets, the power of parallel and distributed computing, and sophisticated training algorithms.

Convolutional neural networks (CNNs) and recurrent neural networks (RNNs) are components of deep neural networks. Convolutional neural networks may have an architecture that comprises convolution layers, nonlinear layers, and pooling layers. Recurrent neural networks are designed to utilize sequential information of input data with cyclic connections among building blocks like perceptrons, long short-term memory units, and gated recurrent units. In addition, many other emergent deep neural networks have been proposed for limited contexts, such as deep spatio-temporal neural networks, multi-dimensional recurrent neural networks, and convolutional auto-encoders.

Given that sequence data are multi- and high-dimensional, deep neural networks have promise for bioinformatics research because of their broad applicability and enhanced prediction power. Convolutional neural networks have been adapted to solve sequence-based problems in genomics such as motif discovery, pathogenic variant identification, and gene expression inference. Convolutional neural networks use a weight-sharing strategy that is useful for studying DNA because it can capture sequence motifs, which are short, recurring local patterns in DNA that are presumed to have significant biological functions. A hallmark of convolutional neural networks is the use of convolution filters. Unlike traditional classification approaches that are based on elaborately-designed and manually-crafted features, convolution filters perform adaptive learning of features, analogous to a process of mapping raw input data to the informative representation of knowledge. In this sense, the convolution filters serve as a series of motif scanners, since a set of such filters is capable of recognizing relevant patterns in the input and updating themselves during the training procedure. Recurrent neural networks can capture long-range dependencies in sequential data of varying lengths, such as protein or DNA sequences.

Training deep neural network, as depicted schematically in FIG. 1, involves optimizing the weight parameters in each layer, which gradually combine simpler features into complex features so that the most suitable hierarchical representations can be learned from data. A single cycle of the optimization process is organized as follows. First, given a training dataset (e.g., input data 100 in this example), a forward pass sequentially computes the output in each layer and propagates the function signals forward through the neural network 102. In the final output layer, an objective loss function (comparison step 106) measures error 104 between the inferenced outputs 110 and the given labels 112. To minimize the training error, a backward pass uses the chain rule to backpropagate (step 114) error signals and compute gradients with respect to all weights throughout the neural network 102. Finally, the weight parameters are updated (step 120) using optimization algorithms based on stochastic gradient descent or other suitable approaches. Whereas batch gradient descent performs parameter updates for each complete dataset, stochastic gradient descent provides stochastic approximations by performing the updates for each small set of data examples. Several optimization algorithms stem from stochastic gradient descent. For example, the Adagrad and Adam training algorithms perform stochastic gradient descent while adaptively modifying learning rates based on update frequency and moments of the gradients for each parameter, respectively.

Another element in the training of deep neural networks is regularization, which refers to strategies intended to avoid overfitting and thus achieve good generalization performance. For example, weight decay adds a penalty term to the objective loss function so that weight parameters converge to smaller absolute values. Dropout randomly removes hidden units from neural networks during training and can be considered an ensemble of possible subnetworks. Furthermore, batch normalization provides a new regularization method through normalization of scalar features for each activation within a mini-batch and learning each mean and variance as parameters.

With the preceding high-level overview in mind with respect to the presently described techniques, the presently described techniques differ from prior pathogenicity classification models, which employ a large number of human-engineered features and meta-classifiers. In contrast, in certain embodiments of the techniques described herein a simple deep learning residual network may be employed which takes as input only the amino acid sequence flanking a variant of interest and the orthologous sequence alignments in other species. In certain implementations, to provide the network with information about protein structure two separate networks may be trained to learn, respectively, secondary structure and solvent accessibility from sequence alone. These may be incorporated as sub-networks in the larger deep learning network to predict effects on protein structure. Using sequence as a starting point avoids potential biases in protein structure and functional domain annotation, which may be incompletely ascertained or inconsistently applied.

The accuracy of the deep learning classifier scales with the size of the training dataset, and variation data from each of six primate species independently contributes to boosting the accuracy of the classifier. The large number and diversity of extant non-human primate species, along with evidence showing that the selective pressures on protein-altering variants are largely concordant within the primate lineage, suggests systematic primate population sequencing as an effective strategy to classify the millions of human variants of unknown significance that currently limit clinical genome interpretation.

Further, common primate variation provides a clean validation dataset for evaluating existing methods that is completely independent of previously used training data, which has been hard to evaluate objectively because of the proliferation of meta-classifiers. The performance of the present model described herein was evaluated, along with four other popular classification algorithms (Sift, Polyphen2, CADD, M-CAP), using 10,000 held-out primate common variants. Because roughly 50% of all human missense variants would be removed by natural selection at common allele frequencies, the 50th-percentile score was calculated for each classifier on a set of randomly picked missense variants that were matched to the 10,000 held-out primate common variants by mutational rate, and that threshold was used to evaluate the held-out primate common variants. The accuracy of the presently disclosed deep learning model was significantly better than the other classifiers on this independent validation dataset, using either deep learning networks that were trained only on human common variants or using both human common variants and primate variants.

With the preceding in mind, and by way of summary, the methodology described herein differs from the existing methods for predicting pathogenicity of variants in various ways. First, the presently described approach adopts a novel architecture of semi-supervised deep convolutional neural networks. Second, reliable benign variants are obtained from human common variants (e.g., from gnomAD) and primate variants, while the highly confident pathogenic training set is generated through iterative balanced sampling and training, to avoid circular training and testing of models using the identical human curated variant databases. Third, deep learning models for secondary structure and solvent accessibility are integrated into the architecture of the pathogenicity model. The information obtained from the structure and solvent models are not limited to label prediction for specific amino acid residues. Rather, the readout layer is removed from the structure and solvent models, and the pre-trained models are merged with the pathogenicity model. While training the pathogenicity model, the structure and solvent pre-trained layers also backpropagate to minimize the error. This helps the pre-trained structure and solvent model to focus on the pathogenicity prediction problem.

As also discussed herein, outputs (e.g., pathogenicity scores and/or classifications) of a model trained and used as described herein, may be used to generate additional data or diagnoses of value, such as estimation of selection effects against a range of clinically significant variants and estimation of genetic disease prevalence. Other relevant concepts, such as recalibration of the model outputs and the generation and use of threshold values for characterizing pathogenic and benign variants are also described.

II. Terminology/Definitions

As used herein:

A base refers to a nucleotide base or nucleotide, A (adenine), C (cytosine), T (thymine), or G (guanine).

The terms “protein” and “translated sequence” may be used interchangeably.

The terms “codon” and “base triplet” may be used interchangeably.

The terms “amino acid” and “translated unit” may be used interchangeably.

The phrases “variant pathogenicity classifier”, “convolutional neural network-based classifier for variant classification”, and “deep convolutional neural network-based classifier for variant classification” may be used interchangeably.

III. Pathogenicity Classification Neural Network

A. Training and Inputs

Turning to example implementations, a deep learning network is described herein that may be used for variant pathogenicity classification (e.g., pathogenic or benign) and/or generation of a quantitative metric (e.g., a pathogenicity score) that numerically characterizes pathogenicity or the lack of pathogenicity. In one context of training a classifier using only variants with benign labels, the prediction problem was framed as whether a given mutation is likely to be observed as a common variant in the population. Several factors influence the probability of observing a variant at high allele frequencies, though deleteriousness is the primary focus of the present discussion and description. Other factors include, but are not limited to: mutation rate, technical artifacts such as sequencing coverage, and factors impacting neutral genetic drift (such as gene conversion).

With respect to training the deep learning network, the importance of variant classification for clinical applications has inspired numerous attempts to use supervised machine learning to address the problem, but these efforts have been hindered by the lack of an adequately sized truth dataset containing confidently labeled benign and pathogenic variants for training.

Existing databases of human expert curated variants do not represent the entire genome, with ~50% of the variants in the ClinVar database coming from only 200 genes (~1% of human protein-coding genes). Moreover, systematic studies identify that many human expert annotations have questionable supporting evidence, underscoring the difficulty of interpreting rare variants that may be observed in only a single patient. Although human expert interpretation has become increasingly rigorous, classification guidelines are largely formulated around consensus practices and are at risk of reinforcing existing tendencies. To reduce human interpretation biases, recent classifiers have been trained on common human polymorphisms or fixed human-chimpanzee substitutions, but these classifiers also use as their input the prediction scores of earlier classifiers that were trained on human curated databases. Objective benchmarking of the performance of these various methods has been elusive in the absence of an independent, bias-free truth dataset.

To address this issue, the presently described techniques leverage variation from non-human primates (e.g., chimpanzee, bonobo, gorilla, orangutan, rhesus, and marmoset) that contributes over 300,000 unique missense variants that are non-overlapping with common human variation and largely represent common variants of benign consequence that have been through the sieve of purifying selection. This greatly enlarges the training dataset available for machine learning approaches. On average, each primate species contributes more variants than the whole of the ClinVar database (~42,000 missense variants as of November 2017, after excluding variants of uncertain significance and those with conflicting annotations). Additionally, this content is free from biases in human interpretation.

With respect to generating a benign training dataset for use in accordance with the present techniques, one such dataset was constructed of largely common benign missense variants from human and non-human primates for machine learning. The dataset comprised common human variants (>0.1% allele frequency; 83,546 variants), and variants from chimpanzee, bonobo, gorilla, and orangutan, rhesus, and marmoset (301,690 unique primate variants).

Using one such dataset that comprised common human variants (allele frequency (AF)>0.1%) and primate variation, a deep residual network, referred to herein as PrimateAI or pAI, was trained. The network was trained to receive as an input the amino acid sequence flanking the variant of interest and the orthologous sequence alignments in other species. Unlike existing classifiers that employ human-engineered features, the presently described deep learning network was trained to extract features directly from the primary sequence. In certain implementations, to incorporate information about protein structure, and as described in greater detail below, separate networks were trained to predict the secondary structure and the solvent accessibility from the sequence alone, and these were included as subnetworks in the full model. Given the limited number of human proteins that have been successfully crystallized, inferring structure from the primary sequence has the advantage of avoiding biases due to incomplete protein structure and functional domain annotation. The total depth of one implementation of the network, with protein structure included, was 36 layers of convolutions, comprising roughly 400,000 trainable parameters.

B. Protein Structure $2^{nd}$ Structure and Solvent Accessibility Sub-Networks In one example of an implementation, the deep learning network for pathogenicity prediction contains 36 total convolutional layers, including 19 convolutional layers for secondary structure and solvent accessibility prediction sub-networks, and 17 for the main pathogenicity prediction network which takes as input the results of the secondary structure and solvent accessibility sub-networks. In particular, because the crystal structures of most human proteins are unknown, the secondary structure network and the solvent accessibility prediction network were trained to enable the network to learn protein structure from primary sequence.

The secondary structure and solvent accessibility prediction networks in one such implementation have identical architecture and input data, but differ on the prediction states. For example, in one such implementation, the input to the secondary structure and solvent accessibility networks is an amino acid position frequency matrix (PFM) of suitable dimensions (e.g., a 51 length×20 amino acid PFM) encoding conservation information from the multiple sequence alignment of human with 99 other vertebrates.

Figure 2:
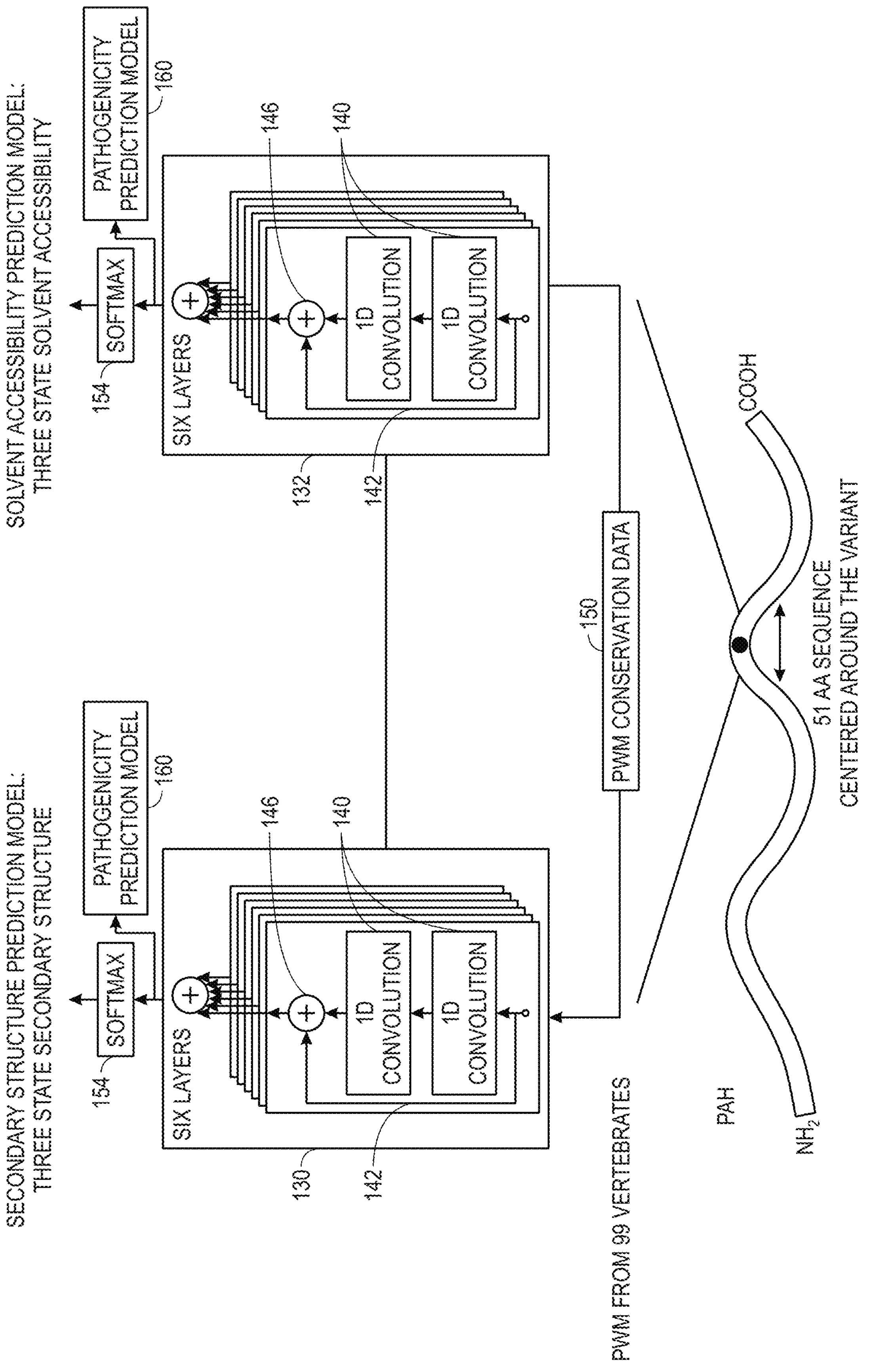
FIG. 2 illustrates a deep learning network architecture used for predicting secondary structure and solvent accessibility of proteins, in accordance with one implementation of the technology disclosed.

In one embodiment, and with reference to FIG. 2, the deep learning network for pathogenicity prediction and the deep learning networks for predicting secondary structure and solvent accessibility adopted the architecture of residual blocks 140. The residual blocks 140 comprise repeating units of convolution, interspersed with skip connections 142 that allow information from earlier layers to skip over residual blocks 140. In each residual block 140, the input layer is first batch normalized, followed by an activation layer using rectified linear units (ReLU). The activation is then passed through a 1D convolution layer. This intermediate output from the 1D convolution layer is again batch normalized and ReLU activated, followed by another 1D convolution layer. At the end of the second 1D convolution, its output was summed (step 146) with the original input into the residual block, which acts as a skip connection 142 by allowing the original input information to bypass the residual block 140. In such an architecture, which may be referred to as a deep residual learning network, the input is preserved in its original state and the residual connections are kept free of nonlinear activations from the model, allowing effective training of deeper networks. The detailed architecture in the context of both the secondary structure network 130 and solvent accessibility network 132 is provided in FIG. 2 and Tables 1 and 2 (discussed below), where PWM conservation data 150 is illustrated as an initial input. In the depicted example, the input 150 to the model may be a position-weighted matrix (PWM) using conservation generated by the RaptorX software (for training on Protein Data Bank sequences) or the 99-vertebrate alignments (for training and inference on human protein sequences).

Following the residual blocks 140, the softmax layer 154 computes probabilities of the three states for each amino acid, among which the largest softmax probability determines the state of the amino acid. The model in one such implementation is trained with accumulated categorical cross entropy loss function for the whole protein sequence using the ADAM optimizer. In one implementation, which is illustrated, once the networks were pre-trained on secondary structure and solvent accessibility, instead of directly taking the output of the networks as inputs for the pathogenicity prediction network 160, the layer before the softmax layer 154 was instead taken so that more information would pass through to the pathogenicity prediction network 160. In one example, the output of the layer before the softmax layer 154 is an amino acid sequence of suitable length (e.g., 51 amino acids in length) and becomes the input for the deep learning network for pathogenicity classification.

With the preceding in mind, the secondary structure network is trained to predict a 3-state secondary structure: (1) alpha helix (H), (2) beta sheet (B), or (3) coils (C). The solvent accessibility network is trained to predict a 3-state solvent accessibility: (1) buried (B), (2) intermediate (I), or (3) exposed (E). As noted above, both networks only take primary sequence as their inputs 150, and were trained using labels from known crystal structures in the Protein DataBank. Each model models predict one respective state for each amino acid residue.

With the preceding in mind, and by way of further illustration of an example implementation, for each amino acid position in the input dataset 150, a window from the position frequency matrix was taken corresponding to the flanking amino acids (e.g., flanking 51 amino acids) and this was used to predict the label for either secondary structure or solvent accessibility for the amino acid at the center of the length amino acid sequence. The labels for secondary structure and relative solvent accessibility were directly obtained from the known 3D crystal structure of the protein using the DSSP software and did not require prediction from primary sequence. To incorporate the secondary structure network and solvent accessibility networks as part of the pathogenicity prediction network 160, position frequency matrices were computed from the human-based 99 vertebrate multiple sequence alignments. Although the conservation matrices generated from these two methods are generally similar, backpropagation was enabled through the secondary structure and solvent accessibility models during training for pathogenicity prediction to allow fine-tuning of the parameter weights.

By way of example, Table 1 shows example model architecture details for a 3-state secondary structure prediction deep learning (DL) model. The shape specifies the shape of the output tensor at each layer of the model and the activation is the activation given to the neurons of the layer. Inputs to the model were the position-specific frequency matrices of suitable dimensions (e.g., 51 amino acid length, 20 depth) for the flanking amino acid sequence around the variant.

Similarly, the model architecture illustrated in Table 2 shows example model architecture details for the 3-state solvent accessibility prediction deep learning model, which as noted herein may be identical in architecture to the secondary structure prediction DL model. The shape specifies the shape of the output tensor at each layer of the model and the activation is the activation given to the neurons of the layer. Inputs to the model were the position-specific frequency matrices of suitable dimensions (e.g., 51 amino acid length, 20 depth) for the flanking amino acid sequence around the variant.

The best testing accuracy for the 3-state secondary structure prediction model was 80.32%, similar to the state-of-the-art accuracy predicted by DeepCNF model on a similar training dataset. The best testing accuracy for the 3-state solvent accessibility prediction model was 64.83%, similar to the current best accuracy predicted by RaptorX on a similar training dataset.

Example Implementation—Model Architecture and Training

With reference to the Tables 1 and 2 (reproduced below) and FIG. 2, and by way of providing an example of an implementation, two end-to-end deep convolutional neural network models were trained to predict the 3-state secondary structure and 3-state solvent accessibility of proteins, respectively. The two models had similar configurations, including two input channels, one for protein sequences and the other for protein conservation profiles. Each input channel has the dimension L×20, where L denotes the length of a protein.

Each of the input channel was passed through a 1D convolution layer (layer 1a and 1b) with 40 kernels and linear activations. This layer was used to upsample the input dimensions from 20 to 40. All of the other layers throughout the model used 40 kernels. The two layers (1a and 1b) activations were merged together by summing the values across each of the 40 dimensions (i.e., merge mode='sum'). The output of the merge node was passed through a single layer of 1D convolution (layer 2) followed by linear activation.

The activations from layer 2 was passed through a series of 9 residual blocks (layers 3 to 11). The activations of layer 3 was fed to layer 4 and layer 4's activation was fed to layer 5, and so on. There were also skip connections that directly summed the output of every 3rd residual block (layers 5, 8, and 11). The merged activations were then fed to two 1D convolutions (layers 12 and 13) with ReLU activations. The activations from layer 13 were given to the softmax readout layer. The softmax computed the probabilities of the three-class outputs for the given input.

As a further note, in one implementation of the secondary structure model, the 1D convolutions had an atrous rate of 1. In an implementation of the solvent accessibility model, the last 3 residual blocks (layers 9, 10 and 11) had an atrous rate of 2 to increase the coverage of the kernels. With respect to these aspects, an atrous/dilated convolution is a convolution where the kernel is applied over an area larger than its length by skipping input values with a certain step, also called atrous convolution rate or dilation factor. Atrous/dilated convolutions add spacing between the elements of a convolution filter/kernel so that neighboring input entries (e.g., nucleotides, amino acids) at larger intervals are considered when a convolution operation is performed. This enables incorporation of long-range contextual dependencies in the input. The atrous convolutions conserve partial convolution calculations for reuse as adjacent nucleotides are processed. Atrous/dilated convolutions allow for large receptive fields with few trainable parameters. The secondary structure of a protein is strongly dependent on the interactions of amino acids in close proximity. Thus models with higher kernel coverage improved the performance slightly. Conversely, solvent accessibility is affected by the long-range interactions between amino acids. Therefore, for the model with high coverage of kernels using atrous convolutions, its accuracy was more than 2% higher than that of the short-coverage models.

TABLE 1

An example of a 3-state secondary structure prediction model

| Layer | Type | Number of Kernels, Window size | Shape | Atrous rate | Activation |
|---|---|---|---|---|---|
| Input Sequence (layer 1a) | Convolution 1D | 40, 1 | (L, 40) | 1 | Linear |
| Input PSSM (layer 1b) | Convolution 1D | 40, 1 | (L, 40) | 1 | Linear |
| Merging Sequence + PSSM | Merge (mode = Concatenate) | — | (L, 80) | — | — |
| Layer 2 | Convolution 1D | 40, 5 | (L, 40) | 1 | Linear |
| Layer 3 | Convolution 1D | 40, 5 | (L, 40) | 1 | ReLU |
| Layer 4 | Convolution 1D | 40, 5 | (L, 40) | 1 | ReLU |
| Layer 5 | Convolution 1D | 40, 5 | (L, 40) | 1 | ReLU |
| Layer 6 | Convolution 1D | 40, 5 | (L, 40) | 1 | ReLU |
| Layer 7 | Convolution 1D | 40, 5 | (L, 40) | 1 | ReLU |
| Layer 8 | Convolution 1D | 40, 5 | (L, 40) | 1 | ReLU |
| Layer 9 | Convolution 1D | 40, 5 | (L, 40) | 1 | ReLU |
| Layer 10 | Convolution 1D | 40, 5 | (L, 40) | 1 | ReLU |
| Layer 11 | Convolution 1D | 40, 5 | (L, 40) | 1 | ReLU |
| Merge activations | Merge - layer 5, 8 and 11.mode = 'sum' | — | (L, 40) | — | — |

TABLE 1-continued

An example of a 3-state secondary structure prediction model

| Layer | Type | Number of Kernels, Window size | Shape | Atrous rate | Activation |
|---|---|---|---|---|---|
| Layer 12 | Convolution 1D | 40, 5 | (L, 40) | 1 | ReLU |
| Layer 13 | Convolution 1D | 40, 5 | (L, 40) | 1 | ReLU |
| Output layer | Convolution 1D | 1, 3 | (L, 3) | — | Soft-max |

TABLE 2

An example of a 3-state solvent accessibility model

| Layer | Type | Number of Kernels, Window size | Shape | Atrous rate | Activation |
|---|---|---|---|---|---|
| Input Sequence (layer 1a) | Convolution 1D | 40, 1 | (L, 40) | 1 | Linear |
| Input PSSM (layer 1b) | Convolution 1D | 40, 1 | (L, 40) | 1 | Linear |
| Merging Sequence + PSSM | Merge (mode = Concatenate) | — | (L, 80) | — | — |
| Layer 2 | Convolution 1D | 40, 5 | (L, 40) | 1 | Linear |
| Layer 3 | Convolution 1D | 40, 5 | (L, 40) | 1 | ReLU |
| Layer 4 | Convolution 1D | 40, 5 | (L, 40) | 1 | ReLU |
| Layer 5 | Convolution 1D | 40, 5 | (L, 40) | 1 | ReLU |
| Layer 6 | Convolution 1D | 40, 5 | (L, 40) | 1 | ReLU |
| Layer 7 | Convolution 1D | 40, 5 | (L, 40) | 1 | ReLU |
| Layer 8 | Convolution 1D | 40, 5 | (L, 40) | 1 | ReLU |
| Layer 9 | Convolution 1D | 40, 5 | (L, 40) | 2 | ReLU |
| Layer 10 | Convolution 1D | 40, 5 | (L, 40) | 2 | ReLU |
| Layer 11 | Convolution 1D | 40, 5 | (L, 40) | 2 | ReLU |
| Merge activations | Merge - layer 5, 8 and 11.mode = 'sum' | — | (L, 40) | — | — |
| Layer 12 | Convolution 1D | 40, 5 | (L, 40) | 1 | ReLU |
| Layer 13 | Convolution 1D | 40, 5 | (L, 40) | 1 | ReLU |
| Outputlayer | Convolution 1D | 1, 3 | (L, 3) | — | Soft-max |

C. Pathogenicity Prediction Network Architecture

With respect to the pathogenicity prediction model, semi-supervised deep convolutional neural network (CNN) models were developed to predict pathogenicity of variants. The input features to the models include protein sequences and conservation profiles flanking variants and depletion of missense variants in specific gene regions. The changes caused by variants to secondary structure and solvent accessibility were also predicted by deep learning models and this was integrated into the pathogenicity prediction model. Predicted pathogenicity in one such implementation is on a scale from 0 (benign) to 1 (pathogenic).

The architecture for one such pathogenicity classification neural network (e.g., PrimateAI) is described schematically in FIG. 3 and, in a more detailed example, in Table 3 (below). In the example shown in FIG. 3, 1D refers to 1-dimensional convolutional layer. In other implementations, the model can use different types of convolutions such as 2D convolutions, 3D convolutions, dilated or atrous convolutions, transposed convolutions, separable convolutions, depthwise separable convolutions, and so forth. Further, as noted above, certain implementations of both the deep learning network for pathogenicity prediction (e.g., PrimateAI or pAI) and deep learning networks for predicting secondary structure and solvent accessibility adopted the architecture of residual blocks.

In certain embodiments, some or all layers of the deep residual network use a ReLU activation function, which greatly accelerates the convergence of stochastic gradient descent compared to saturating nonlinearities such as sigmoid or hyperbolic tangent. Other examples of activation functions that can be used by the technology disclosed include parametric ReLU, leaky ReLU, and exponential linear unit (ELU).

As described herein, some or all layers may also employ batch normalization by which distribution of each layer in a convolution neural network (CNN) changes during training and it varies from one layer to another. This reduces the convergence speed of the optimization algorithm.

TABLE 3

A pathogenicity prediction model, according to one implementation

| Layer | Type | # of Kernels, Window size | Shape | Atrous rate | Activation |
|---|---|---|---|---|---|
| Reference sequence (1a) | Convolution 1D | 40, 1 | (51, 40) | 1 | Linear |
| Alternative sequence (1b) | Convolution 1D | 40, 1 | (51, 40) | 1 | Linear |
| Primate conservation (1c) | Convolution 1D | 40, 1 | (51, 40) | 1 | Linear |
| Mammal Conservation (1d) | Convolution 1D | 40, 1 | (51, 40) | 1 | Linear |
| Vertebrate Conservation (1e) | Convolution 1D | 40, 1 | (51, 40) | 1 | Linear |
| Reference-sequence-based Secondary structure (10 | Input layer | — | (51, 40) | — | — |
| Alternative-sequence-based secondary structure (1g) | Input layer | — | (51, 40) | — | — |
| Reference-sequence-based solvent accessibility (1h) | Input layer | — | (51, 40) | — | — |

TABLE 3-continued

A pathogenicity prediction model, according to one implementation

| Layer | Type | # of Kernels, Window size | Shape | Atrous rate | Activation |
|---|---|---|---|---|---|
| Alternative-sequence-based solvent accessibility (1i) | Input layer | — | (51, 40) | — | — |
| Reference sequence merge (2a) | Merge (mode = Sum) (1a, 1c, 1d, 1e ) | — | (51, 40) | — | — |
| Alternative sequence merge (2b) | Merge (mode = Sum) (1b, lc, 1d, le ) | — | (51, 40) | — | — |
| 3a | Convolution 1D (2a) | 40, 5 | (51, 40) | 1 | ReLU |
| 3b | Convolution 1D (2b) | 40, 5 | (51, 40) | 1 | ReLU |
| 4 | Merge (mode = concatenate) (3a, 3b, 1f, 1g, 1h, 1i) | — | (51, 240) | — | — |
| 5 | Convolution 1D | 40, 5 | (51, 40) | 1 | ReLU |
| 6 | Convolution 1D | 40, 5 | (51, 40) | 1 | ReLU |
| 7 | Convolution 1D | 40, 5 | (51, 40) | 1 | ReLU |
| 8 | Convolution 1D | 40, 5 | (51, 40) | 1 | ReLU |
| 9 | Convolution 1D | 40, 5 | (51, 40) | 2 | ReLU |
| 10 | Convolution 1D | 40, 5 | (51, 40) | 2 | ReLU |
| 11 | Convolution 1D | 40, 1 | (51, 1) | 2 | Sigmoid |
| 12 | Global max pooling | — | 1 | — | — |
| Output layer | Activation layer | — | 1 | — | Sigmoid |

Example Implementation—Model Architecture

Figure 3:
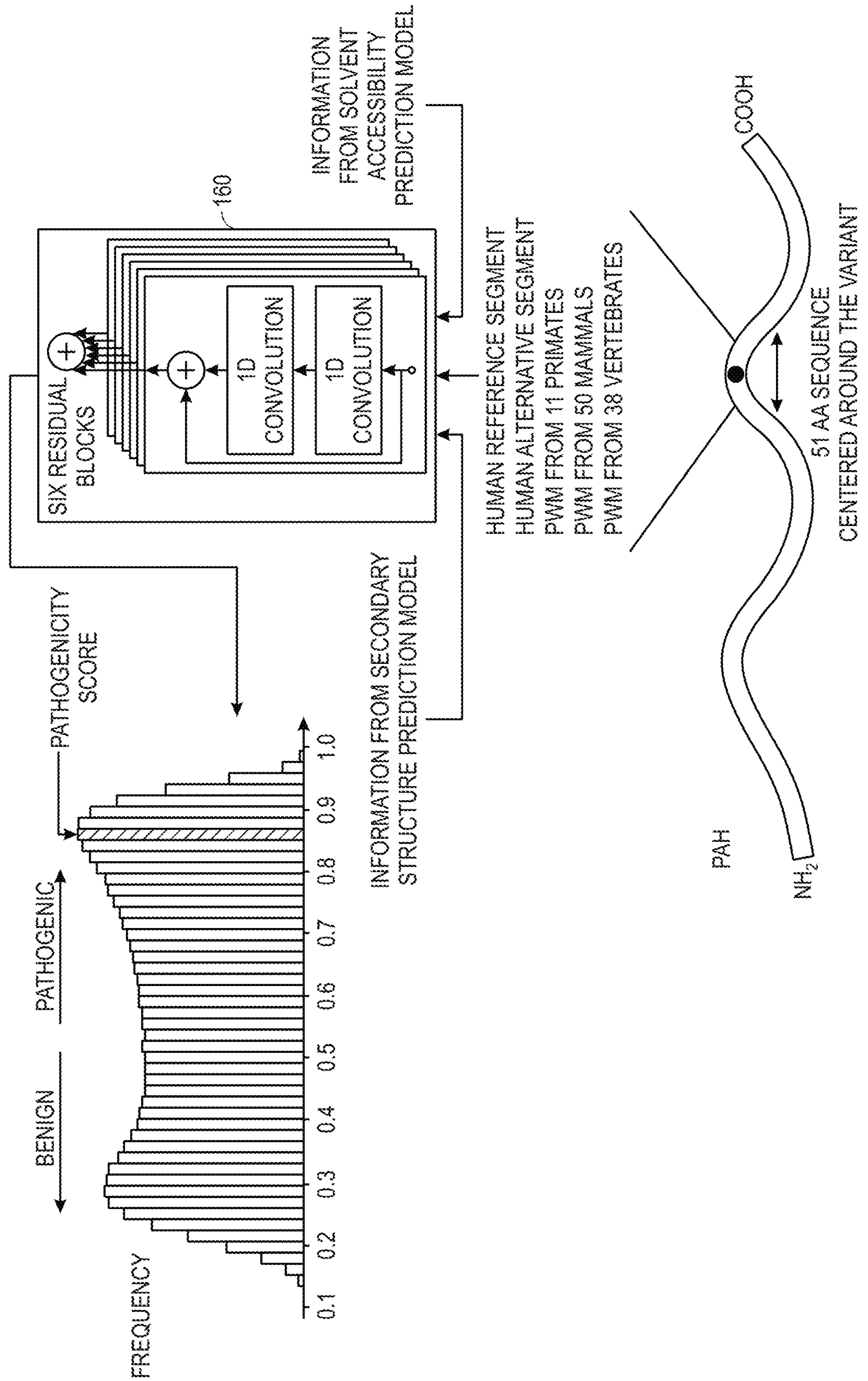
FIG. 3 shows an example architecture of a deep residual network for pathogenicity prediction, in accordance with one implementation of the technology disclosed.

With the preceding in mind, and with reference to FIG. 3 and Table 3, in one implementation the pathogenicity prediction network receives five direct inputs and four indirect inputs. The five direct inputs in such an example may include an amino acid sequence of suitable dimensions (e.g., 51-length amino acid sequences×20-depth) (encoding the 20 different amino acids), and comprise the reference human amino acid sequence (1a) without the variant, the alternative human amino acid sequence (1b) with the variant substituted in, the position-specific frequency matrices (PFM) from the multiple sequence alignment of primate species (1c), the PFM from the multiple sequence alignment of mammalian species (1d), and the PFM from the multiple sequence alignment of more distant vertebrate species (1e). The indirect inputs include reference-sequence-based secondary structure (1f), alternative-sequence-based secondary structure (1g), reference-sequence-based solvent accessibility (1h), and alternative-sequence-based solvent accessibility (1i).

For indirect inputs 1f and 1g, the pre-trained layers of the secondary structure prediction model are loaded, excluding the softmax layer. For input 1f, the pre-trained layers are based on the human reference sequence for the variants along with the PSSM generated by PSI-BLAST for the variant. Likewise, for input 1g, the pre-trained layers of the secondary structure prediction models are based on the human alternative sequence as the input along with the PSSM matrix. Inputs 1h and 1i correspond to the similar pre-trained channels containing the solvent accessibility information for reference and alternative sequences of the variant, respectively.

In this example, the five direct input channels are passed through an upsampling convolution layer of 40 kernels with linear activations. The layers 1a, 1c, 1d and 1e are merged with values summed across the 40 feature dimensions to produce layer 2a. In other words, the feature map of the reference sequence is merged with the three types of conservation feature maps. Similarly, 1b, 1c, 1d, and 1e are merged with values summed across the 40 feature dimensions to generate layer 2b, i.e., the features of the alternative sequence is merged with the three types of conservation features.

The layers 2a and 2b are batch normalized with the activation of ReLU and each passed through a 1D convolution layer of filter size 40 (3a and 3b). The outputs of layers 3a and 3b are merged with 1f, 1g, 1h, and 1i with the feature maps concatenated to each other. In other words, the feature maps of reference sequence with conservation profile, and alternative sequence with the conservation profile are merged with the secondary structure feature maps of the reference and alternative sequence and the solvent accessibility feature maps of the reference and alternative sequence (layer 4).

The outputs of layer 4 are passed through six residual blocks (layers 5, 6, 7, 8, 9, 10). The last three residual blocks have an atrous rate of 2 for the 1D convolutions, to give higher coverage for the kernels. The output of layer 10 is passed through a 1D convolution of filter size 1 and activation sigmoid (layer 11). The output of layer 11 is passed through a global maxpool that picks a single value for the variant. This value represents the pathogenicity of the variant. The details of one implementation of the pathogenicity prediction model are shown in Table 3.

D. Training (Semi-Supervised) and Data Distribution

With respect to semi-supervised learning approaches, such techniques allow utilization of both labeled and unlabeled data for training the network(s). The motivation for choosing semi-supervised learning is that human-curated variant databases are unreliable and noisy, and in particular, lack reliable pathogenic variants. Because semi-supervised learning algorithms use both labeled and unlabeled instances in the training process, they can produce classifiers that achieve better performance than completely supervised learning algorithms that have only a small amount of labeled data available for training. The principle behind semi-supervised learning is that intrinsic knowledge within unlabeled data can be leveraged in order to strengthen the prediction capability of a supervised model that only uses labeled instances, thereby providing a potential advantage for semi-supervised learning. Model parameters learned by a supervised classifier from a small amount of labeled data may be steered towards a more realistic distribution (which more closely resembles the distribution of the test data) by the unlabeled data.

Another challenge that is prevalent in bioinformatics is the data imbalance problem. The data imbalance phenomenon arises when one of the classes to be predicted is underrepresented in the data because instances belonging to that class are rare (noteworthy cases) or hard to obtain. Minority classes are typically the most important to learn because they may be associated with special cases.

An algorithmic approach to handle imbalanced data distributions is based on ensembles of classifiers. Limited amounts of labeled data naturally lead to weaker classifiers, but ensembles of weak classifiers tend to surpass the performance of any single constituent classifier. Moreover, ensembles typically improve the prediction accuracy obtained from a single classifier by a factor that validates the effort and cost associated with learning multiple models. Intuitively, aggregating several classifiers leads to better overfitting control, since averaging the high variability of individual classifiers also averages the classifiers' overfitting.

IV. Gene-Specific Pathogenicity Score Thresholds

While the preceding relates to the training and validation of a pathogenicity classifier implemented as a neural network, the following sections relate various implementation-specific and use-case scenarios for further refining and/or utilizing pathogenicity classification using such a network. In a first aspect, discussion of scoring thresholds and the use of such score thresholds is described.

Figure 4:
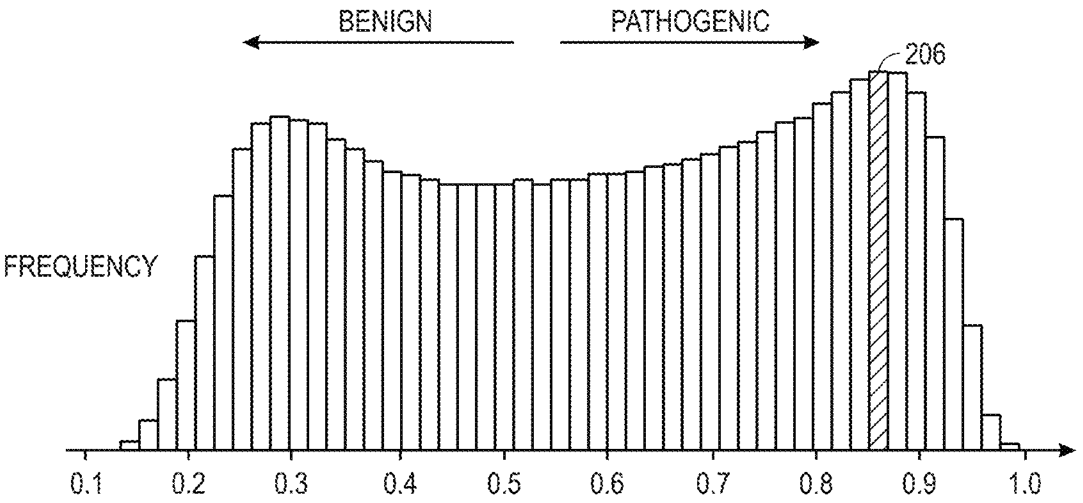
FIG. 4 depicts a pathogenicity score distribution, in accordance with one implementation of the technology disclosed.

As noted herein, a presently disclosed pathogenicity classification network, such as (but not limited to) the PrimateAI or pAI classifier described herein, may be used to generate a pathogenicity score useful for distinguishing or screening pathogenic variants from benign variants within genes. Because pathogenicity scoring as described herein is based on the extent of purifying selection in humans and non-human primates, pathogenicity scores associated with pathogenic and benign variants are expected to be higher in the genes that are under strong purifying selection. On the other hand, for genes under neutral evolution or weak selection, the pathogenicity scores for pathogenic variants tend to be lower. This concept is illustrated visually in FIG. 4, where a pathogenicity score 206 for a variant is illustrated within a distribution of scores for a respective gene. As may be appreciated with reference to FIG. 4, in practice it may be useful to have an approximate gene-specific threshold(s) for identifying variants that are likely to be pathogenic or benign.

To assess possible thresholds that might be useful in assessing pathogenicity scores, potential score thresholds were studied using 84 genes which contained at least 10 benign/likely benign variants and at least 10 pathogenic and likely pathogenic variants in ClinVar. These genes were used to help evaluate suitable pathogenicity score thresholds for each gene. For each of these genes, the mean pathogenicity scores were measured for benign and pathogenic variants in ClinVar.

Figure 5:
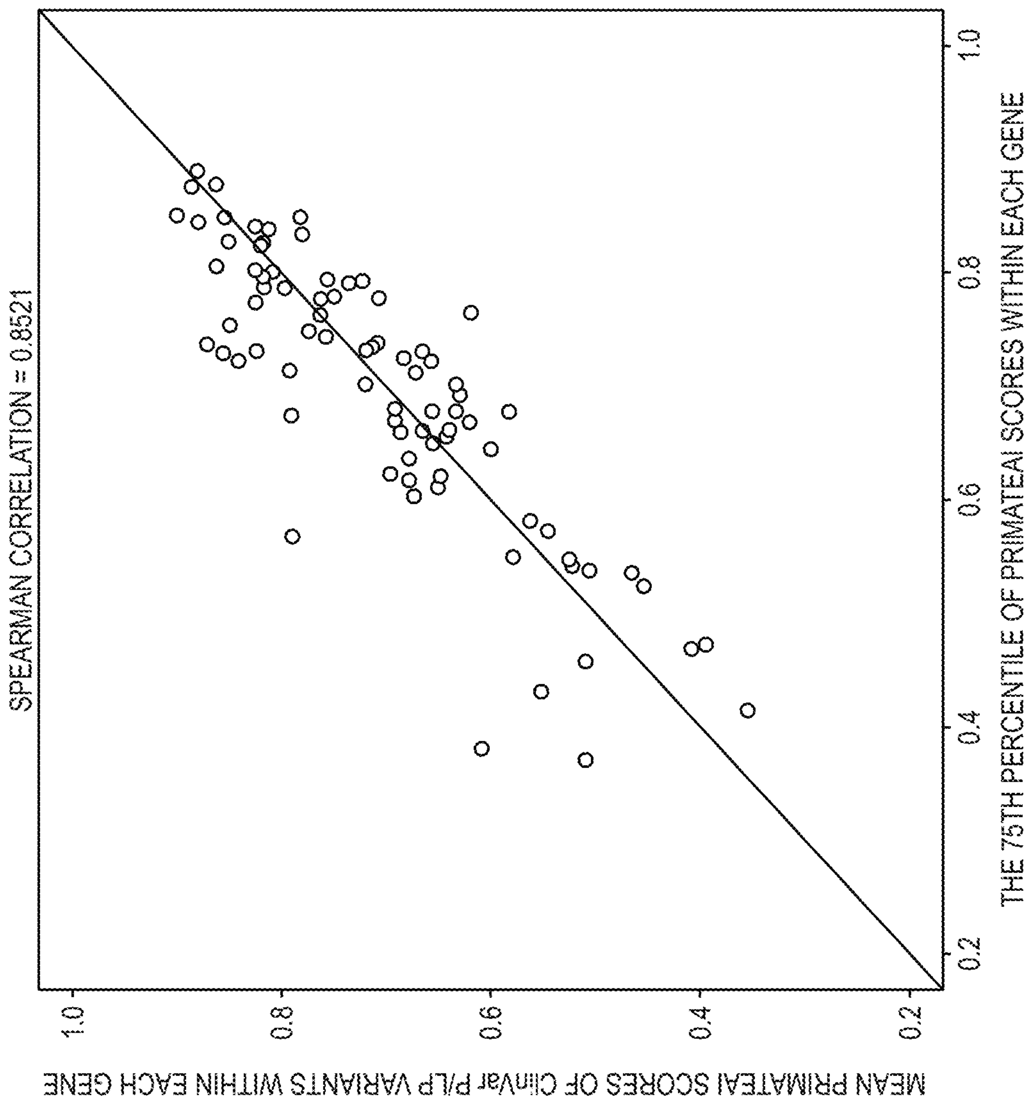
FIG. 5 depicts a plot of the correlation of mean pathogenicity scores for ClinVar pathogenic variants to pathogenicity scores at the 75th percentile of all missense variants in that gene, in accordance with one implementation of the technology disclosed.
Figure 6:
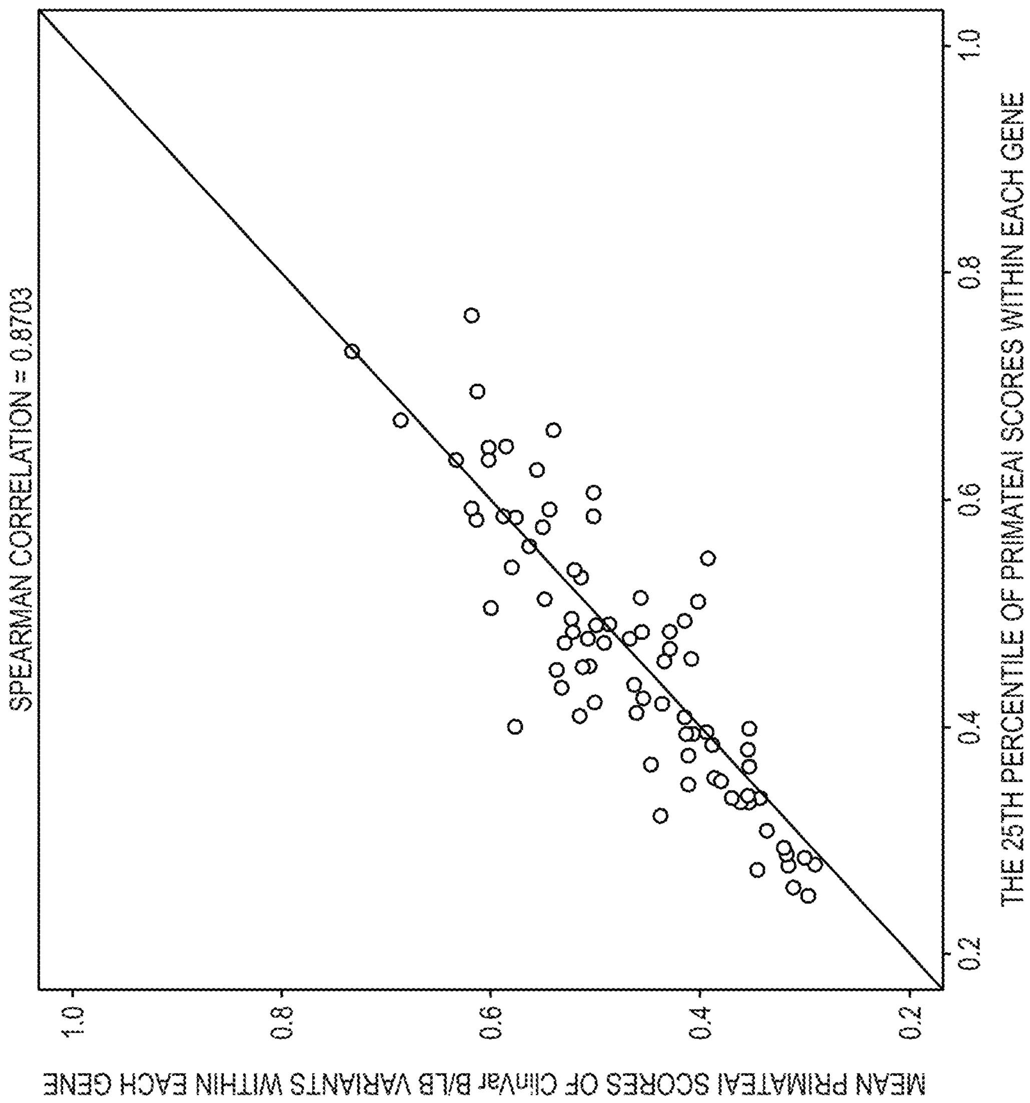
FIG. 6 depicts a plot of the correlation of mean pathogenicity scores for ClinVar benign variants to pathogenicity scores at the 25th percentile of all missense variants in that gene, in accordance with one implementation of the technology disclosed.

In one implementation, it was observed that mean pathogenicity scores for pathogenic and benign ClinVar variants in each gene correlated well with the 75th and 25th percentiles of pathogenicity scores (here PrimateAI or pAI scores) in that gene, as shown graphically in FIG. 5, which illustrates the gene-specific PrimateAI thresholds for pathogenic variants, and FIG. 6, which illustrates the gene-specific PrimateAI thresholds for benign variants. In both figures each gene is represented by a dot with the gene symbol label above. In these examples, the mean PrimateAI scores for ClinVar pathogenic variants correlated closely with the PrimateAI scores at the 75th percentile of all missense variants in that gene (Spearman correlation=0.8521, FIG. 5). Likewise, the mean PrimateAI scores for ClinVar benign variants correlated closely with PrimateAI scores at the 25th percentile of all missense variants in that gene (Spearman correlation=0.8703, FIG. 6).

In view of the present approach, a suitable percentile of pathogenicity score per gene for use as a cutoff for likely pathogenic variants may be in the range defined by and including the 51st percentile to the 99th percentile (e.g., the $65^{th}$, $70^{th}$, $75^{th}$, $80^{th}$, or $85^{th}$ percentile). Conversely, a suitable percentile of pathogenicity score per gene for use as a cutoff for likely benign variants may be in the range defined by and including the 1st percentile to the 49th percentile (e.g., the $15^{th}$, $20^{th}$, $25^{th}$, $30^{th}$, or $35^{th}$ percentile).

Figure 7:
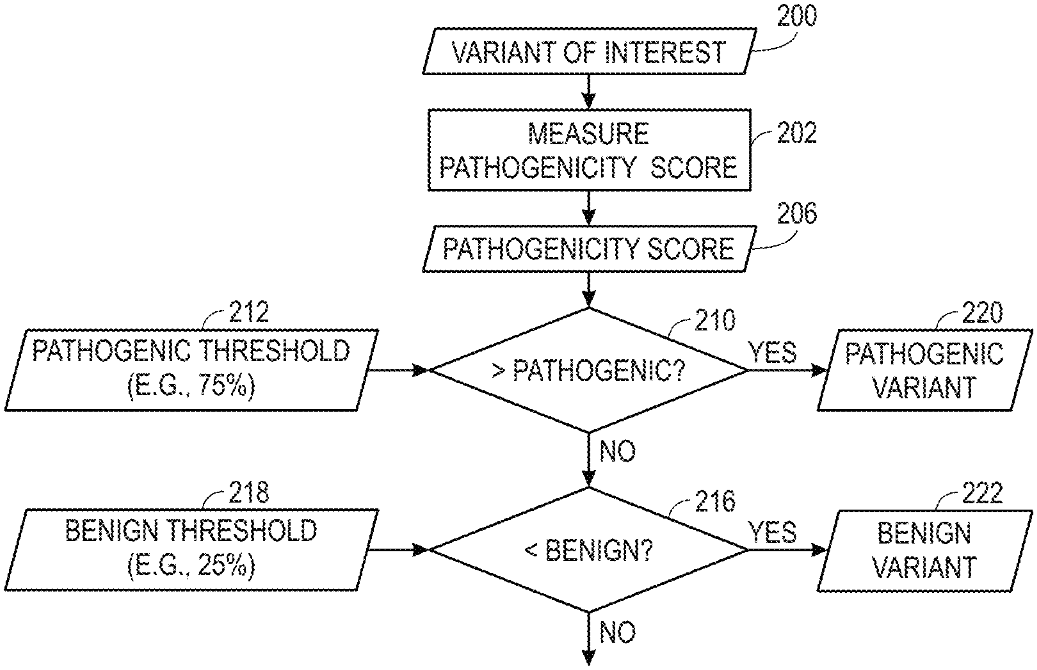
FIG. 7 depicts a sample process flow by which thresholds may be used to characterize variants into benign or pathogenic categories based on their pathogenicity score, in accordance with one implementation of the technology disclosed.

With respect to use of these thresholds, FIG. 7 illustrates a sample process flow by which such thresholds may be used to sort variants into benign or pathogenic categories based on their pathogenicity score 206. In this example a variant of interest 200 may be processed using a pathogenicity scoring neural network (step 202) as described herein to derive a pathogenicity score 206 for the variant of interest 200. In the depicted example, the pathogenicity score is compared (decision block 210) to a gene-specific pathogenic threshold 212 (e.g., (75%) and, if not determined to be pathogenic, compared (decision block 216) to a gene-specific benign threshold 218. Although the comparison process in this example is shown as occurring serially for simplicity, in practice the comparisons may be performed in a single step, in parallel, or, alternatively, only one of the comparisons may be performed (e.g., determining whether the variant is pathogenic). If the pathogenic threshold 212 is exceeded, the variant of interest 200 may be deemed a pathogenic variant 220 while, conversely, if the pathogenicity score 206 is below the benign threshold 212, the variant of interest 200 may be deemed a benign variant 222. If neither threshold criteria is met, the variant of interest may be treated as neither pathogenic nor benign. In one study, gene-specific thresholds and metrics were derived and evaluated for 17,948 unique genes within the ClinVar database using the approaches described herein.

V. Estimation of Selection Effects Against all Human Variants Based on Pathogenicity Scores Using Forward Time Simulations Clinical studies and patient care are example use-case scenarios in which a pathogenicity classification network, such as PrimateAI, may be employed to classify and/or separate pathogenic variants from benign variants within genes. In particular, clinical genome sequencing has become standard-of-care for patients with rare genetic diseases. Rare genetic diseases are often, if not primarily, caused by highly deleterious rare mutations, which are generally easier to detect due to their severity. However, those rare mutations that underlie common genetic diseases remain largely uncharacterized due to their weak effects and large numbers.

With this in mind, it may be desirable to understand the mechanism between rare mutations and common diseases and to study the evolutionary dynamics of human mutations, particularly in the context of pathogenicity scoring of variants as discussed herein. During the evolution of human population, new variants have been constantly generated by de novo mutation while some of them have also been removed due to natural selection. If the human population size was constant, the allele frequencies of variants affected by the two forces would ultimately reach equilibrium. With this in mind, it may be desirable to use observed allele frequencies to determine the severity of nature selection on any variants.

Figure 8:
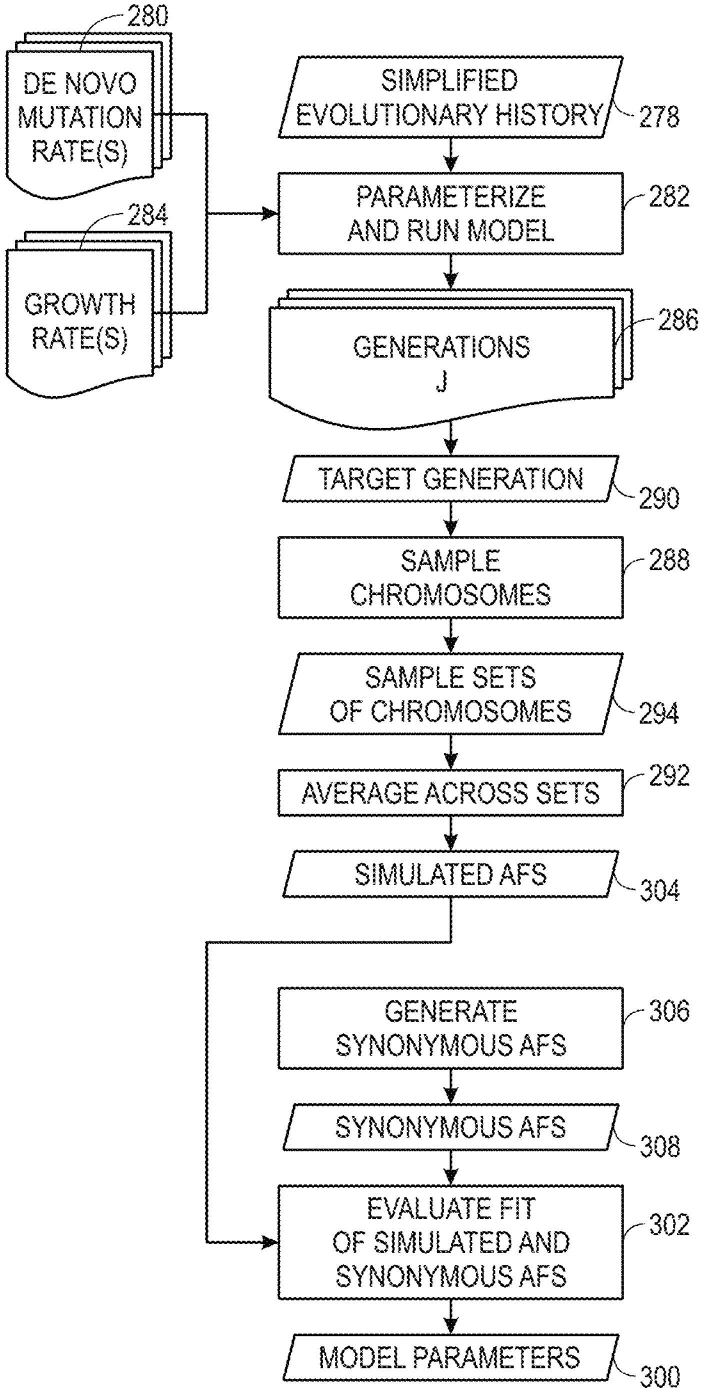
FIG. 8 depicts a sample process flow by which optimal forward time model parameters may be derived, in accordance with one implementation of the technology disclosed.

However, the human population is not in the steady state at any moment, and has been instead exponentially expanding since the advent of agriculture. Therefore, in accordance with certain approaches discussed herein, forward time simulation may be used as a tool to investigate the effects of the two forces on the distribution of allele frequencies of variants. Aspects of this approach are described with respect to the steps illustrated in FIG. 8, which may be referenced and returned to as deriving optimal forward time model parameters is discussed.

With this in mind, a forward time simulation of neutral evolution using de novo mutation rates 280 may be employed as part of modeling (step 282) the distribution of allele frequencies of variants over time. As a baseline, a forward-time population model may be simulated assuming neutral evolution. Model parameters 300 were derived by fitting (step 302) simulated allele frequency spectra (AFS) 304 to that of the observed synonymous mutations (synonymous AFS 308) in the human genome. A simulated AFS 304 generated using the set of optimal model parameters 300 (i.e., those parameters corresponding to the best fit) may then be used in conjunction with other concepts as discussed herein, such as variant pathogenicity scoring, to derive useful clinical information.

Figure 9:
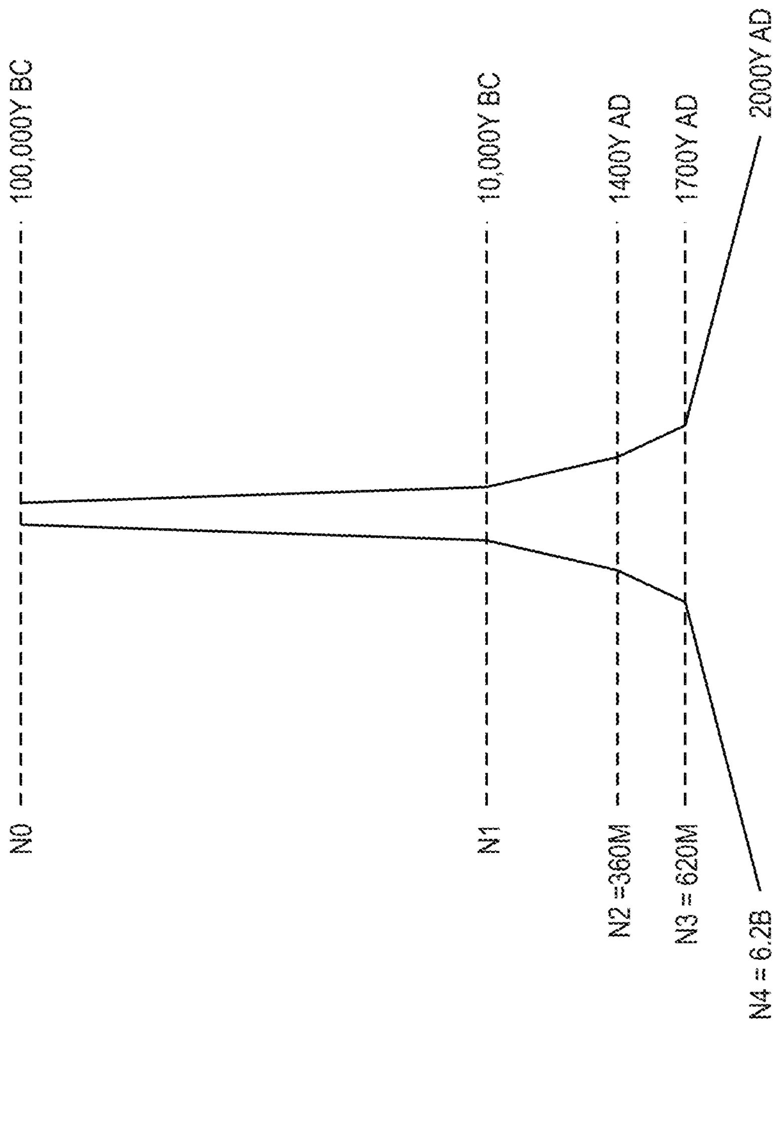
FIG. 9 depicts evolutionary history of the human population simplified into four stages of exponential expansion with different growth rates, in accordance with one implementation of the technology disclosed.

As the distribution of rare variants is of primary interest, the evolutionary history of the human population in this example implementation is simplified into four stages of exponential expansion with different growth rates in this simulation, as shown in FIG. 9, which is a schematic illustration of a simplified human population expansion model (i.e., a simplified evolutionary history 278). In this example, the ratio between census population size and effective population size may be denoted as r and the initial effective population size as Ne0=10,000. Each generation may be assumed to take about 30 years.

In this example, a long burn-in period (about 3,500 generations) with a small change in effective population size was employed in the first phase. The population size change may be denoted as n. As the time after the burn-in is unknown, this time may be denoted as T1 and the effective population size at T1 as 10,000*n. The growth rate 284 during the burn-in is g1=n^(1/3,500).

At 1400 years AD, the census population size across the world is estimated to have been about 360 million. At 1700 years AD, the census population size increased to about 620 million, and at 2000 years AD, it is 6.2 billion. Based on these estimates, the growth rates 284 at each stage can be derived as shown in Table 4:

TABLE 4

Simulation scheme

| Time point | # generations past | Effective pop. size | Census pop. size | Growth rate |
|---|---|---|---|---|
| T1 | A large burn-in (e.g., 3500) | 10,000 * n | 10,000 * r * n | n^(1/3500) |
| T2: 1400 AD | (T2 − T1)/30 | 36000/r | 360 m | (3.6/r/n) ^((T2 − T1)/30) |
| T3: 1700 AD | 10 | 62000/r | 620 m | (6.2/3.6)^(1/10) |
| T4: 2000 AD | 10 | 620000/r | 6.2 b | 10^(1/10) |

For generation j 286, $N_j$ chromosomes are randomly sampled from the previous generation to form the new-generation population, where $N_j=g_j*N_{j-1}$, where $g_j$ is the growth rate 284 at generation j. Most of mutations are inherited from the previous generation during chromosome sampling. De novo mutations are then applied to these chromosomes according to de novo mutation rates (μ) 280.

With respect to the de novo mutation rates 280, in accordance with certain implementations, these may be derived in accordance with the following approach or an equivalent approach. In particular, in one such implementation three large parental-offspring trio datasets totaling 8,071 trios were obtained with whole genome sequencing from literature sources (Halldorsson set (2976 trios), Goldmann set (1291 trios), and Sanders set (3804 trios)). Merging these 8,071 trios, the de novo mutations were obtained that are mapped to the intergenic regions and the de novo mutation rates 280 derived for each of 192 trinucleotide context configurations.

Figure 10:
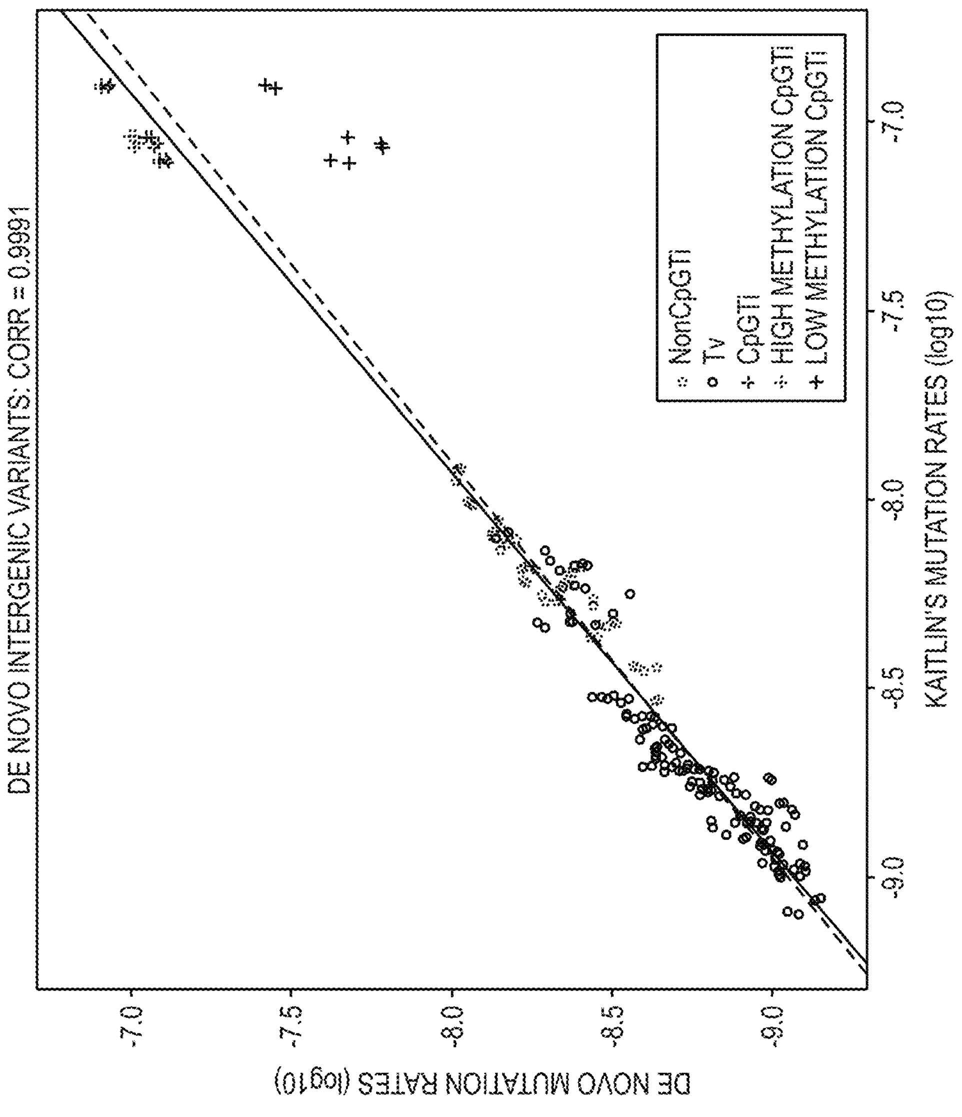
FIG. 10 depicts correlation between estimates of mutation rates derived in accordance with the present approach and other literature-derived mutation rates.

These estimates of mutation rates were compared with other literature mutation rates (Kaitlin's mutation rates derived from intergenic regions of 1,000 genome projects), as shown in FIG. 10. The correlation was 0.9991, with the present estimates being generally lower than Kaitlin's mutation rates, as shown in Table 5 (where CpGTi=transition mutation at CpG sites, non-CpGTi=transition mutation at non-CpG sites, Tv=transversion mutations).

TABLE 5

Mutation Rate Comparison

| | Kaitlin's mutation rates | | | De novo mutations | | |
|---|---|---|---|---|---|---|
| Mutation rates | Weighted mean | Mean | Median | Weighted mean | Mean | Median |
| Genome-wide | 1.2e−8 | | | 1.048189e−08 | | |
| NonCpGTi | 6.634517 | 6.700049 | 6.449612 | 5.493724 | 5.552238 | 5.339421 |

TABLE 5-continued

| Mutation Rate Comparison | | | | | | |
|---|---|---|---|---|---|---|
| | Kaitlin's mutation rates | | | De novo mutations | | |
| Mutation rates | Weighted mean | Mean | Median | Weighted mean | Mean | Median |
| (56 trinucs) | e−09 | e−09 | e−09 | e−09 | e−09 | e−09 |
| Tv | 2.101242 e−09 | 2.345956 e−09 | 1.818607 e−09 | 1.922048 e−09 | 2.034197 e−09 | 1.663312 e−09 |
| CpGTi | 9.33749e−08 | 9.486598 e−08 | 8.917675 e−08 | 9.040611 e−08 | 9.174335 e−08 | 8.593169 e−08 |
| CpGTi (high methylation) | | | | | 1.011751 e−07 | |
| CpGTi (low methylation) | | | | | 2.264356 e−08 | |

With respect to the mutation rates at CpG islands, methylation levels at CpG sites affect the mutation rates substantially. To precisely compute the CpGTi mutation rates, the methylation levels at those sites should be taken into account. With this in mind, in an example implementation the mutation rate and CpG islands may be calculated in accordance with the following approach.

Figure 11:
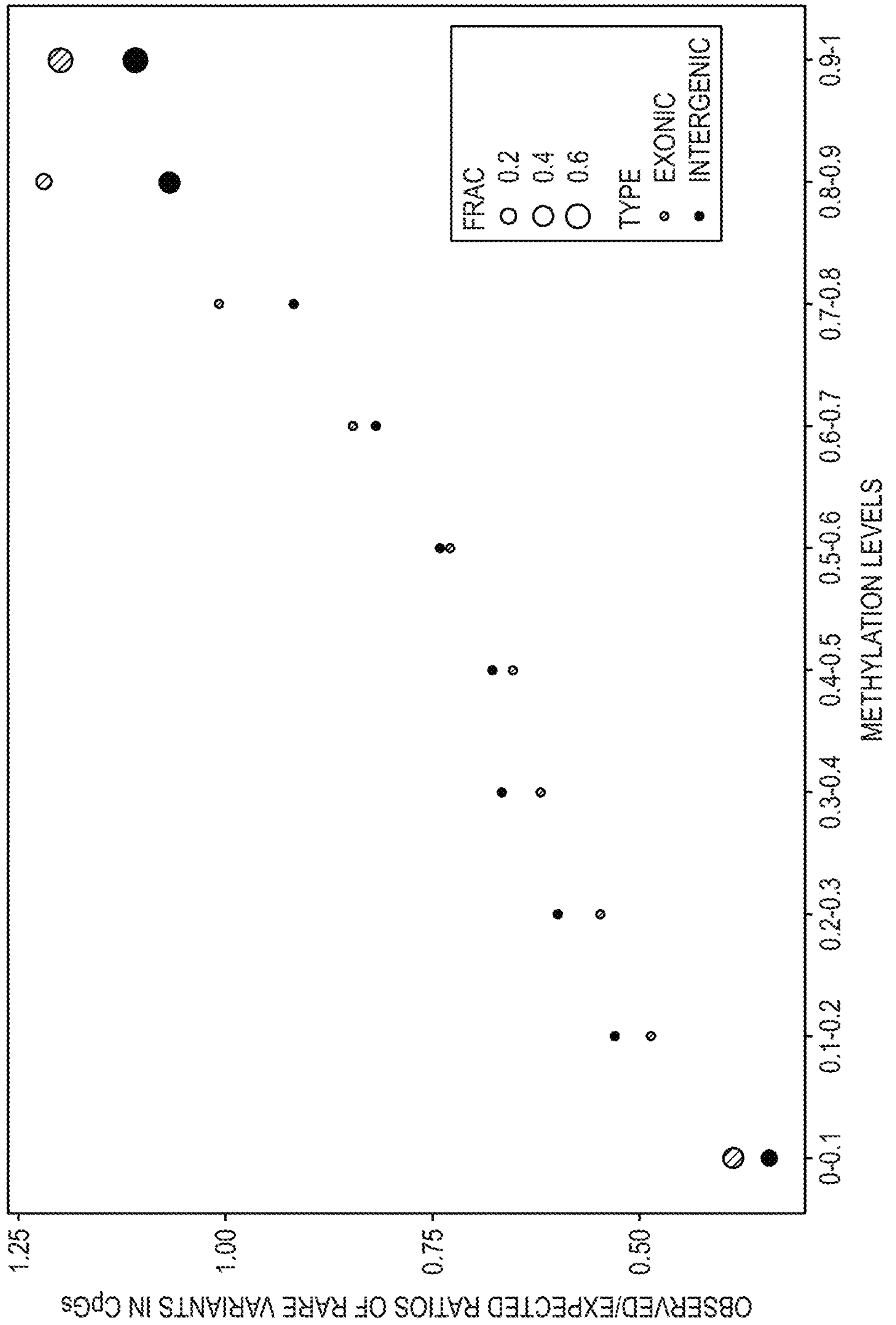
FIG. 11 depicts ratios of observed to expected numbers of CpG mutations versus methylation levels, in accordance with aspects of the present disclosure.
Figure 12A:
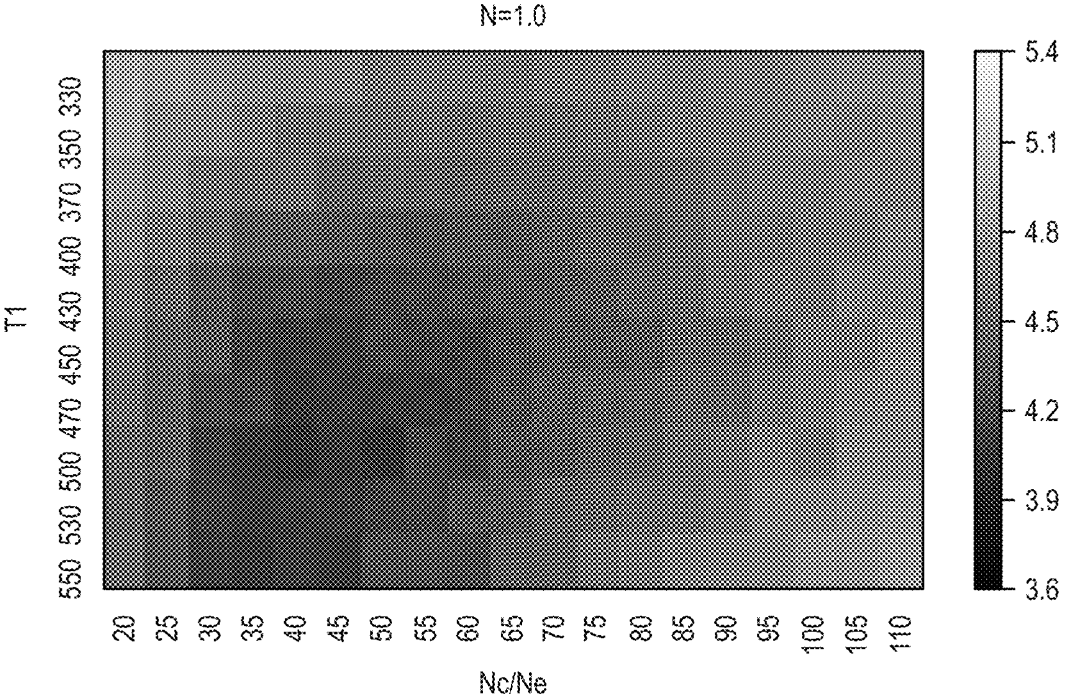
FIGS. 12A, 12B, 12C, 12D, 12E depict heatmaps of Pearson's chi-squared statistic showing the optimal parameter combination for an implementation of a forward time simulation model, in accordance with aspects of the present disclosure.
Figure 12B:
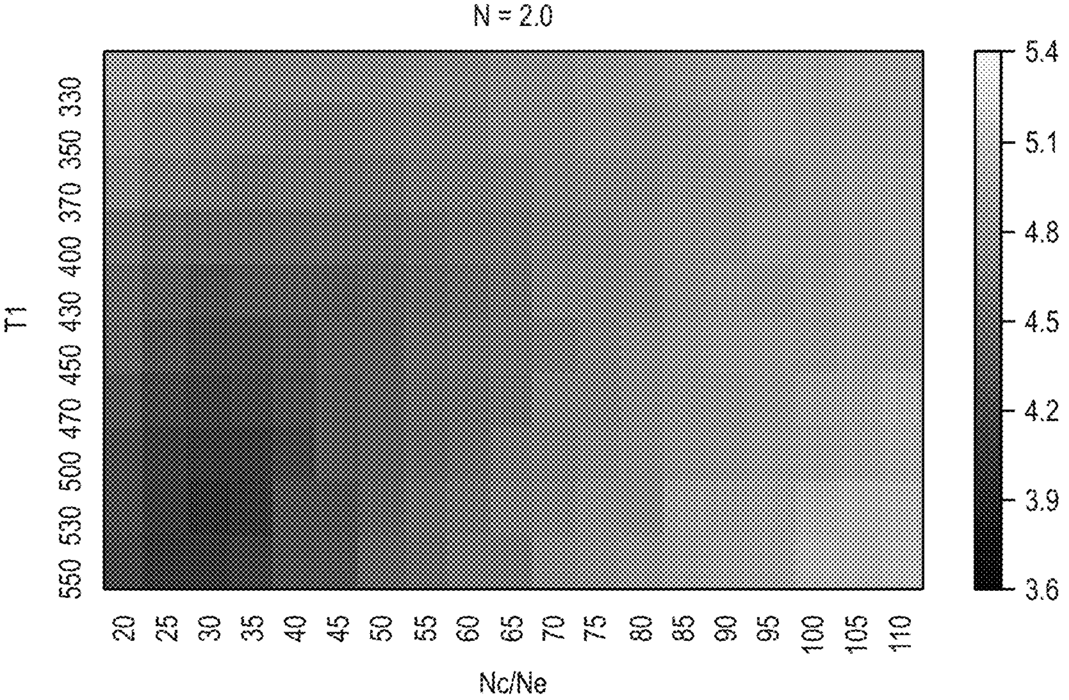
Figure 12C:
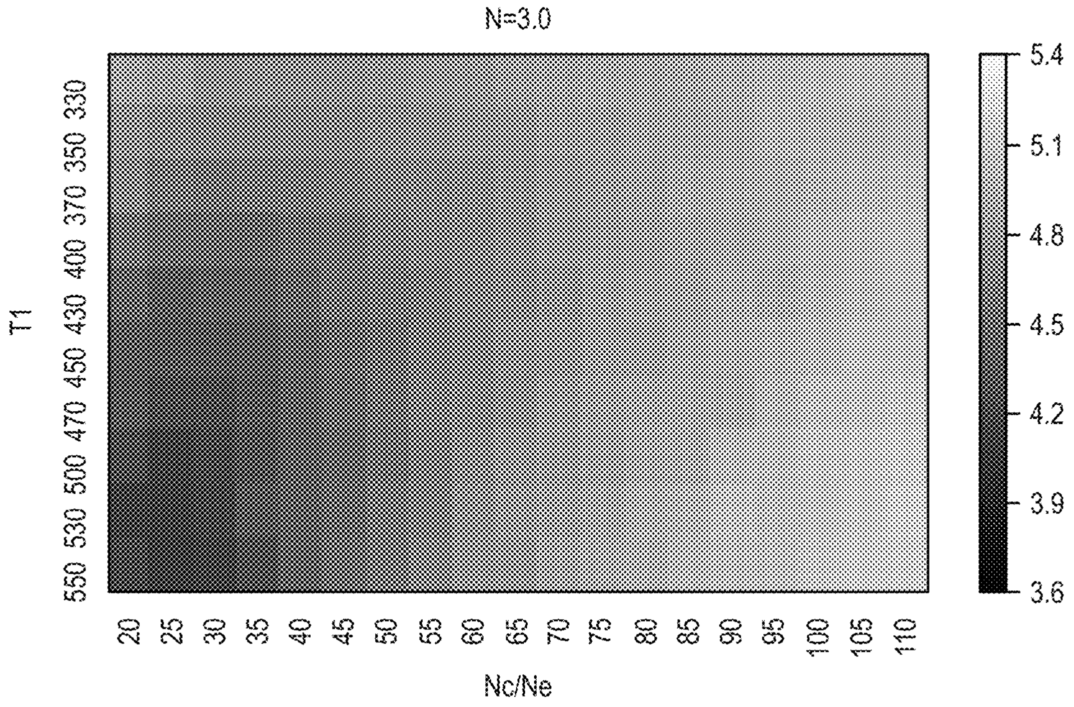
Figure 12D:
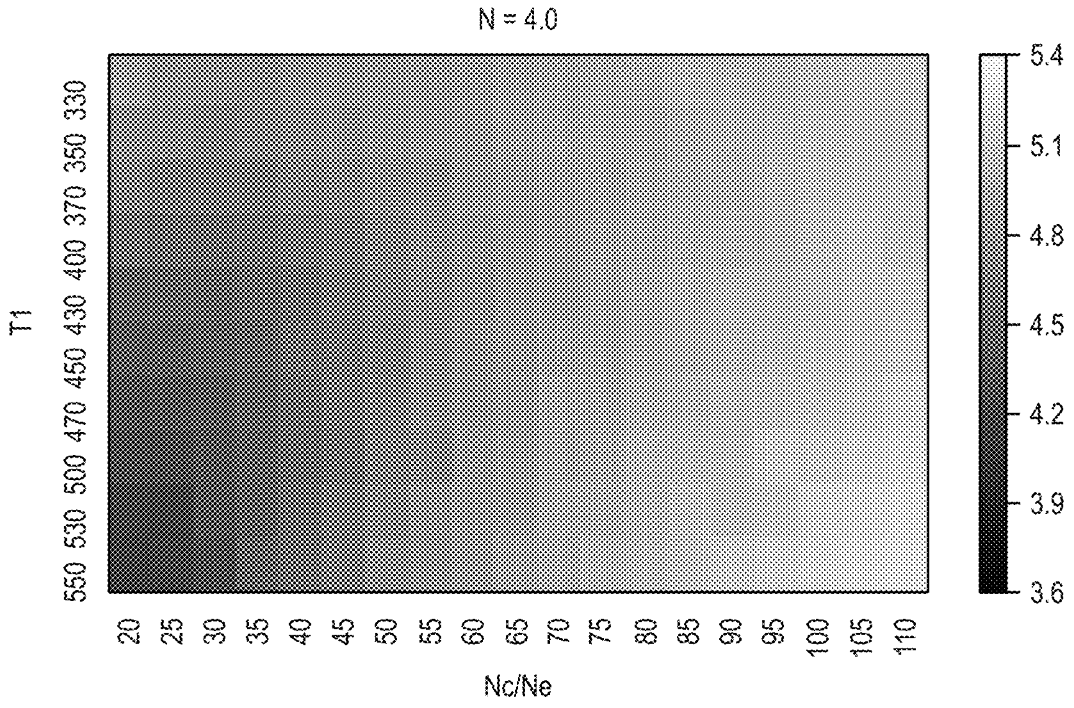
Figure 12E:
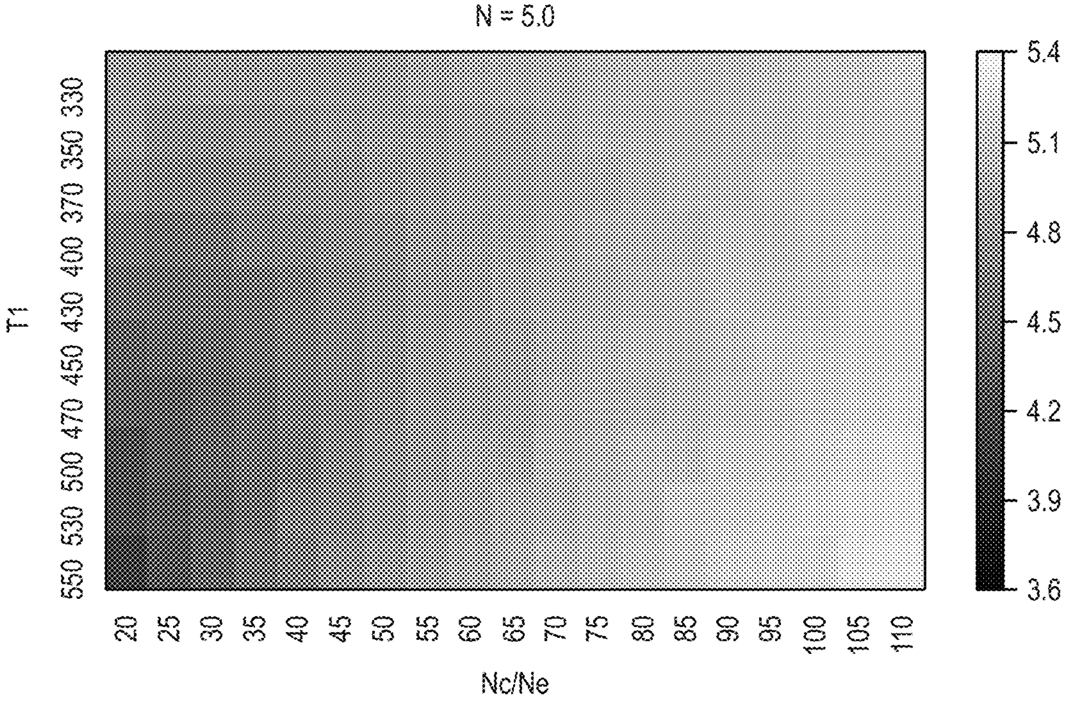

First, the impact of methylation levels on CpG mutation rates was evaluated by using whole genome bisulfite sequencing data (obtained from Roadmap Epigenomics project). The methylation data for each CpG island was extracted and averaged across 10 embryonic stem cell (ESC) samples. Those CpG islands were then separated into 10 bins based on 10 defined methylation levels, as shown in FIG. 11. The number of CpG sites, as well as the observed number of CpG transition variants, falling in each methylation bin in both intergenic and exon regions, respectively, were counted. The expected number of transition variants at CpG sites in each methylation bin was computed as the total number of CpGTi variants multiplied by the fraction of CpG sites in that methylation bin. It was observed that the ratios of observed to expected numbers of CpG mutations increased with methylation levels and that there was about a five-fold change in ratios of observed/expected numbers of CpGTi mutations between high and low methylation levels, as shown in FIG. 11.

CpG sites were classified into two types: (1) high methylation (if averaged methylation levels >0.5); and (2) low methylation (if averaged methylation levels ≤0.5). The de novo mutation rates for each of the 8 CpGTi tri-nucleotide contexts were computed for high and low methylation levels, respectively. Averaging across the 8 CpGTi tri-nucleotide contexts, the CpGTi mutation rates were obtained: 1.01e-07 for high methylation and 2.264e-08 for low methylation, as shown in Table 6.

The allele frequency spectrum (AFS) of exome sequencing data was then fitted. In one such sample implementation, simulations were performed assuming 100,000 independent sites and using various combinations of parameters, T1, r and n, where T1∈(330, 350, 370, 400, 430, 450, 470, 500, 530, 550), r∈(20, 25, 30, . . . , 100, 105, 110), and n∈(1.0, 2.0, 3.0, 4.0, 5.0) were considered.

Each of the three major classes of mutations were simulated separately using the different de novo mutation rates, i.e. CpGTi, non-CpGTi and Tv (as shown in Table 6). For CpGTi, high and low methylation levels were separately simulated and the two AFSs merged by applying the proportions of high or low methylation sites as weights.

For each combination of parameters as well as each mutation rate, a human population was simulated through present day. One thousand sets of 246,000 chromosomes were then randomly sampled (step 288) (e.g., from a target or final generation 290), corresponding to the sample size of gnomAD exomes. A simulated AFS 304 was then generated by averaging (step 292) across the one thousand respective sampled sets 294.

In terms of validation, human exome polymorphism data from genome Aggregation Database (gnomAD) v2.1.1 was acquired, which collected the whole-exome sequencing (WES) data of 123,136 individuals from eight subpopulations around the world (http://gnomad.broadinstitute.org/). Variants were excluded that did not pass filters, have median coverage <15, or fall within low complexity regions or segmental duplication regions, where the boundary of regions were defined in the file downloaded from https://storage.googleapis.com/gnomad-public/release/2.0.2/README.txt.). Variants were retained that were mapped to the canonical coding sequences defined by the UCSC genome browser for the hg19 build.

The synonymous allele frequency spectrum 308 of gnomAD was generated (step 306) by counting the number of synonymous variants in seven allele frequency categories, including singletons, doubletons, 3≤allele count (AC)≤4, . . . , and 33≤AC≤64. Variants with AC >64 were discarded as the focus was on rare variants.

Figure 13:
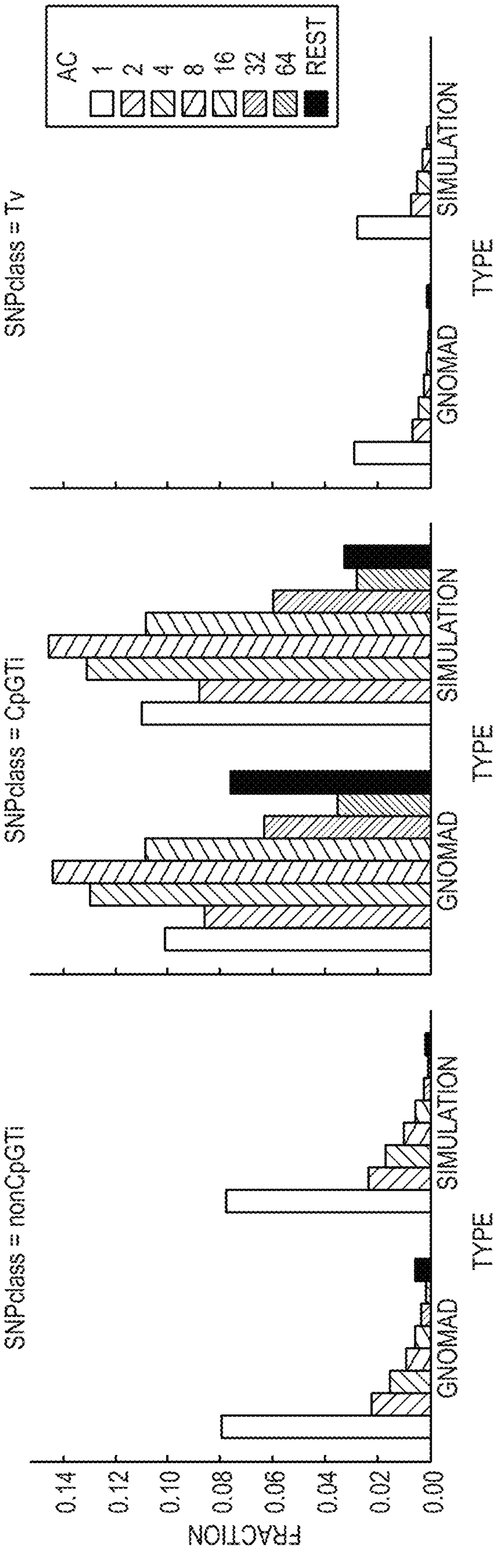
FIG. 13 illustrates that in one example, the simulated allele frequency spectrum derived using optimal model parameters determined in accordance with the present approach corresponds to the observed allele frequency spectrum.

A likelihood ratio test was applied to evaluate (step 302) the fit of the simulated AFS 304 to the gnomAD AFS (i.e., synonymous AFS 308) of rare synonymous variants across the three mutational classes. The heatmaps of Pearson's chi-squared statistic (corresponding to −2*log likelihood ratio), as shown in FIGS. 12A-12E, show the optimal parameter combination in this example (i.e., optimal model parameters 300) occurs at T1=530, r=30, and n=2.0. FIG. 13 shows that the simulated AFS 304 with this parameter combination mimics the observed gnomAD AFS (i.e., synonymous AFS 308). The estimated T1=530 generations agree with archaeology, which dates the broad adoption of agriculture to ~12,000 years ago (i.e., the beginning of the Neolithic era). The ratio between census and effective population size is lower than expected, implying that the diversity of human population is actually quite high.

Figure 14:
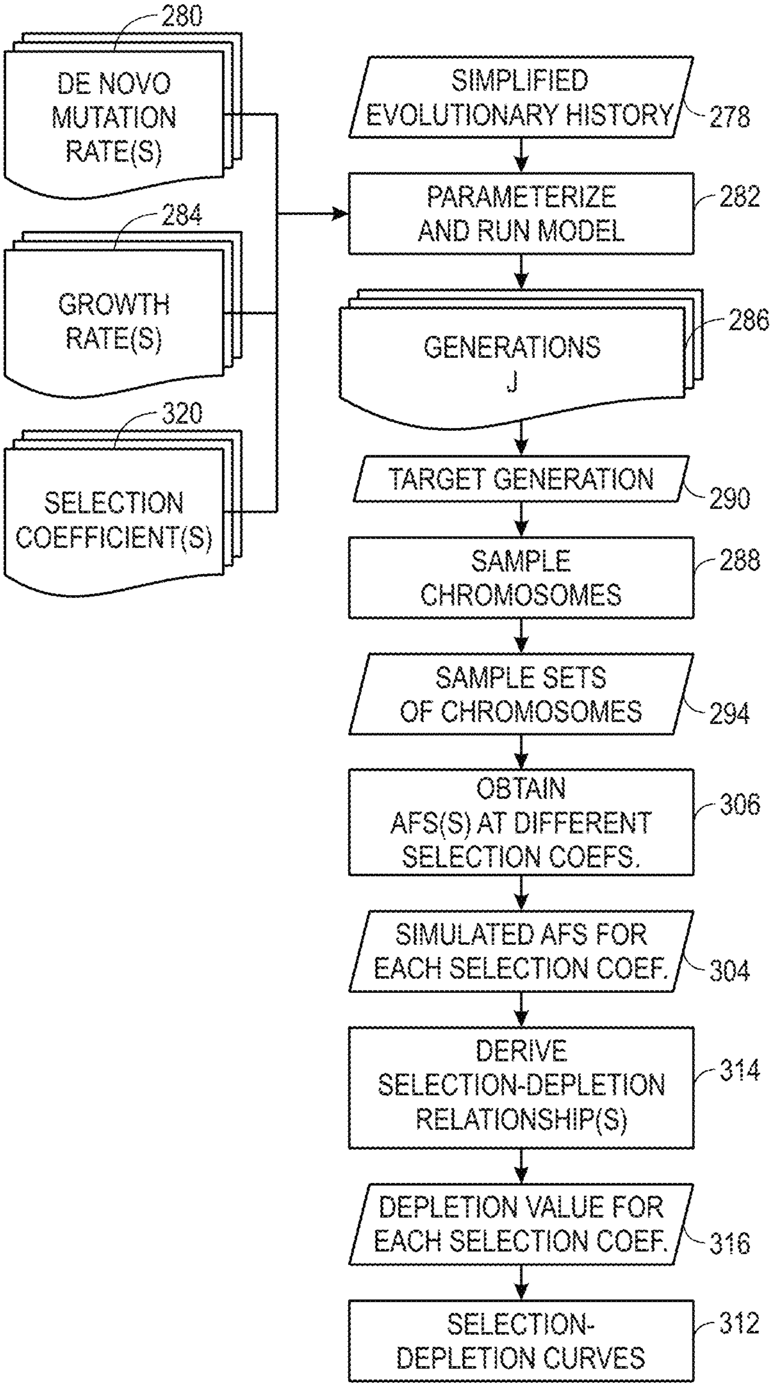
FIG. 14 depicts a sample process flow by which selection effects in the context of a forward time simulation are incorporated, in accordance with one implementation of the technology disclosed.

In one example implementation, and with reference to FIG. 14, to address selection effects in the context of the forward time simulation, the preceding simulation results were searched for the most probable demographic models of human expansion history. Based on these models, selection was incorporated into the simulations with different values of selection coefficient (s) 320 selected from {0, 0.0001, 0.0002, . . . , 0.8, 0.9}. For each generation 286, after inheriting mutations from parental population and applying de novo mutations, a small fraction of mutations were randomly purged according to a selection coefficient 320.

To improve the precision of the simulation, separate simulation was applied (step 282) for each of the 192 tri-nucleotide contexts using their specific de novo mutation rates 230 derived from 8071 trios (i.e., parent-offspring trios). Under each value of selection coefficient 320 and each mutation rate 280, a human population with the initial size of ~20,000 chromosomes was simulated expanding to present day. One thousand sets 294 were randomly sampled (step 288) from the resulting population (i.e., target or final generation 290). Each set contained ~500,000 chromosomes, corresponding to the sample size of gnomAD+Topmed+UK biobank. For each of the 8 CpGTi tri-nucleotide contexts, high and low methylation levels were simulated separately. The two AFSs were merged by applying the proportions of high or low methylation sites as weights.

After the AFSs for 192 tri-nucleotide contexts were obtained, these AFS were weighted by the frequency of the 192 tri-nucleotide contexts in the exome to generate the AFS of exome. This procedure was repeated for each of the 36 selection coefficients (step 306).

A selection-depletion curve 312 was then derived. In particular, as the selective pressure (s) against mutations rises, variants are expected to be progressively depleted. With the simulated AFS (304) under various levels of selection, a metric characterized as "depletion" was defined to measure the proportion of variants wiped out by purifying selection compared to the scenario under neutral evolution (i.e., without selection). In this example, depletion may be characterized as:

$$\text{Depletion} = 1 - \frac{\text{\# variants with selection}}{\text{\# variants without selection}} \tag{1}$$

Figure 15:
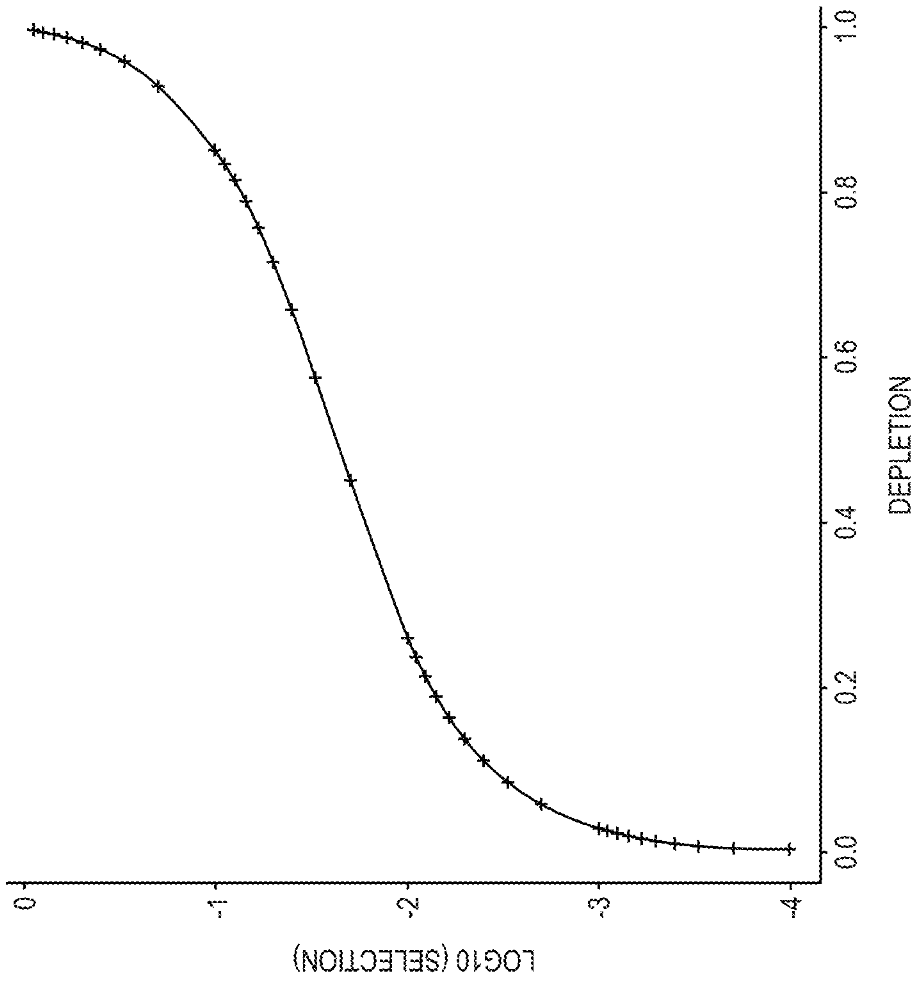
FIG. 15 depicts an example of a selection-depletion curve, in accordance with aspects of the present disclosure.

Depletion values 316 were generated for each of the 36 selection coefficients (step 314) to draw the selection-depletion curve 312 shown in FIG. 15. From this curve, interpolation can be applied to obtain the estimated selection coefficient associated with any depletion value.

With the preceding discussion regarding selection and depletion characterization using forward time simulation in mind, these factors may be used to estimate selection coefficients for missense variants based on pathogenicity (e.g., PrimateAI or pAI) scores.

Figure 16:
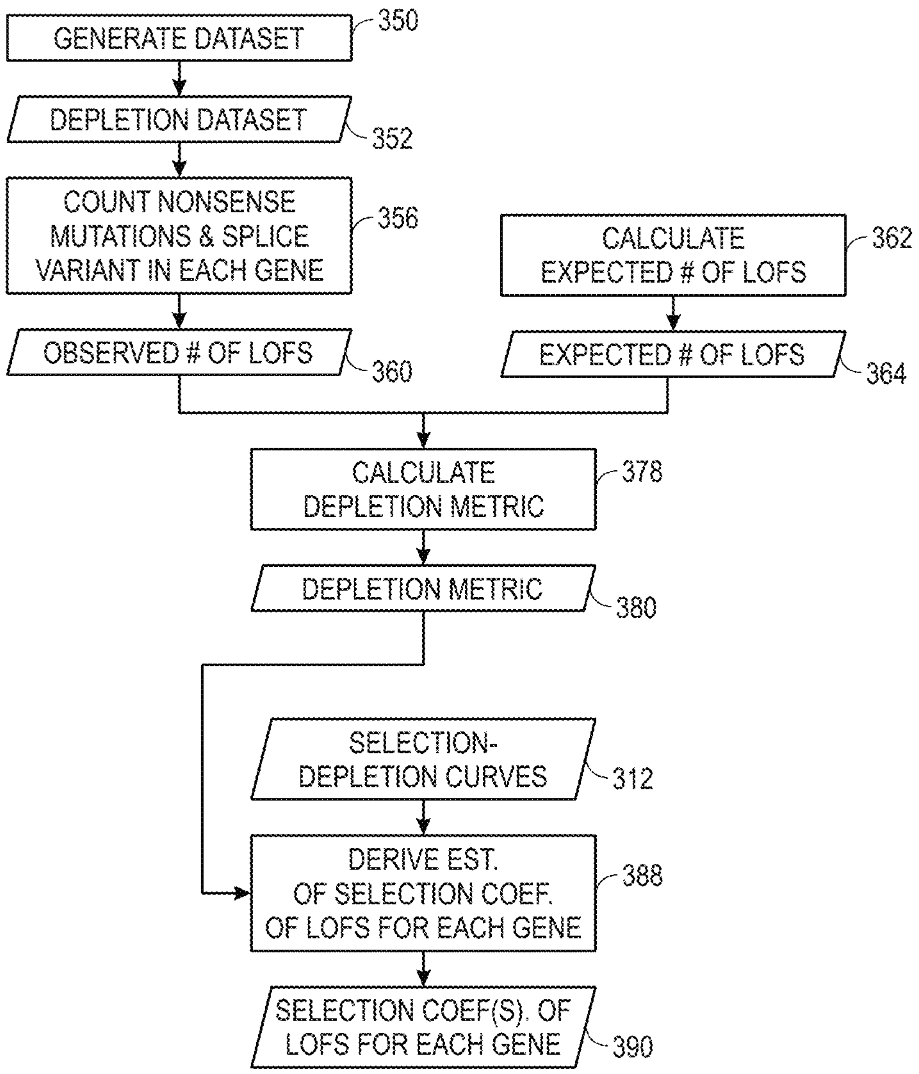
FIG. 16 depicts a sample process flow by which selection coefficients for variants of interest may be derived, in accordance with one implementation of the technology disclosed.

By way of example, and with reference to FIG. 16, in one study data was generated (step 350) by acquiring variant allele frequency data from approximately ~200,000 individuals, including 122,439 gnomAD exomes and 13,304 gnomAD whole genome sequencing (WGS) samples (after removing Topmed samples), ~65K Topmed WGS samples, and ~50K UK biobank WGS samples. Focus was on rare variants (AF <0.1%) in each dataset. All the variants were required to pass filters and have a median depth ≥1 according to gnomAD exome coverage. Variants were excluded that showed an excess of heterozygotes, defined by an inbreeding coefficient <−0.3. For whole-exomes sequencing, variants were excluded if the probability generated by the random forest model was ≥0.1. For WGS samples, variants were excluded if the probability generated by the random forest model was ≥0.4. For protein-truncating variants (PTV) (which include nonsense mutations), splice variants (i.e., those variants that occur at splicing donor or acceptor sites), and frameshifts, additional filters were applied, i.e., filtering based on low confidence estimated by a loss-of-function transcript effect estimator (LOFTEE) algorithm.

Variants were merged among the three datasets to form the final dataset 352 to compute depletion metrics. Allele frequencies were recomputed to average across the three datasets in accordance with:

$$AF = \frac{\text{sum}\,(AC_i)}{\text{sum}\,(AN_i)} \tag{2}$$

where i represents the dataset index. If a variant didn't appear in one dataset, a zero (0) was assigned to AC for that dataset.

With respect to depletion in nonsense mutations and splice variants, the fraction of PTVs depleted by purifying selection compared with the expected number in each gene may be calculated. Due to the difficulty in computing the expected number of frameshifts in a gene, focus was instead placed on nonsense mutations and splice variants, denoted as loss-of-function mutations (LOF).

The number of nonsense mutations and splice variants were counted (step 356) in each gene of the merged dataset to get the observed number of LOFs 360 (the numerator of the formula below). To calculate (step 362) the expected number of LOFs 364, the file containing constraint metrics (https://storage.googleapis.com/gnomad-public/release/2.1.1/constraint/gnomad.v2.1.1.1of_metrics.by_gene.text.bgz) was downloaded from the gnomAD database website. The observed synonymous variants in the merged dataset was used as baseline and was converted to the expect number of LOFs 364 by multiplying the ratio of the expected number of LOFs and the expected number of synonymous variants from gnomAD. The depletion metric 380 was then calculated (step 378) and verified to be within [0,1]. If less than 0, a 0 is assigned and vice versa. The above may be represented as:

$$depletion_{LOF} = 1 - \frac{\#\ obsLOF}{\#\ expLOF} \tag{3}$$

$$\text{where } \#\ expLOF = \#\ obsSyn * \frac{\#\ expLOF \text{ of } gnomAD}{\#\ expSyn \text{ of } gnomAd}$$

Based on the depletion metric 380 of LOFs, the estimates of selection coefficients of LOFs 390 can be derived (step 388) for each gene using the respective selection-depletion curve 312.

Figure 17:
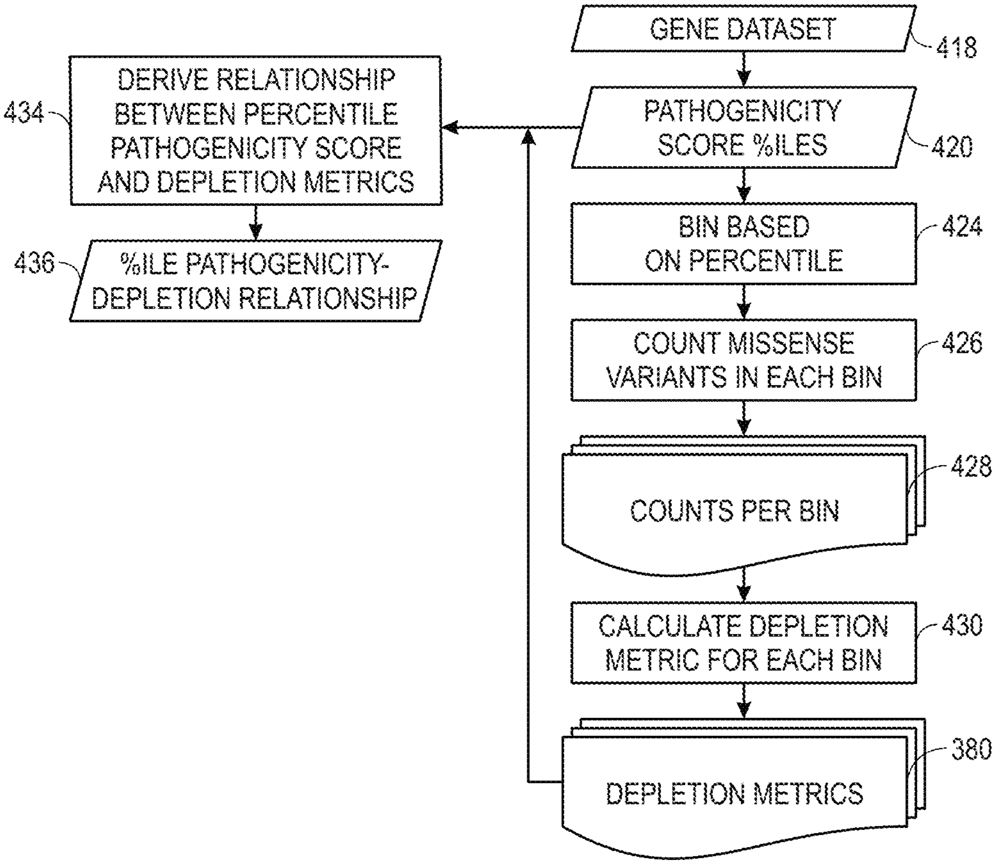
FIG. 17 depicts a sample process flow by which a pathogenicity-depletion relationship may be derived, in accordance with one implementation of the technology disclosed.

With respect to the calculation (step 378) of depletion 380 in missense variants, in one example (illustrated in FIG. 17) of an implementation percentiles 420 of the predicted pathogenicity scores (e.g., PrimateAI or pAI scores) derived for a gene dataset 418 were used to represent all the possible missense variants within each gene. Because pathogenicity scores as described herein measure the relative fitness of variants, it may be expected that pathogenicity scores of missense variants tend to be higher in genes under strong negative selection. Conversely, in genes with moderate selection the scores may be expected to be lower. Thus, it is appropriate to use percentiles 420 of pathogenicity scores (e.g., pAI scores) to avoid the overall effects on genes.

For each gene, the pathogenicity score percentiles 420 (pAI percentiles in the present example) were divided (step 424) into 10 bins (e.g., (0.0, 0.1], (0.1, 0.2], . . . , (0.9, 1.0]), and the number 428 of the observed missense variants falling in each bin were counted (step 426). The depletion metric 380 is calculated 430 similar to that of LOFs, except that a respective depletion metric 380 was computed for each of the 10 bins. The correction factor of missense/synonymous variants from gnomAD was applied, similar as to that used in the calculation of LOF depletion described herein, to the expected number of missense variants in each bin. The above may be represented as:

$$depletion_{Mis} = 1 - \frac{\#\ obsMis \text{ in each bin}}{\#\ expMis/10} \tag{4}$$

$$\text{where } \#\exp Mis = \#\ obsSyn * \frac{\#\ expMis \text{ of } gnomAD}{\#\ expSyn \text{ of } gnomAd}$$

Figure 18:
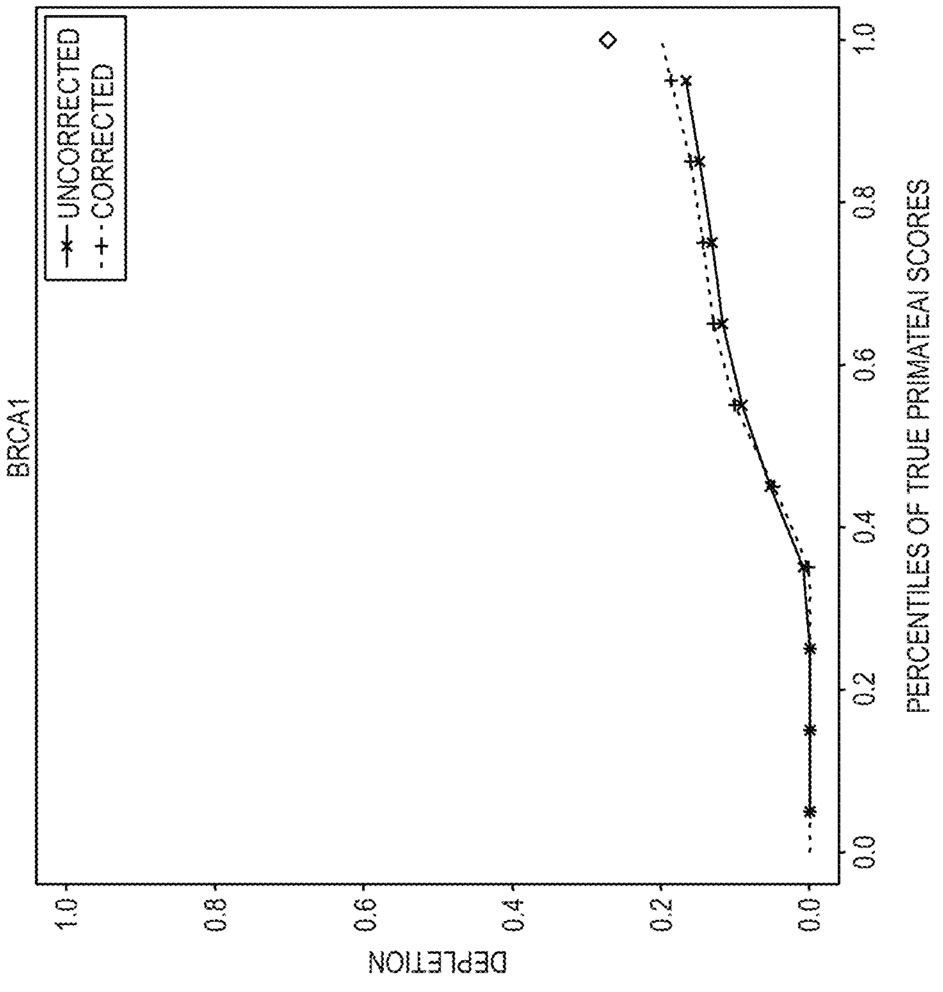
FIG. 18 depicts a plot of pathogenicity score versus depletion for the BRCA1 gene, in accordance with aspects of the present disclosure.
Figure 19:
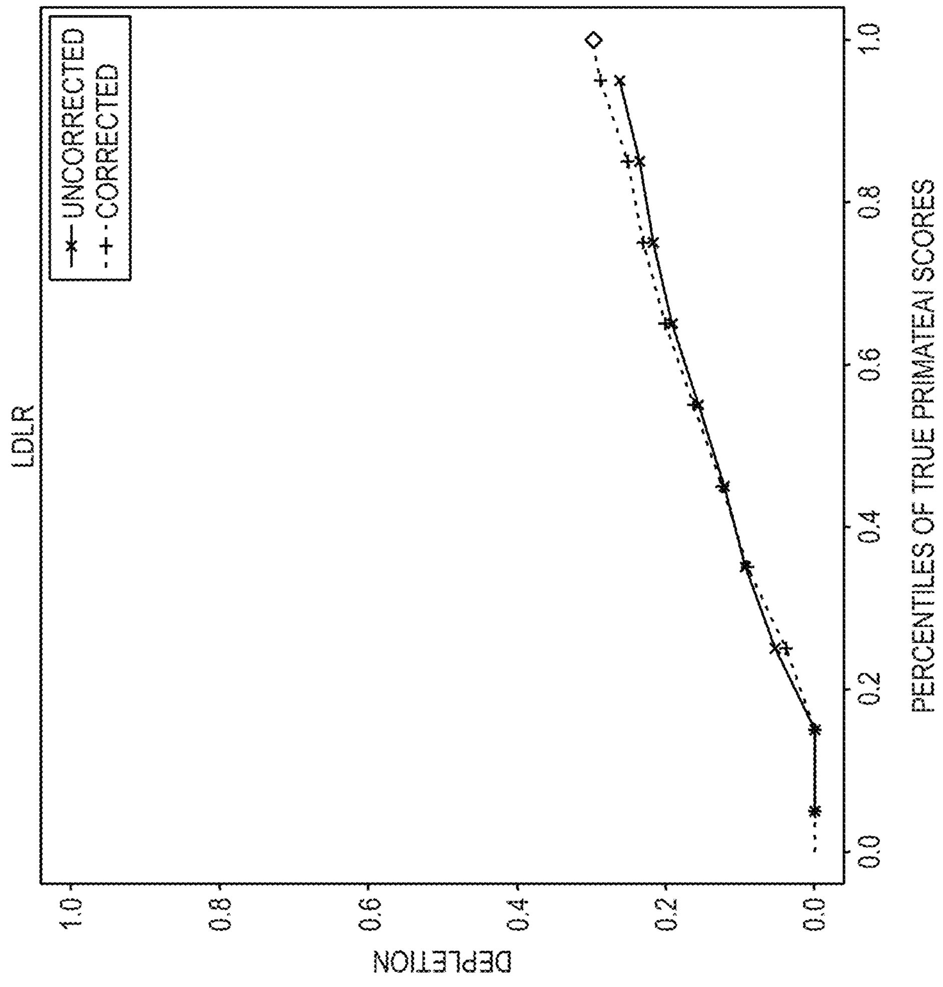
FIG. 19 depicts a plot of pathogenicity score versus depletion for the LDLR gene, in accordance with aspects of the present disclosure.

Based on the depletion of 10 bins within each gene, the relationship 436 between percentiles 420 of pathogenicity scores and the depletion metric(s) 380 may be derived (step 434). In one example, the median percentile of each bin was determined and smooth splines fitted to the median points of the 10 bins. An example of this is shown in FIGS. 18 and 19 with respect to two examples of genes, BRCA1 and LDLR respectively, which show depletion metrics increase in a substantially linear manner with pathogenicity score percentiles.

Based on this methodology, for every possible missense variant, its depletion metric 380 can be predicted based on its pathogenicity percentile score 420 using a gene-specific fitted spline. The selection coefficient 320 of this missense variant can then be estimated using the selection-depletion relationship (e.g., selection-depletion curve 312 or other fitted function).

In addition, the expected number of deleterious rare missense variants and PTVs can be estimated individually. For example, it may be of interest to estimate, on average, the number of deleterious rare variants a normal individual might carry in their coding genome. For this example of an implementation, focus was on rare variants with AF<0.01%. To calculate the expected number of deleterious rare PTVs per individual, it is equivalent to summing up the allele frequencies of PTVs with selection coefficients 320 exceeding a certain threshold, as shown by:

$$E[\#PTV|s > k] = \sum AF|s > k \tag{5}$$

As PTVs include nonsense mutations, splice variants, and frameshifts, computations were made separately for each category. From the results shown in Table 6 below, it may be observed that each individual has about 1.9 rare PTVs with s>0.01 (equal to or worse than a BRCA1 mutation).

TABLE 6

| Expected # of deleterious rare PTVs at different selection coefficient cutoffs | | | | | | |
|---|---|---|---|---|---|---|
| | s >0.2 | s >0.1 | s >0.05 | s >0.02 | s >0.01 | s >0.001 |
| E [# nonsense variants] | 0.0037 | 0.0209 | 0.0754 | 0.3078 | 0.6459 | 0.9959 |
| E [#splice variants] | 0.0032 | 0.0153 | 0.0471 | 0.1639 | 0.3361 | 0.5100 |
| E [#frameshifts] | 0.0234 | 0.0635 | 0.1574 | 0.4944 | 0.9338 | 1.3745 |
| E [#PTVs] | 0.0303 | 0.0996 | 0.2799 | 0.9662 | 1.9159 | 2.8804 |

In addition, the expected number of deleterious rare missense variants were computed by summing up allele frequencies of rare missenses with selection coefficients 320 exceeding different thresholds:

$$E[\#missense|s > k] = \sum AF|s > k \tag{6}$$

From the results shown in Table 7 below, there are about 4 times as many missense variants as PTVs with s>0.01.

TABLE 7

| Expected # of deleterious rare missense variants at different selection coefficient cutoffs | | | | | | |
|---|---|---|---|---|---|---|
| E [# missense variants] | s >0.2 | s >0.1 | s >0.05 | s >0.02 | s >0.01 | s >0.001 |
| gnomAD + Topmed with correction | 0.0022 | 0.0178 | 0.208 | 2.846 | 10.107 | 31.990 |
| gnomAD + Topmed + UK biobank with correction | 0.00067 | 0.010 | 0.146 | 2.336 | 8.989 | 30.868 |
| gnomAD + Topmed + UK biobank without correction | 0.0002 | 0.0035 | 0.0806 | 1.8327 | 8.2948 | 33.0164 |

VI. Estimation of Genetic Disease Prevalence Using Pathogenicity Scores

To promote the adoption and usage of pathogenicity scores of missense variants in clinical settings, the relationship between pathogenicity scores and clinical disease prevalence among those genes of clinical interest was investigated. In particular, methodologies were developed for estimating genetic disease prevalence using various metrics based on pathogenicity scores. Non-limiting examples of two such methodologies based on pathogenicity scores to predict genetic disease prevalence are described herein.

Figure 20:
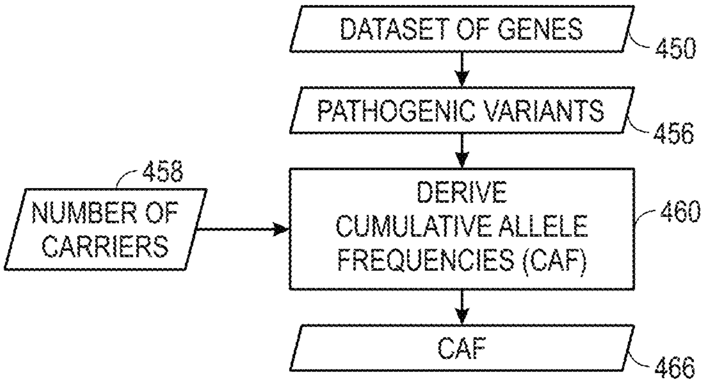
FIG. 20 depicts a sample process flow by which cumulative allele frequency may be derived, in accordance with one implementation of the technology disclosed.

By way of preliminary context in terms of the data employed in this study, the DiscovEHR data referenced herein is a collaboration between the Regeneron Genetics Center and Geisinger Health System that aims to catalyze precision medicine by integrating whole-exome sequencing with clinical phenotypes from longitudinal electronic health records (EHRs) of 50,726 adult participants in Geisinger's MyCode Community Health Initiative. With this in mind, and with reference to FIG. 20, 76 genes (G76) were defined (i.e., dataset of genes 450) that included 56 genes and 25 medical conditions identified in the American College of Medical Genetics and Genomics (ACMG) recommendation for identification and reporting of clinically actionable genetic findings. The prevalence of these potentially pathogenic variants 456, which include those with ClinVar "pathogenic" classification as well as the known and predicted loss-of-function variants, within the G76 genes was evaluated. The cumulative allele frequencies (CAF) 466 of those ClinVar pathogenic variants 456 in each gene were derived (step 460) as discussed herein. Approximate genetic disease prevalence for most of 76 genes was obtained from literature sources.

Figure 22:
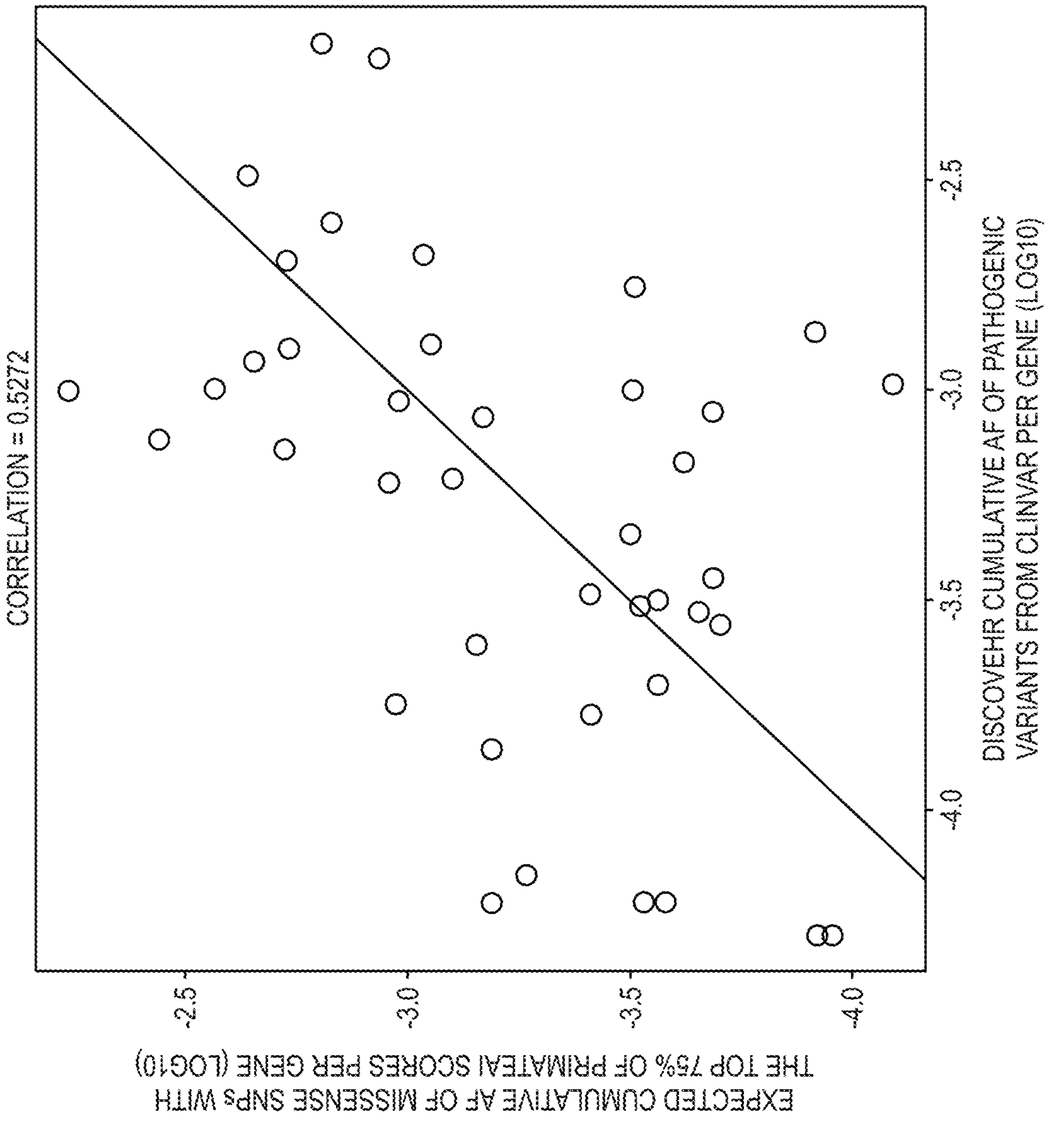
FIG. 22 depicts a plot of expected versus observed cumulative allele frequency, in accordance with aspects of the present disclosure.
Figure 23:
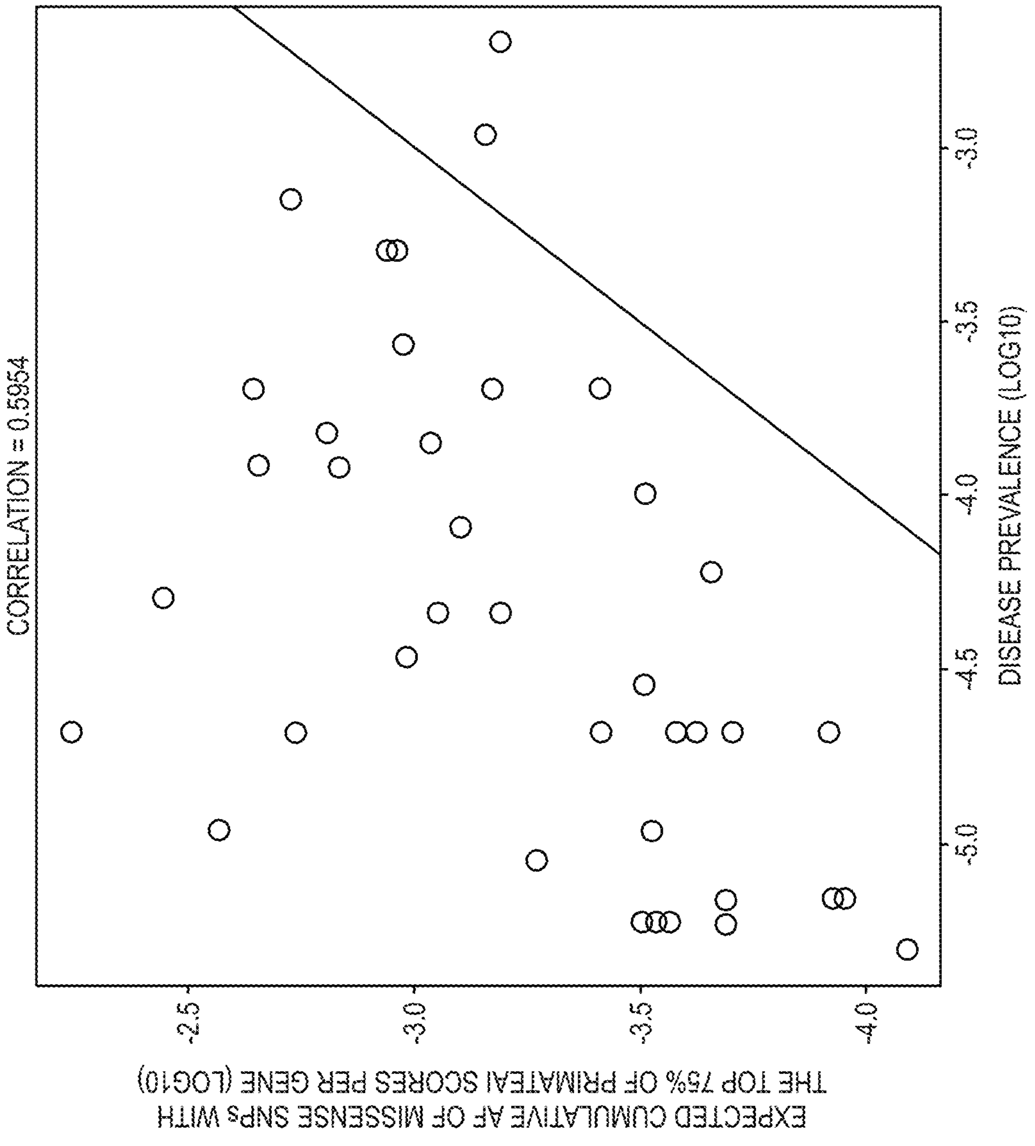
FIG. 23 depicts a plot of expected cumulative allele frequency versus disease prevalence, in accordance with aspects of the present disclosure.

With this context in mind, two examples of approaches based on pathogenicity scores 206 (e.g., PrimateAI or pAI scores) for predicting genetic disease prevalence were developed. In these methodologies, and with reference to FIG. 21, gene-specific pathogenicity score thresholds 212 are employed (decision block 210) to determine whether missense variants 200 of a gene are pathogenic (i.e., pathogenic variants 220) or not (i.e., non-pathogenic variants 476). In one example, cutoffs were defined for predicted deleterious variants if the pathogenicity scores 206 were greater than the 75th percentile of pathogenicity scores in a specific gene, though other cutoffs could be employed as appropriate. The genetic disease prevalence metric was defined as the expected cumulative allele frequencies (CAF) 480 of those predicted deleterious missense variants, as derived at step 478. As shown in FIG. 22, the Spearman correlation of this metric with DiscovEHR cumulative AF of Clinvar pathogenic variants is 0.5272. Similarly, FIG. 23 illustrates that the Spearman correlation of this metric with disease prevalence is 0.5954, implying good correlation. Thus the genetic disease prevalence metric (i.e., expected cumulative allele frequencies (CAF) of those predicted deleterious missense variants) can serve as a predictor of genetic disease prevalence.

Figure 21:
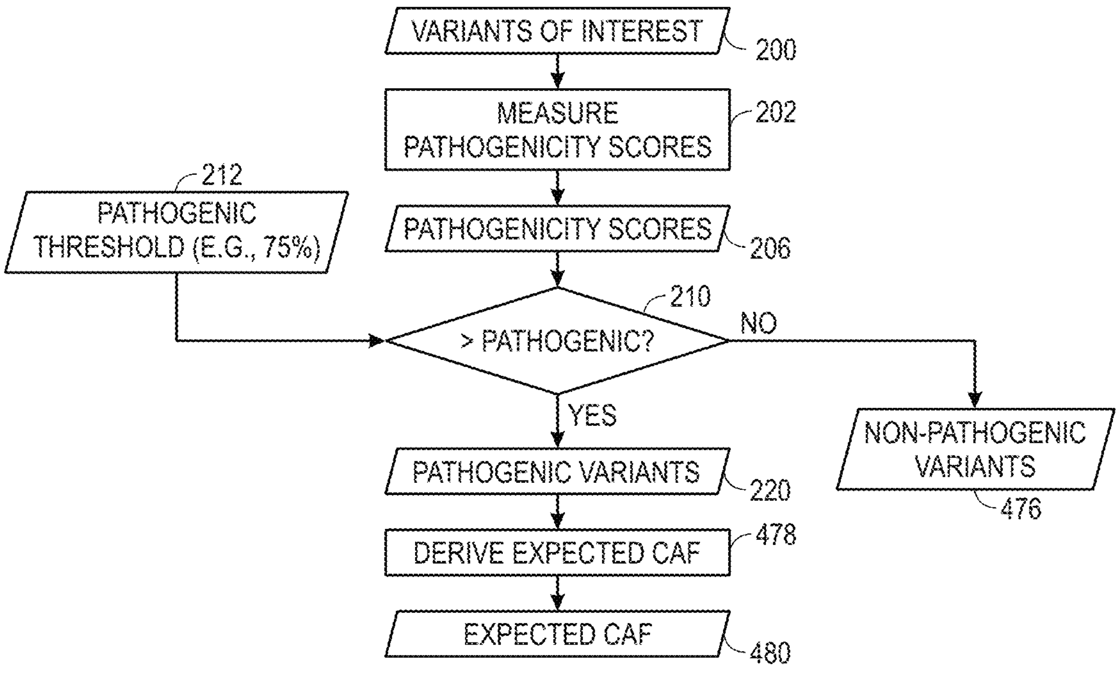
FIG. 21 depicts a generalized sample process flow by which an expected cumulative allele frequency may be derived, in accordance with one implementation of the technology disclosed.
Figure 24:
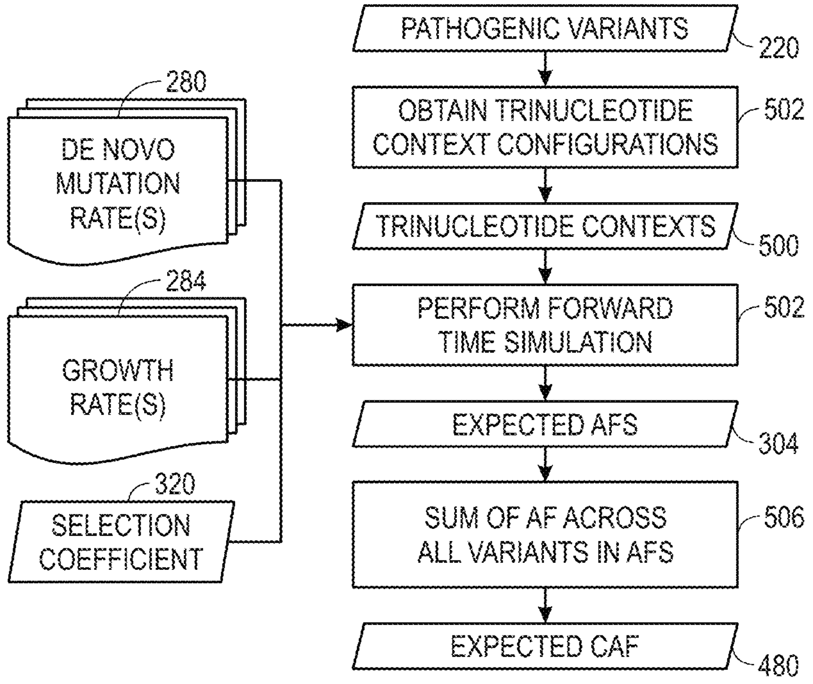
FIG. 24 depicts a first sample process flow by which an expected cumulative allele frequency may be derived, in accordance with one implementation of the technology disclosed.

With respect to calculating this genetic disease prevalence metric for each gene, depicted as step 478 of FIG. 21, two different approaches were evaluated. In a first methodology, and with reference to FIG. 24 the trinucleotide context configurations 500 of the list of deleterious missense variants 220 are initially obtained (step 502). In the present context, this may correspond to obtaining all of the possible missense variants, where these pathogenic variants 220 are those having pathogenicity scores 206 exceeding the 75th percentile threshold (or other suitable cutoff) in that gene.

For each trinucleotide context 500, the forward-time simulation, as described herein, is performed (step 502) to generate the expected (i.e., simulated) allele frequency spectrum (AFS) 304, assuming a selection coefficient 320 equal to 0.01 and using the de novo mutation rates 280 for that trinucleotide context. In one implementation of this methodology the simulation simulated 100,000 independent sites among ~400K chromosomes (~200K samples). Thus, the expected AFS 304 for a specific trinucleotide context 500 in such a context is the simulated AFS/100,000*the occurrence of the trinucleotide in the list of deleterious variants. Summing up across the 192 trinucleotides produce the expected AFS 304 for the gene. The genetic disease prevalence metric of a specific gene (i.e., expected CAF 480) in accordance with this approach is defined as the sum (step 506) of simulated rare allele frequencies (i.e., AF≤0.001) in the expected AFS 304 for the gene.

Figure 25:
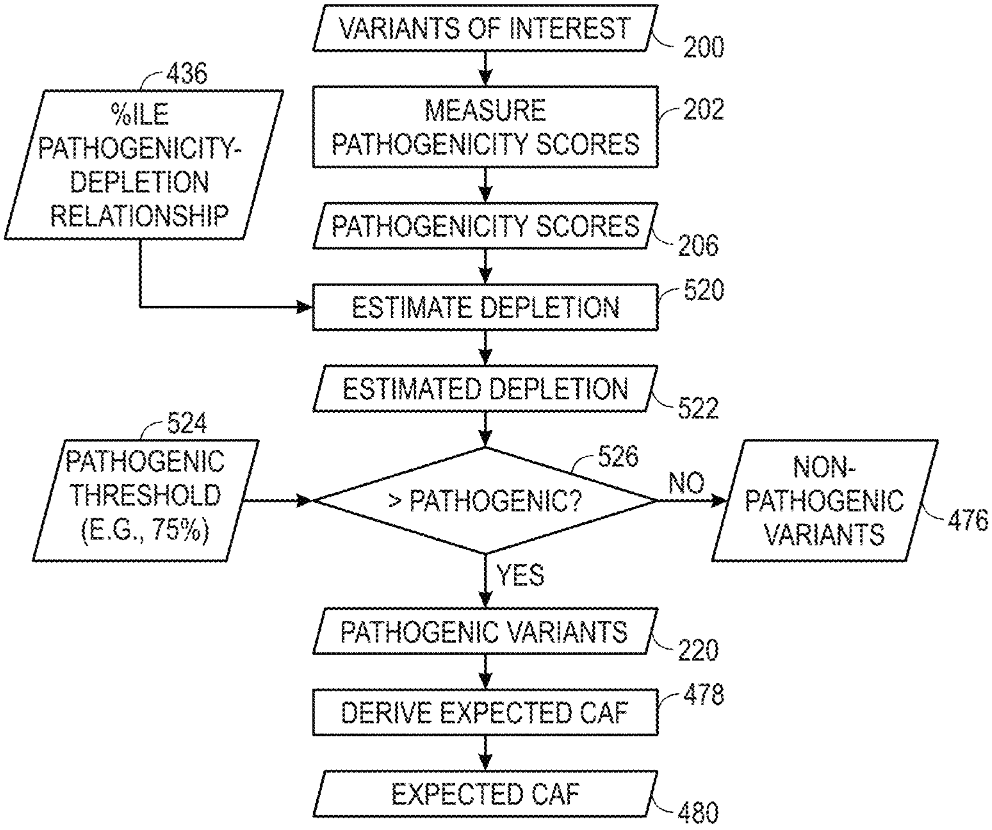
FIG. 25 depicts a second sample process flow by which an expected cumulative allele frequency may be derived, in accordance with one implementation of the technology disclosed.

The genetic disease prevalence metric as derived in accordance with the second methodology is similar to that derived using the first methodology, but differs in the definition of the list of deleterious missense variants. In accordance with the second methodology, and with reference to FIG. 25, the pathogenic variants 220 are defined as the predicted deleterious variants per gene if their estimated depletion is ≥75% of depletion of protein-truncating variants (PTV) in that gene, as discussed herein. By way of example, and as shown in FIG. 25, in this context a pathogenicity score 206 may be measured (step 202) for variant(s) of interest 200. The pathogenicity score(s) 206 may be used to estimate (step 520) depletion 522 using a pre-determined percentile pathogenicity-depletion relationship 436, as discussed herein. The estimated depletion 522 may then be compared (decision block 526) to a depletion threshold or cutoff 524 to separate non-pathogenic variants 476 from those deemed to be pathogenic variants 220. Once the pathogenic variants 220 are determined, processing may proceed as discussed above at step 478 to derive an expected CAF 480.

Figure 26:
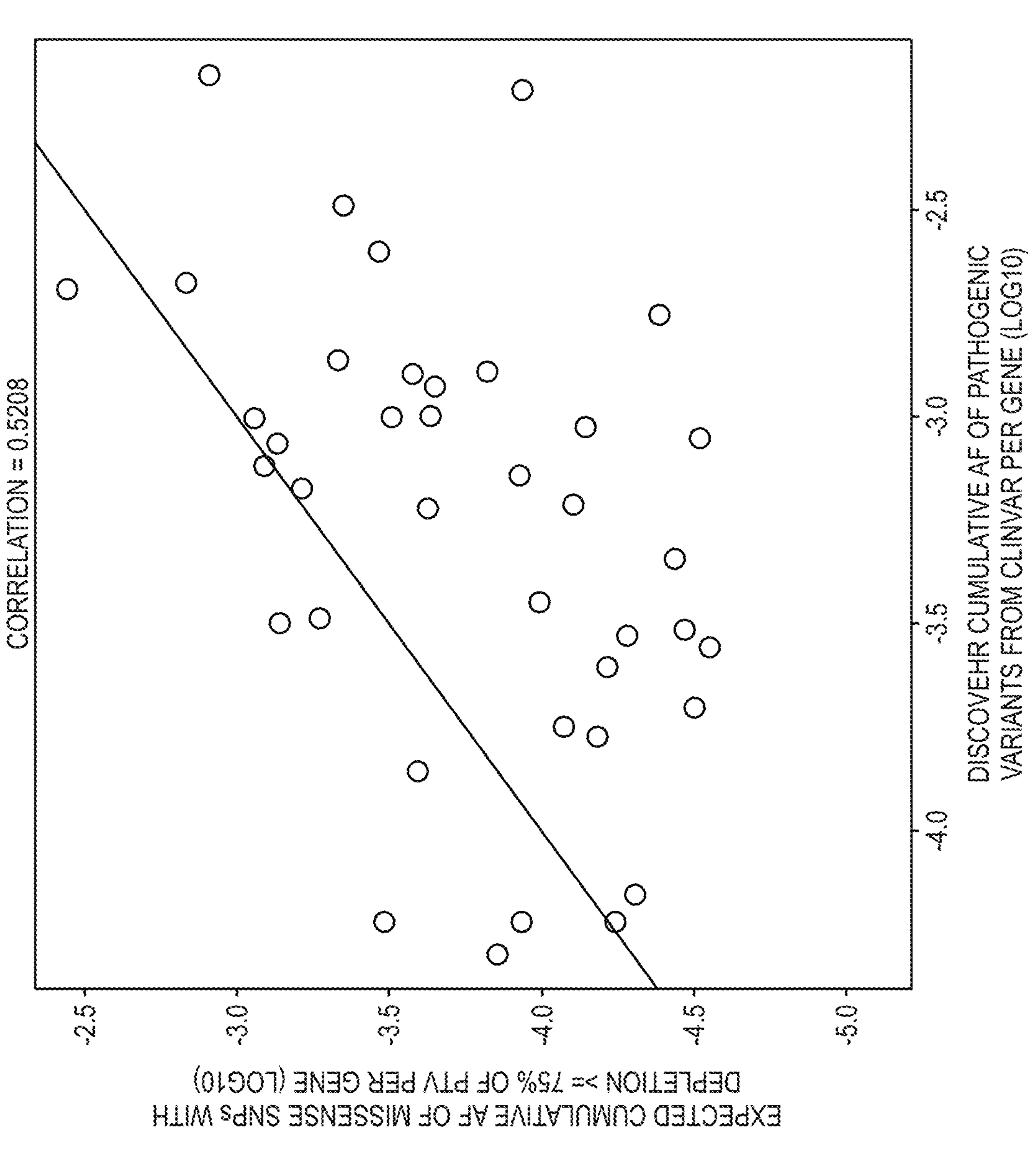
FIG. 26 depicts a plot of expected versus observed cumulative allele frequency, in accordance with aspects of the present disclosure.
Figure 27:
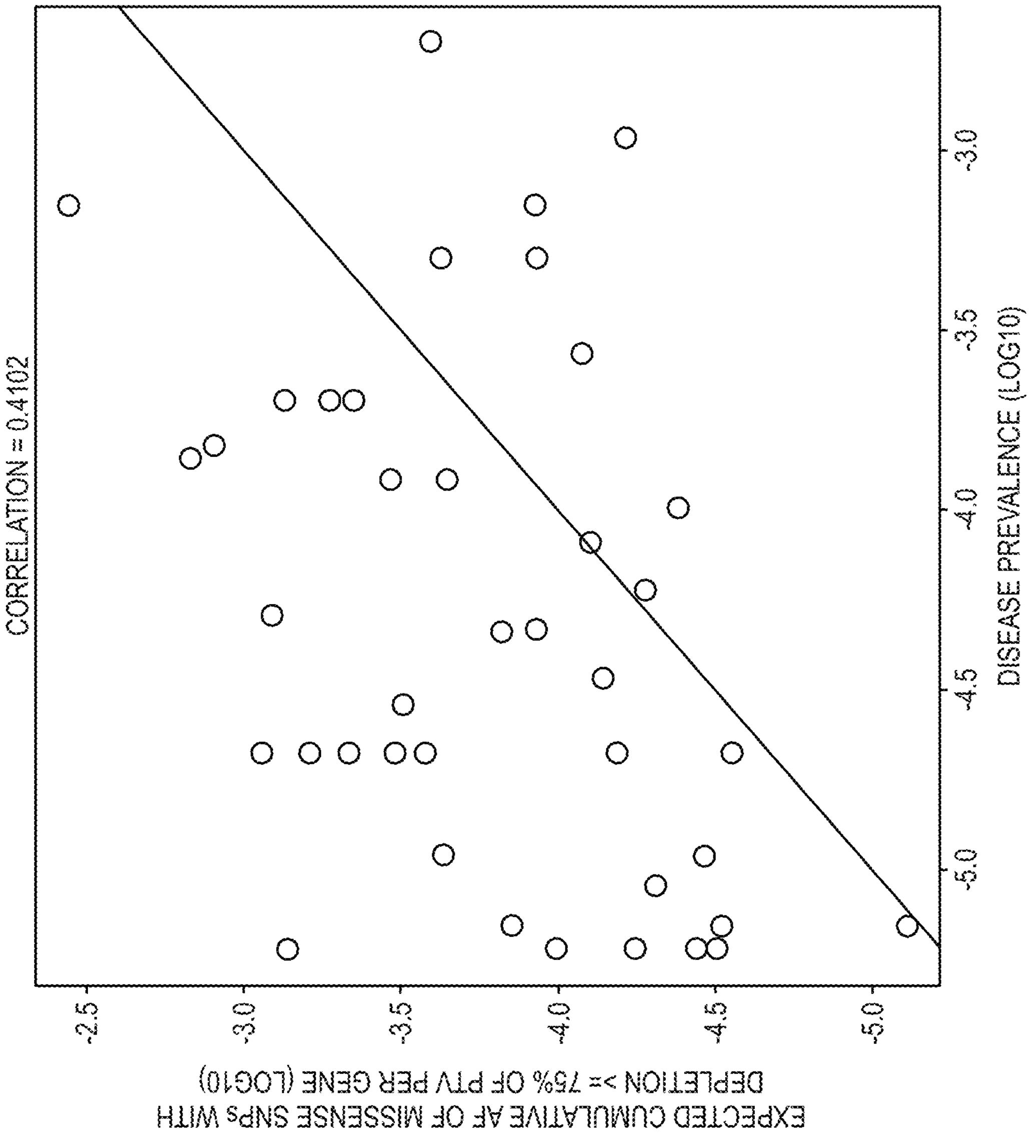
FIG. 27 depicts a plot of expected cumulative allele frequency versus disease prevalence, in accordance with aspects of the present disclosure.

With respect to the genetic disease prevalence metric as derived using this second methodology, FIG. 26 illustrates that the Spearman correlation of the genetic disease prevalence, calculated in accordance with the second methodology, with DiscovEHR cumulative AF of Clinvar pathogenic variants is 0.5208. Similarly, FIG. 27 shows the Spearman correlation of the genetic disease prevalence metric, calculated in accordance with the second methodology, with disease prevalence is 0.4102, implying good correlation. Thus the metric as calculated using the second methodology may also serve as the predictor of genetic disease prevalence.

VII. Recalibration of Pathogenicity Scores

As described herein, pathogenicity scores generated in accordance with the present teachings are derived using neural networks trained primarily based on DNA flanking sequences around variants, conservation among species, and protein secondary structures. However, the variation associated with pathogenicity scores (e.g., PrimateAI scores) can be large (e.g., about 0.15). In addition, certain implementations of the generalized model discussed herein for calculating pathogenicity scores do not utilize the information of observed allele frequencies in human population during training. In certain circumstances, some variants with high pathogenicity scores might appear to have allele counts >1, implying that there is a need to penalize these pathogenicity scores based on allele counts. With this in mind, it may be useful to recalibrate pathogenicity scores to address such circumstances. In one example embodiment discussed herein, a recalibration approach may focus on the percentiles of pathogenicity scores of variants, as these may be more robust and less affected by selection pressure exerted on the whole genes.

Figure 28:
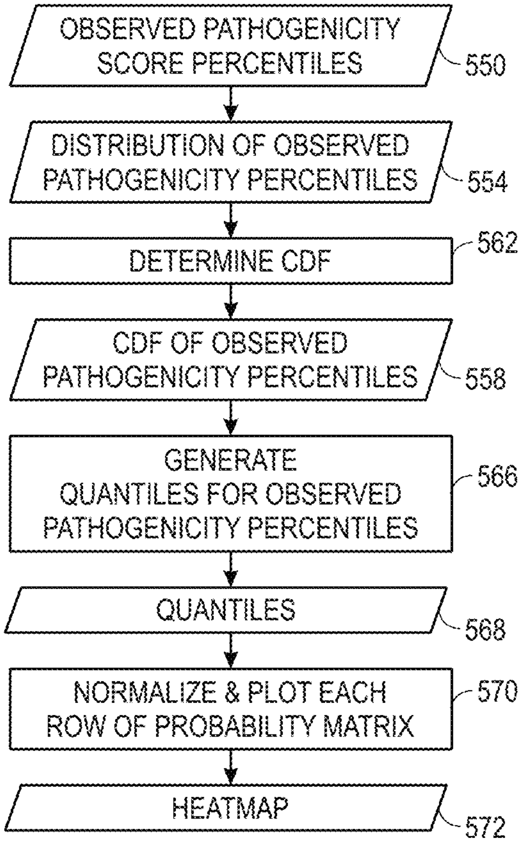
FIG. 28 depicts a sample process flow relating aspects of a recalibration approach to a pathogenicity scoring process, in accordance with one implementation of the technology disclosed.

With this in mind, and with reference to FIG. 28, in one example of a recalibration approach, the true pathogenicity percentiles are modeled so as to allow one to assess and account for the noise in the observed pathogenicity score percentiles 550. In this modeling process, it may be assumed that the true pathogenicity percentiles are discrete-uniformly distributed over (0,1] (e.g., they take 100 values, [0.01, 0.02, . . . , 0.99, 1.00]). The observed pathogenicity score percentiles 550 may be assumed to center at the true pathogenicity score percentiles with some noise term which follows normal distribution with standard deviation 0.15:

$$obsAI \sim trueAI + e,\ e \sim N(0, sd = 0.15) \tag{7}$$

Figure 29:
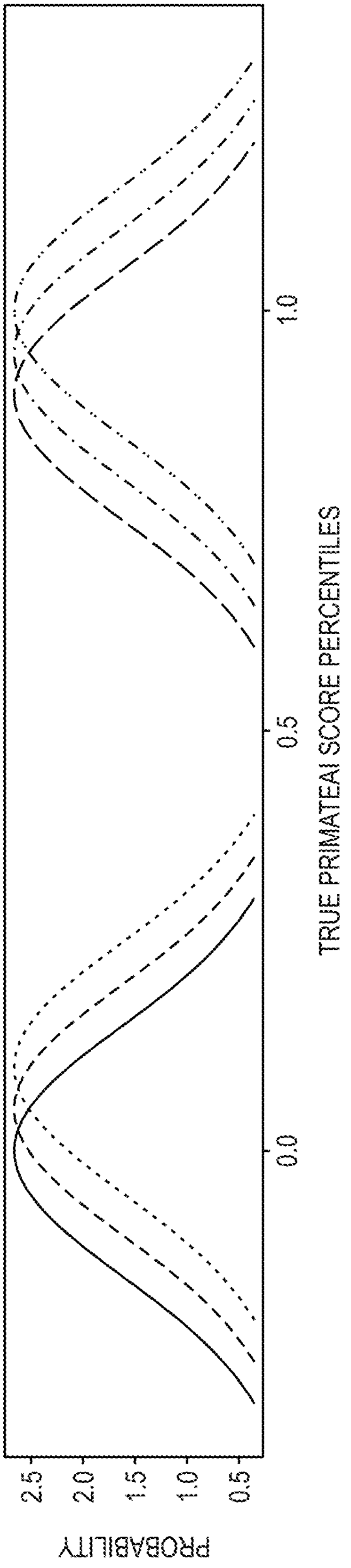
FIG. 29 depicts a distribution of pathogenicity score percentiles versus probability, in accordance with aspects of the present disclosure.
Figure 30:
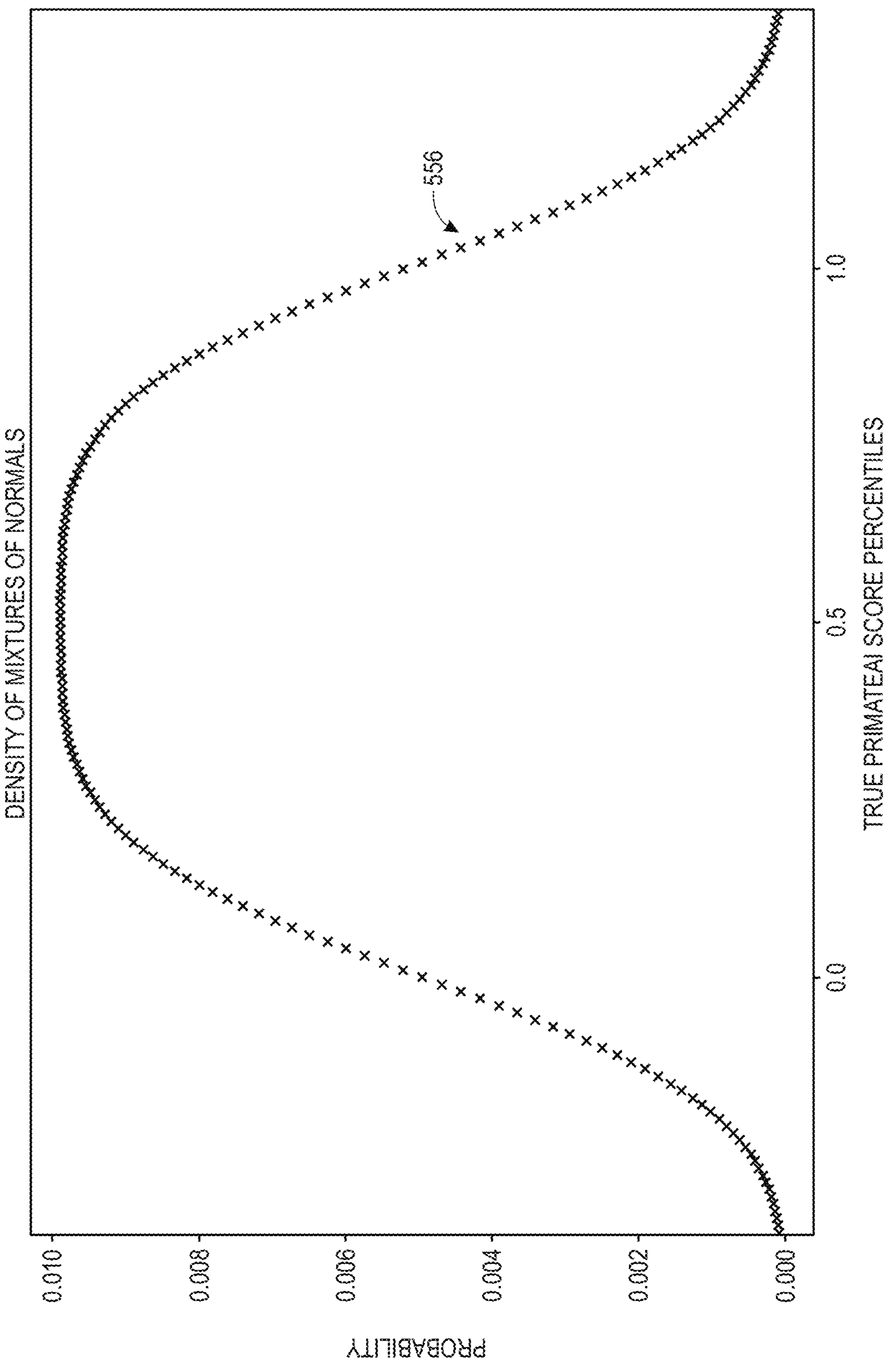
FIG. 30 depicts a density plot of a discrete uniform distribution of observed pathogenicity score percentiles overlaid with Gaussian noise in accordance with aspects of the present disclosure.
Figure 31:
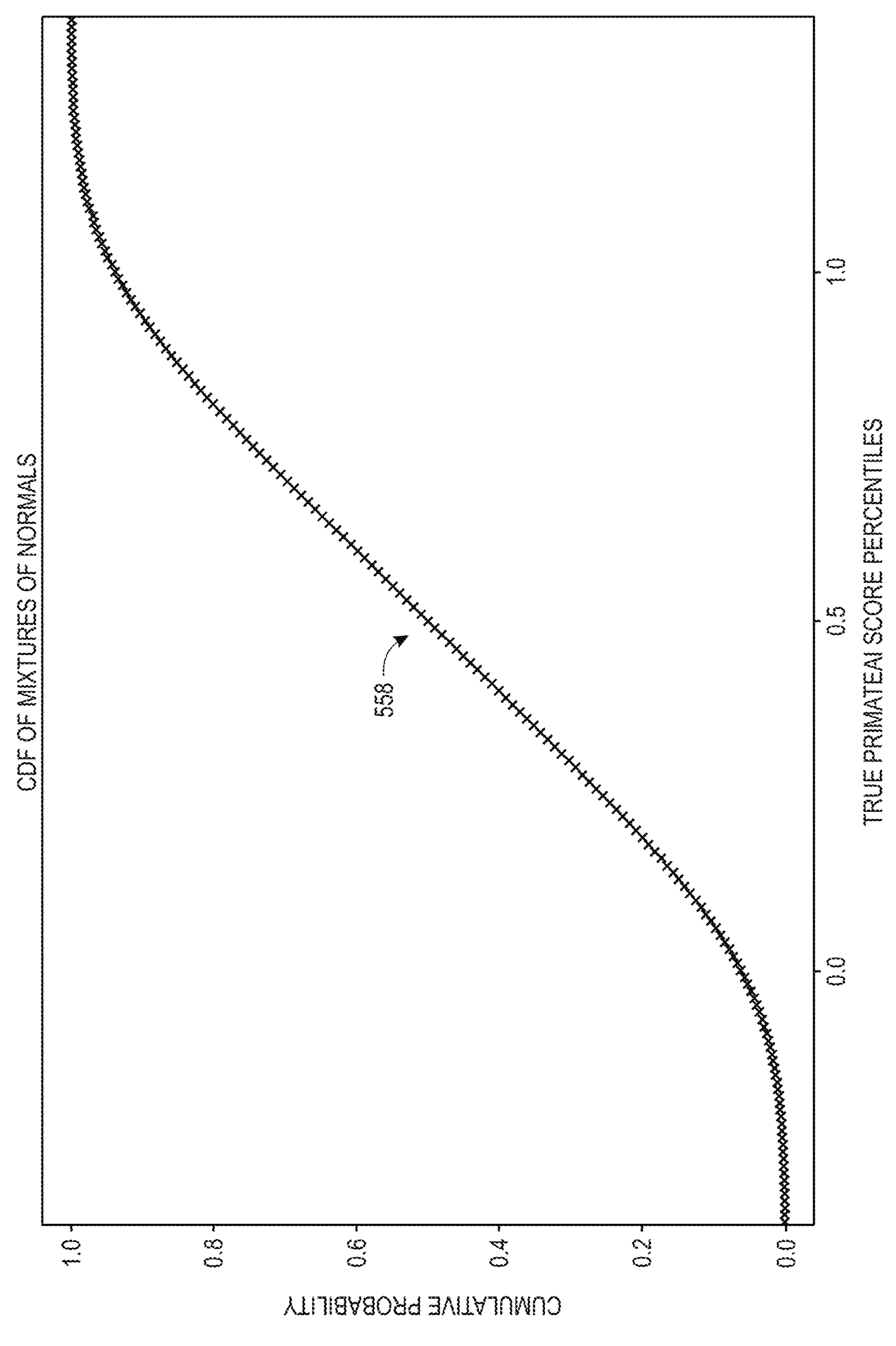
FIG. 31 depicts the cumulative distribution function of a discrete uniform distribution of observed pathogenicity score percentiles overlaid with Gaussian noise in accordance with aspects of the present disclosure.

The distribution 554 of observed pathogenicity score percentiles 550 in this context is the discrete uniform distribution of true pathogenicity score percentiles overlaid with Gaussian noise, as shown in FIG. 29, where each line represents a normal distribution centered at each value of true pathogenicity score percentiles. The density plot of this discrete uniform distribution 556 of observed pathogenicity score percentiles overlaid with Gaussian noise is shown in FIG. 30 and its cumulative distribution function (CDF) 558, determined at step 562, is shown in FIG. 31. From this CDF 558, the cumulative probability is divided into 100 intervals and quantiles 568 are generated (step 566) for the observed pathogenicity score percentiles 550.

Figure 32:
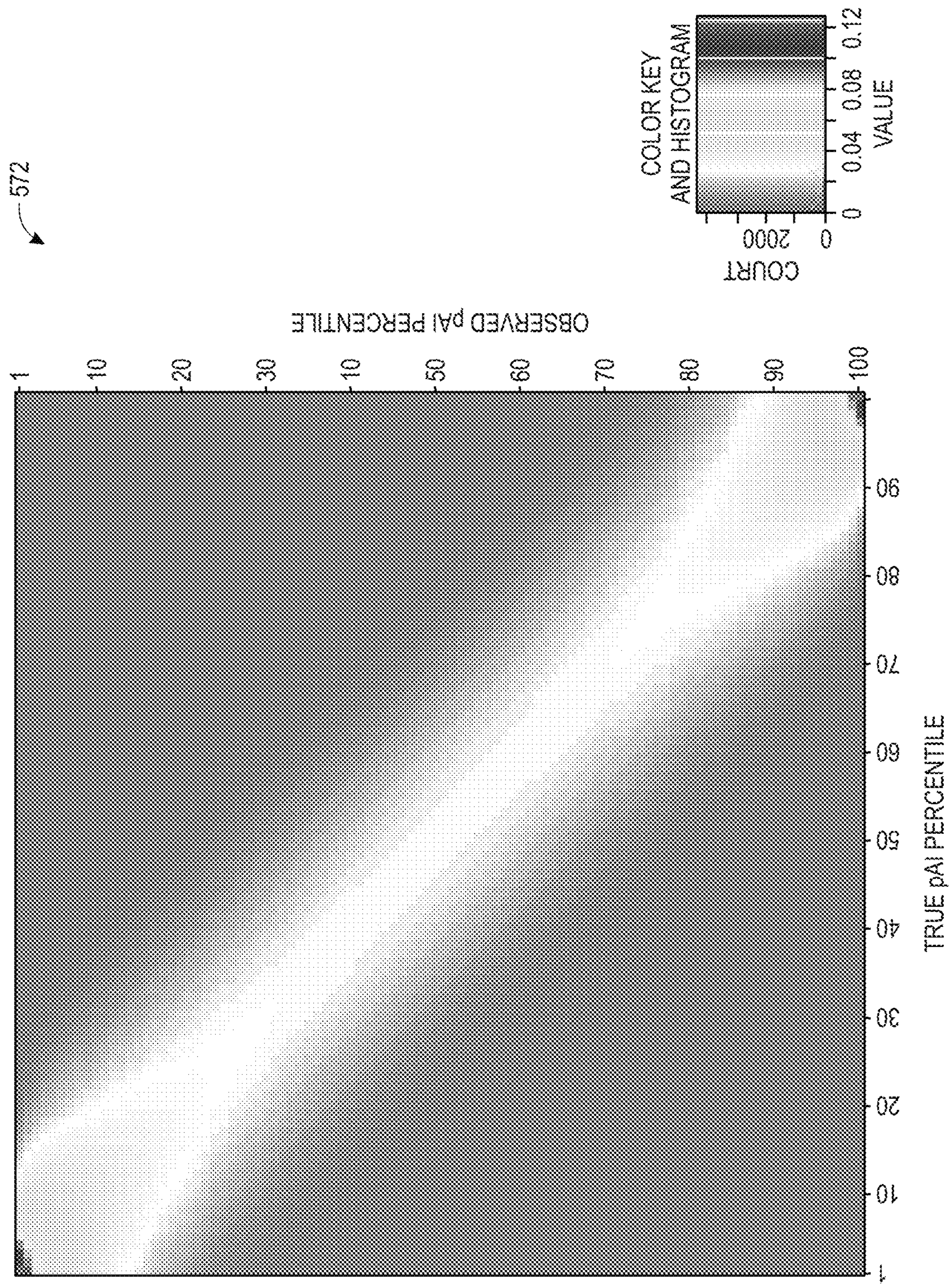
FIG. 32 depicts via a heatmap, the probability that a variant with a true pathogenicity score percentile (x-axis) falls into the observed pathogenicity score percentile interval (y-axis), in accordance with aspects of the present disclosure.

To visualize the probability that a variant with a true pathogenicity score percentile (x-axis in FIG. 32) falls into the observed pathogenicity score percentile interval (y-axis), each row of this 100×100 probability matrix may be normalized to sum to one and the result plotted (step 570) as a heatmap 572 (FIG. 32). Each point on the heatmap 572 measures the probability that a variant within the observed pathogenicity score percentile 550 interval actually comes from a true pathogenicity score percentile (i.e., the probability that a variant with a true pathogenicity score percentile (x-axis) falls into the observed pathogenicity score percentile interval (y-axis)).

Figure 33:
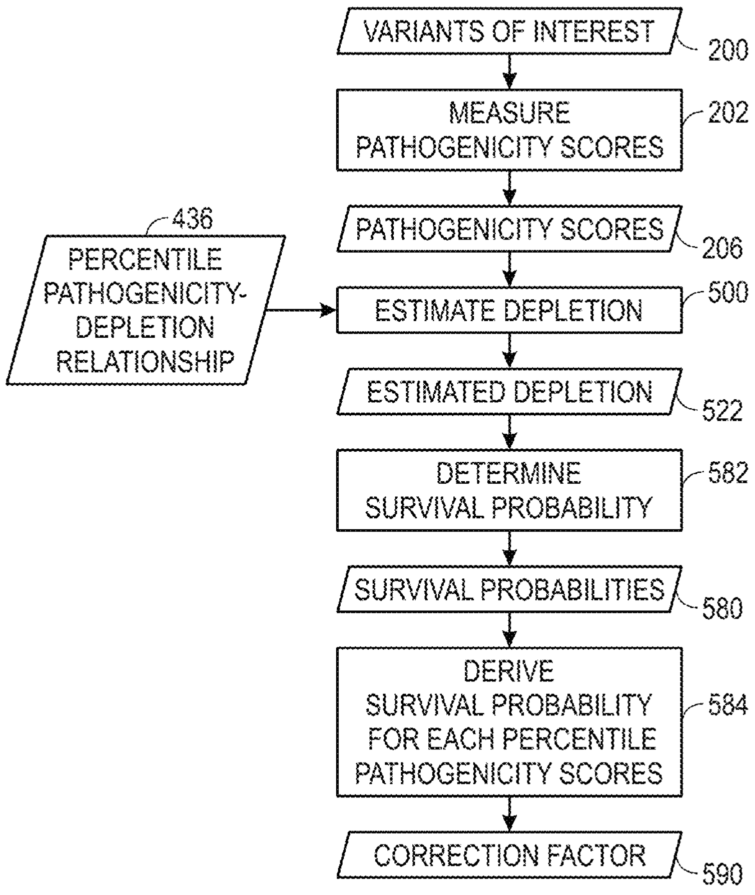
FIG. 33 depicts a sample process flow of steps in determining a correction factor, in accordance with one implementation of the technology disclosed.

Turning to FIG. 33, for missense variants, the depletion metric 522 for each of 10 bins in each gene was determined using the methodologies described herein. In this example, and as discussed elsewhere herein, pathogenicity scores 206 may be calculated (step 202) for the variants of interest 200 as part of the binning process. The respective pathogenicity scores 206 may in turn be used to estimate (step 520) depletion 522 based on a pre-determined percentile pathogenicity score-depletion relationship 436.

Figure 34:
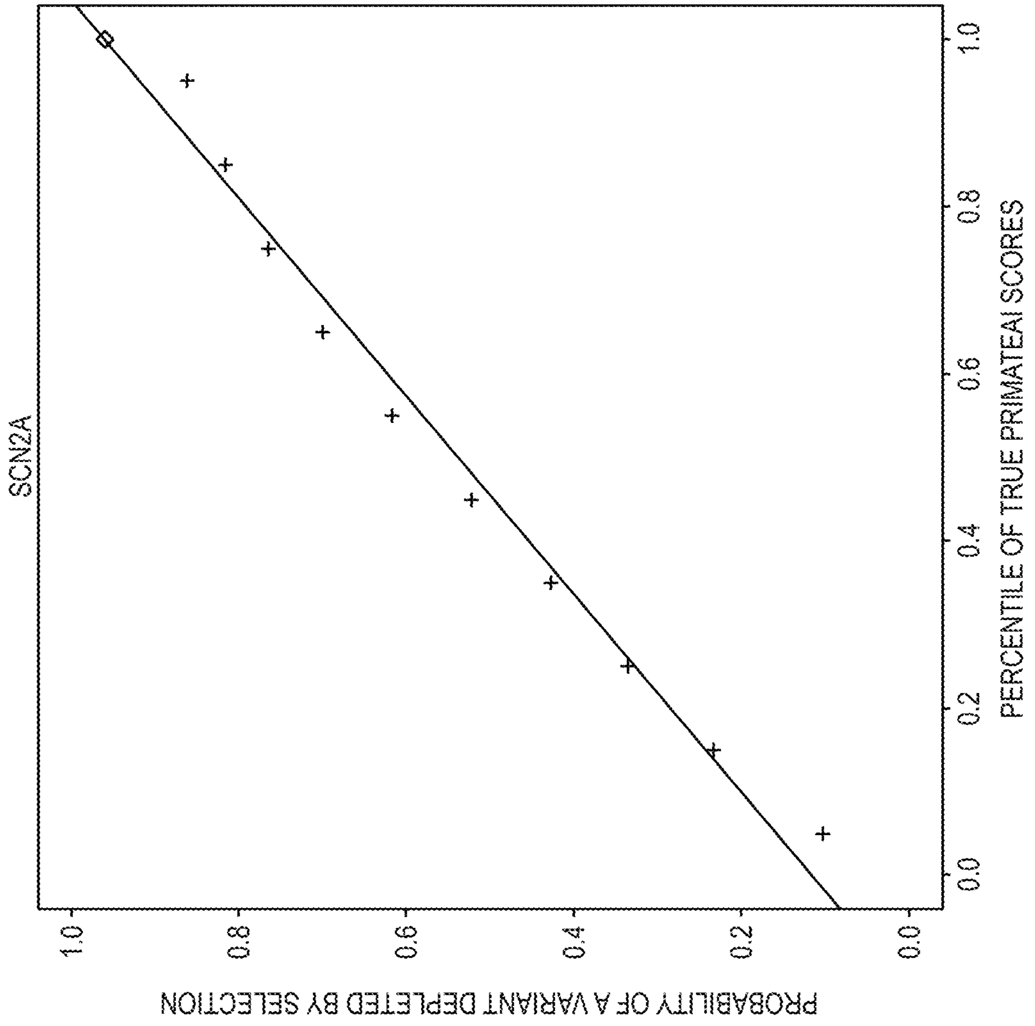
FIG. 34 depicts depletion probabilities across the percentiles of 10 bins for missense variants of the SCN2A gene, in accordance with aspects of the present disclosure.
Figure 35:
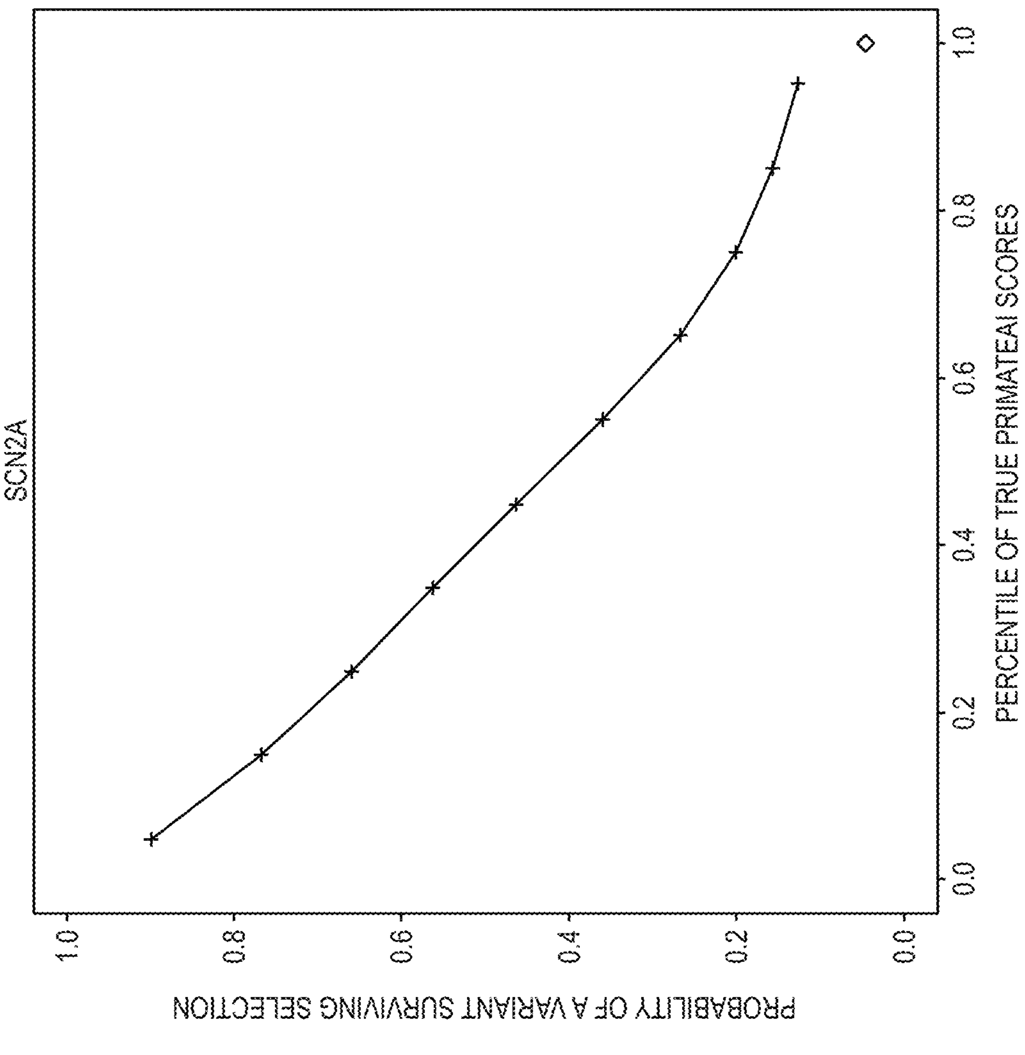
FIG. 35 depicts the survival probabilities across the percentiles of 10 bins for missense variants of the SCN2A gene, in accordance with aspects of the present disclosure.

This depletion metric 522 measures the probability that a variant falling within each bin might be removed by purifying selection. An example of this is shown in FIGS. 34 and 35 with respect to the gene SCN2A. In particular, FIG. 34 depicts the depletion probabilities across the percentiles of 10 bins for missense variants of the SCN2A gene. The probability of a variant surviving the selection may be defined as (1—depletion), denoted as the survival probability 580 and determined at step 582. If this probability is less than 0.05 it may be set to 0.05. FIG. 35 depicts the survival probabilities 580 across the percentiles of 10 bins for missense variants of the SCN2A gene. In both figures, the depicted diamond at 1.0 on the x-axis represent PTVs.

In accordance with one implementation, a smooth spline was fitted (step 584) to the survival probability vs. the median pathogenicity score percentile of each bin across the bins (e.g., 10 bins) and produced the survival probability for each percentile of pathogenicity scores. In accordance with this approach, this constitutes a survival probability correction factor 590, implying that the higher the percentile of pathogenicity scores 206, the less chance the variant survives purifying selection. In other implementations, other techniques may be employed, such as interpolation, in place of fitting a smooth spline. High pathogenicity scores 206 of those observed variants may then be penalized or corrected in accordance with this correction factor 590.

Figure 36:
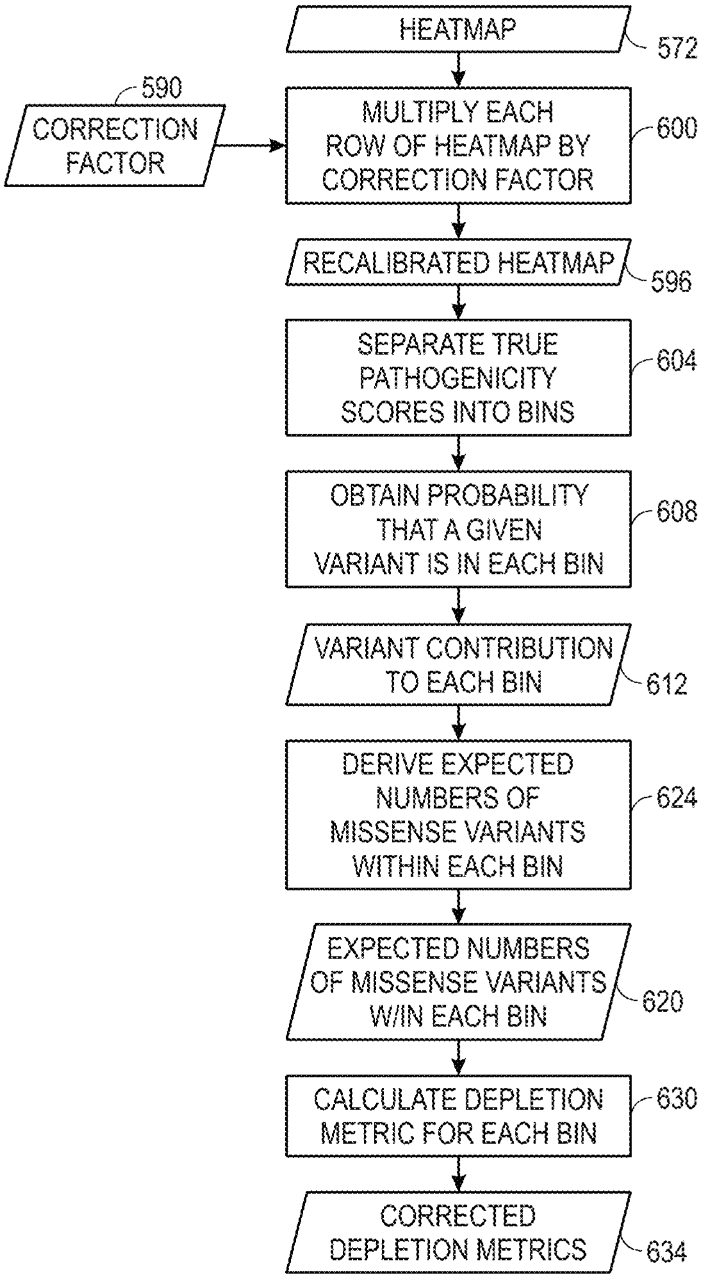
FIG. 36 depicts a sample process flow of steps in determining a corrected depletion metric, in accordance with one implementation of the technology disclosed.
Figure 37:
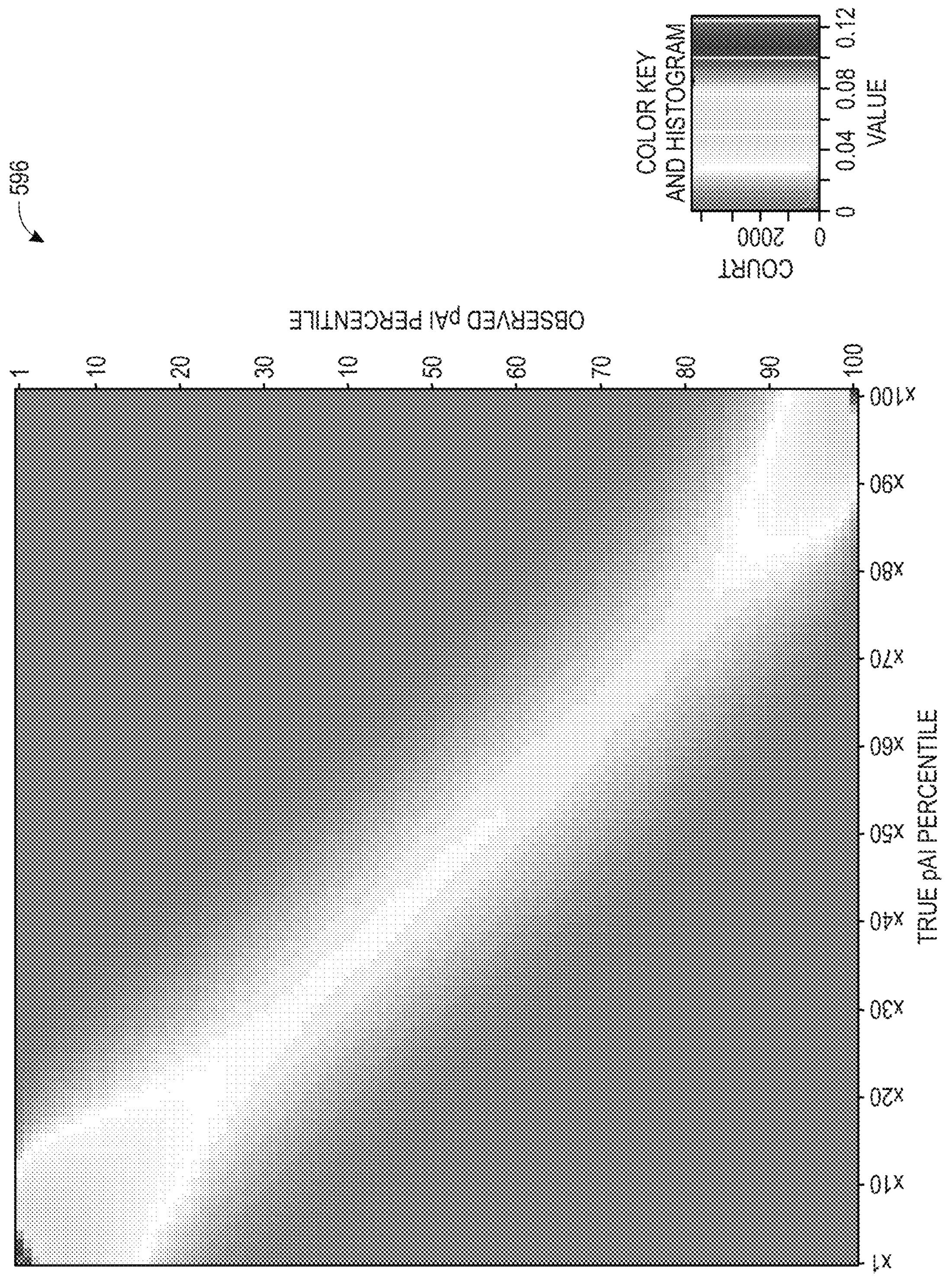
FIG. 37 depicts a corrected or recalibrated heatmap conveying the probability that a variant with a true pathogenicity score percentile (x-axis) falls into the observed pathogenicity score percentile interval (y-axis), in accordance with aspects of the present disclosure.

With the preceding in mind, and turning to FIG. 36, the survival probability correction factor 590 may be employed to perform a recalibration. By way of example, and in the context of a probability matrix, which may be visualized as a heatmap 572 as previously illustrated, for a specific gene, each row of the heatmap 572 (e.g., a probability matrix with a dimension 50×50, 100×100, and so forth) is multiplied (step 600) by the respective survival probability correction factor 590 (e.g., a vector of 100 values) to reduce the values of heatmap 572 by the expected depletion of that gene. Each row of the heatmap is then recalibrated to sum to 1. The recalibrated heat map 596 may then be plotted and displayed, as shown in FIG. 37. The recalibrated heatmap 596 in this example displays the true pathogenicity score percentiles on the x-axis and the recalibrated observed pathogenicity score percentile is on y-axis.

The true pathogenicity score percentiles were divided (step 604) into bins (i.e., merge 1%-10% (the first 10 columns of the recalibrated heatmap 596) into a first bin), 11%-20% (the next 10 columns of the recalibrated heatmap 596) into second bin, . . . , etc.), which represent the probability a variant might come from each of the true pathogenicity score percentile bins. For variants of that gene having an observed pathogenicity score percentile (e.g. x %, corresponding to the x-th row of the recalibrated heatmap 596), the probability that this variant might fall within each of the true pathogenicity score percentile bins (e.g., 10 bins) can be obtained (step 608). This may be denoted as the variant contribution 612 to each bin.

Figure 38:
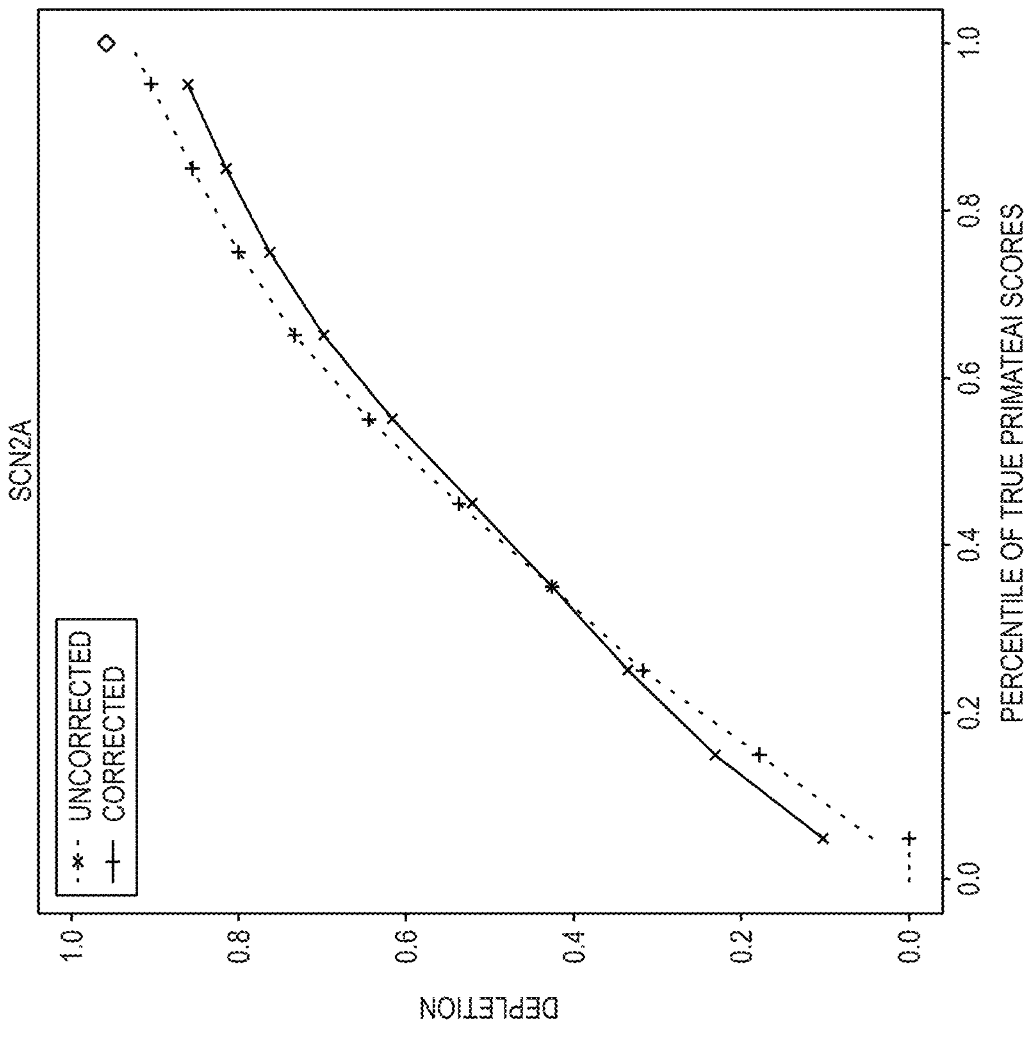
FIG. 38 depicts a plot of corrected depletion metrics for each pathogenicity score percentile bin, in accordance with aspects of the present disclosure.

In this example, the expected number of missense variants 620 within each of the bins (e.g., 10 bins) (derived at step 624) is the sum of the variant contributions to that bin across all the observed missense variants in the respective gene. Based on this expected number of missense variants 620 falling within each of the bins for a gene, the depletion formula for missense variants discussed herein can be used to calculate (step 630) the corrected depletion metric 634 for each missense bin. This is illustrated in FIG. 38, in which an example of corrected depletion metrics for each percentile bin is plotted. In particular, FIG. 38 depicts a comparison of recalibrated depletion metrics versus the original depletion metrics in gene SCN2A. The diamond plotted at 1.0 on the x-axis indicates the depletion of PTVs.

In this manner of recalibrating the pathogenicity scores 206, the noise distribution in percentiles of pathogenicity scores 206 is modeled and the noise in predicted depletion metrics 522 reduced. This may help mitigate the effects of noise on the estimation of selection coefficients 320 in missense variants as discussed herein.

VIII. Neural Network Primer

Neural Networks

In the preceding discussion, various aspects of neural network architecture and use are referenced in the context of a pathogenicity classification or scoring network. While extensive knowledge of these various aspects of neural network design and use are not believed to be necessary for those wishing to understand and employ a pathogenicity classification network as discussed herein, for the benefit of those wishing additional detail, the following neural network primer is provided by way of additional reference.

With this in mind, the term "neural network" in a general sense may be understood to be a computational construct that is trained to receive a respective output and, based upon its training generate an output, such as a pathogenicity score, in which the input is modified, classified, or otherwise processed. Such a construct may be referred to as a neural network due to being modeled after a biological brain, with different nodes of the construct being equated to "neurons", which may be interconnected with a wide range of other nodes so as to allow for complex potential interconnections between nodes. In general, a neural network may be considered a form of machine learning, as the pathways and associated nodes are typically trained by way of example (e.g., using sample data where the inputs and outputs are known or where a cost function can be optimized) and may learn or evolve over time as the neural network is used and its performance or outputs are modified or retrained.

Figure 39:
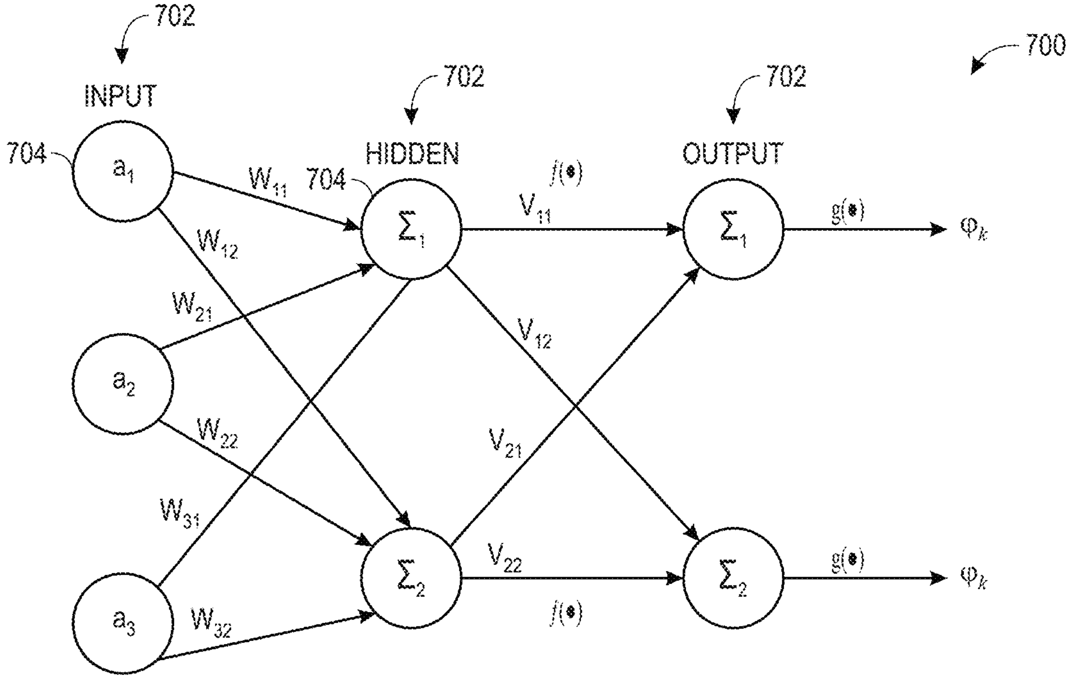
FIG. 39 depicts one implementation of a feed-forward neural network with multiple layers, in accordance with aspects of the present disclosure.

With this in mind and by way of further illustration, FIG. 39 depicts a simplified view of an example of a neural network 700, here a fully connected neural network 700 with multiple layers 702. As noted herein and as shown in FIG. 39, a neural network 700 is a system of interconnected artificial neurons 704 (e.g., $a_1$, $a_2$, $a_3$) that exchange messages between each other. The illustrated neural network 700 has three inputs, two neurons in the hidden layer and two neurons in the output layer. The hidden layer has an activation function f(•) and the output layer has an activation function g(•). The connections have associated numeric weights (e.g., $w_{11}$, $w_{21}$, $w_{12}$, $w_{31}$, $w_{22}$, $w_{32}$, $v_{11}$, $v_{22}$) that are tuned during the training process so that a properly trained network responds correctly when fed an input for which it has been trained to process. The input layer processes the raw input, the hidden layer processes the output from the input layer based on the weights of the connections between the input layer and the hidden layer. The output layer takes the output from the hidden layer and processes it based on the weights of the connections between the hidden layer and the output layer. In one context, the network 700 includes multiple layers of feature-detecting neurons. Each layer has many neurons that respond to different combinations of inputs from the previous layers. These layers may be constructed so that the first layer detects a set of primitive patterns in the input image data, the second layer detects patterns of patterns, the third layer detects patterns of those patterns, and so forth.

Convolutional Neural Networks

Neural networks 700 can be categorized into different types based on their mode of operation. By way of example, a convolutional neural network is one type of neural network that employs or incorporates one or more convolution layers, as opposed to dense or densely connected layers. In particular, densely connected layers learn global patterns in their input feature space. Conversely, convolution layers learn local patterns. By way of example, in the case of images, convolution layers may learn patterns found in small windows or subsets of the inputs. This focus on local patterns or features gives convolutional neural networks two useful properties: (1) the patterns they learn are translation invariant, and (2) they can learn spatial hierarchies of patterns.

With regard to this first property, after learning a certain pattern in one portion or subset of a data set, a convolution layer can recognize the pattern in other portions of the same or different data sets. In contrast, a densely connected network would have to learn the pattern anew if it were present elsewhere (e.g., at a new location). This property makes convolutional neural networks data efficient because they need fewer training samples to learn representations that can then be generalized so as to be identified in other contexts and locations.

Regarding the second property, a first convolution layer can learn small local patterns while a second convolution layer learns larger patterns made of the features of the first layers, and so on. This allows convolutional neural networks to efficiently learn increasingly complex and abstract visual concepts.

With this in mind, a convolutional neural network is capable of learning highly non-linear mappings by interconnecting layers of artificial neurons 704 arranged in many different layers 702 with activation functions that make the layers dependent. It includes one or more convolutional layers, interspersed with one or more sub-sampling layers and non-linear layers, which are typically followed by one or more fully connected layers. Each element of the convolutional neural network receives inputs from a set of features in the previous layer. The convolutional neural network learns concurrently because the neurons in the same feature map have identical weights. These local shared weights reduce the complexity of the network such that when multi-dimensional input data enters the network, the convolutional neural network avoids the complexity of data reconstruction in feature extraction and regression or classification process.

Convolutions operate over 3D tensors, called feature maps, with two spatial axes (height and width) as well as a depth axis (also called the channels axis). The convolution operation extracts patches from its input feature map and applies the same transformation to all of these patches, producing an output feature map. This output feature map is still a 3D tensor: it has a width and a height. Its depth can be arbitrary because the output depth is a parameter of the layer, and the different channels in that depth axis stand for filters. Filters encode specific aspects of the input data.

For instance in an example where a first convolution layer takes a feature map of a given size (28, 28, 1) and outputs a feature map of size (26, 26, 32): it computes 32 filters over its input. Each of these 32 output channels contains a 26×26 grid of values, which is a response map of the filter over the input, indicating the response of that filter pattern at different locations in the input. That is what the term feature map means in this context: every dimension in the depth axis is a feature (or filter), and the 2D tensor output [:, :, n] is the 2D spatial map of the response of this filter over the input.

With the preceding in mind, convolutions are defined by two key parameters: (1) the size of the patches extracted from the inputs, and (2) the depth of the output feature map (i.e., the number of filters computed by the convolution). In typical implementations these start with a depth of 32, continue to a depth of 64, and terminate with a depth of 128 or 256, though certain implementations may vary from this progression.

Figure 40:
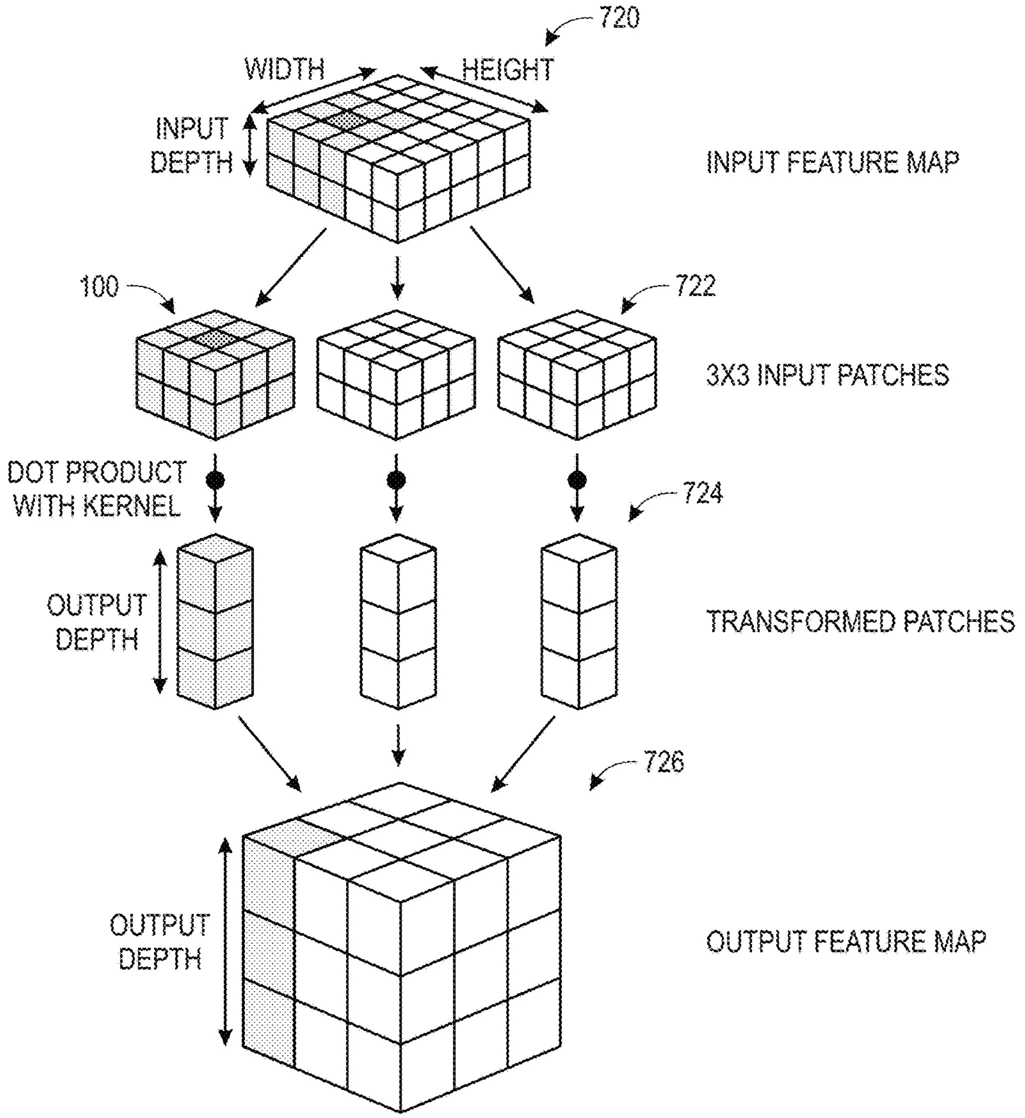
FIG. 40 depicts an example of one implementation of a convolutional neural network, in accordance with aspects of the present disclosure.

Turning to FIG. 40, a visual overview of the convolution process is depicted. As shown in this example, a convolution works by sliding (e.g., incrementally moving) these windows (such as windows of size 3×3 or 5×5) over the 3D input feature map 720, stopping at every location, and extracting the 3D patch 722 of surrounding features (shape (window_height, window_width, input_depth)). Each such 3D patch 722 is then transformed (via a tensor product with the same learned weight matrix, called the convolution kernel) into a 1D vector 724 of shape (output_depth) (i.e., transformed patches). These vectors 724 are then spatially reassembled into a 3D output feature map 726 of shape (height, width, output_depth). Every spatial location in the output feature map 726 corresponds to the same location in the input feature map 720. For instance, with 3×3 windows, the vector output [i, j, :] comes from the 3D patch input [i−1: i+1, j−1:J+1, :].

With the preceding in mind, a convolutional neural network comprises convolution layers which perform the convolution operation between the input values and convolution filters (matrix of weights) that are learned over multiple gradient update iterations during a training process. Where (m, n) is the filter size and W is the matrix of weights, a convolution layer performs a convolution of W with the input X by calculating the dot product $W \cdot x+b$, where x is an instance of X and b is the bias. The step size by which the convolution filters slide across the input is called the stride, and the filter area (m×n) is called the receptive field. A same convolution filter is applied across different positions of the input, which reduces the number of weights learned. It also allows location invariant learning, i.e., if an important pattern exists in the input, the convolution filters learn it no matter where it is in the sequence.

Training a Convolutional Neural Network

As may be understood from the preceding discussion, the training of a convolutional neural network is an important aspect of the network performing a given task of interest. The convolutional neural network is adjusted or trained so that the input data leads to a specific output estimate. The convolutional neural network is adjusted using back propagation based on a comparison of the output estimate and the ground truth until the output estimate progressively matches or approaches the ground truth.

The convolutional neural network is trained by adjusting the weights between the neurons based on the difference (i.e., error, δ) between the ground truth and the actual output. The intermediary step in the training process includes generating a feature vector from the input data using the convolution layers, as described herein. The gradient with respect to the weights in each layer, starting at the output, is calculated. This is referred to as the backward pass or going backwards. The weights in the network are updated using a combination of the negative gradient and previous weights.

In one implementation, the convolutional neural network 150 uses a stochastic gradient update algorithm (such as ADAM) that performs backward propagation of errors by means of gradient descent. The algorithm includes computing the activation of all neurons in the network, yielding an output for the forward pass. The error and the correct weights are then calculated per layer. In one implementation, the convolutional neural network uses a gradient descent optimization to compute the error across all the layers.

In one implementation, the convolutional neural network uses a stochastic gradient descent (SGD) to calculate the cost function. A SGD approximates the gradient with respect to the weights in the loss function by computing it from only one, randomized, data pair. In other implementations, the convolutional neural network uses different loss functions such as Euclidean loss and softmax loss. In a further implementation, an Adam stochastic optimizer is used by the convolutional neural network.

Convolution Layers

The convolution layers of the convolutional neural network serve as feature extractors. In particular, convolution layers act as adaptive feature extractors capable of learning and decomposing the input data into hierarchical features. Convolution operations typically involve a "kernel", applied as a filter on the input data, producing an output data.

The convolution operation includes sliding (e.g., incrementally moving) the kernel over the input data. For each position of the kernel, the overlapping values of the kernel and the input data are multiplied and the results are added. The sum of products is the value of the output data at the point in the input data where the kernel is centered. The resulting different outputs from many kernels are called feature maps.

Once the convolutional layers are trained, they are applied to perform recognition tasks on new inference data. Since the convolutional layers learn from the training data, they avoid explicit feature extraction and implicitly learn from the training data. Convolution layers use convolution filter kernel weights, which are determined and updated as part of the training process. The convolution layers extract different features of the input, which are combined at higher layers. The convolutional neural network uses a various number of convolution layers, each with different convolving parameters such as kernel size, strides, padding, number of feature maps and weights.

Sub-Sampling Layers

Further aspects of implementation of a convolution neural network may involve sub-sampling of layers. In this context, sub-sampling layers reduces the resolution of the features extracted by the convolution layers to make the extracted features or feature maps robust against noise and distortion. In one implementation, sub-sampling layers employs two types of pooling operations, average pooling and max pooling. The pooling operations divide the input into non-overlapping spaces or regions. For average pooling, the average of the values in the region is calculated. For max pooling, the maximum value of the values is selected.

In one implementation, the sub-sampling layers include pooling operations on a set of neurons in the previous layer by mapping its output to only one of the inputs in max pooling and by mapping its output to the average of the input in average pooling. In max pooling, the output of the pooling neuron is the maximum value that resides within the input. In average pooling, the output of the pooling neuron is the average value of the input values that reside with the input neuron set.

Non-Linear Layers

A further aspect of a neural network implementation relevant to the present concepts is the use of non-linear layers. Non-linear layers use different non-linear trigger functions to signal distinct identification of likely features on each hidden layer. Non-linear layers use a variety of specific functions to implement the non-linear triggering, including, but not limited to, the rectified linear units (ReLUs), hyperbolic tangent, absolute of hyperbolic tangent, sigmoid and continuous trigger (non-linear) functions. In one implementation, a ReLU activation implements the function y=max(x, 0) and keeps the input and output sizes of a layer the same. One potential advantage of using ReLU is that the convolutional neural network may be trained many times faster. ReLU is a non-continuous, non-saturating activation function that is linear with respect to the input if the input values are larger than zero and zero otherwise.

In other implementations, the convolutional neural network may use a power unit activation function, which is a continuous, non-saturating function. The power activation function is able to yield x and y-antisymmetric activation if c is odd and y-symmetric activation if c is even. In some implementations, the unit yields a non-rectified linear activation.

In yet other implementations, the convolutional neural network may use a sigmoid unit activation function, which is a continuous, saturating function. The sigmoid unit activation function does not yield negative activation and is only antisymmetric with respect to the y-axis.

Residual Connections

Figure 41:
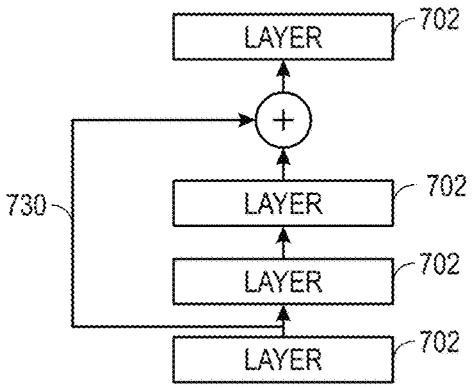
FIG. 41 depicts a residual connection that reinjects prior information downstream via feature-map addition, in accordance with aspects of the present disclosure.

A further feature of convolutional neural networks is the use of residual connections that reinject prior information downstream via feature-map addition, as illustrated in FIG. 41. As shown in this example, a residual connection 730 comprises reinjecting previous representations into the downstream flow of data by adding a past output tensor to a later output tensor, which helps prevent information loss along the data-processing flow. The residual connection 730 comprises making the output of an earlier layer available as input to a later layer, effectively creating a shortcut in a sequential network. Rather than being concatenated to the later activation, the earlier output is summed with the later activation, which assumes that both activations are the same size. If they are of different sizes, a linear transformation to reshape the earlier activation into the target shape can be used. Residual connections tackle two problems that may be present in any large-scale deep-learning model: (1) vanishing gradients, and (2) representational bottlenecks. In general, adding residual connections 730 to any model that has more than ten layers is likely to be beneficial.

Residual Learning and Skip-Connections

Another concept present in convolutional neural networks relevant to the present techniques and approaches is the use of skip connections. The principle behind residual learning is that the residual mapping is easier to be learned than the original mapping. Residual networks stack a number of residual units to alleviate the degradation of training accuracy. Residual blocks make use of special additive skip connections to combat vanishing gradients in deep neural networks. At the beginning of a residual block, the data flow is separated into two streams: (1) the first carries the unchanged input of the block, (2) the second applies weights and non-linearities. At the end of the block, the two streams are merged using an element-wise sum. One advantage of such constructs is to allow the gradient to flow through the network more easily.

With the benefit of such residual networks, deep convolutional neural networks (CNNs) can be easily trained and improved accuracy can be achieved for data classification, object detection, and so forth. Convolutional feed-forward networks connect the output of the $l^{th}$ layer as input to the $(l+1)^{th}$ layer. Residual blocks add a skip-connection that bypasses the non-linear transformations with an identify function. An advantage of residual blocks is that the gradient can flow directly through the identity function from later layers to the earlier layers.

Batch Normalization

An additional aspect related to implementations of convolutional neural networks that may be applicable to the present pathogenicity classification approaches is batch normalization, which is a method for accelerating deep network training by making data standardization an integral part of the network architecture. Batch normalization can adaptively normalize data even as the mean and variance change over time during training and works by internally maintaining an exponential moving average of the batch-wise mean and variance of the data seen during training. One effect of batch normalization is that it helps with gradient propagation, much like residual connections, and thus facilitates the use of deep networks.

Batch normalization can therefore be seen as yet another layer that can be inserted into the model architecture, just like the fully connected or convolutional layer. The batch normalization layer may typically be used after a convolutional or densely connected layer, though it can also be used before a convolutional or densely connected layer.

Batch normalization provides a definition for feed-forwarding the input and computing the gradients with respect to the parameters and its own input via a backward pass. In practice, batch normalization layers are typically inserted after a convolutional or fully connected layer, but before the outputs are fed into an activation function. For convolutional layers, the different elements of the same feature map (i.e. the activations) at different locations are normalized in the same way in order to obey the convolutional property. Thus, all activations in a mini-batch are normalized over all locations, rather than per activation.

1D Convolution

A further technique used in implementations of convolutional neural networks that may be applicable to the present approach relates to the use of 1D convolutions to extract local 1D patches or subsequences from sequences. A 1D convolution approach obtains each output step from a window or patch in the input sequence. 1D convolution layers recognize local patterns in a sequence. Because the same input transformation is performed on every patch, a pattern learned at a certain position in the input sequences can be later recognized at a different position, making 1D convolution layers translation invariant for translations. For instance, a 1D convolution layer processing sequences of bases using convolution windows of size 5 should be able to learn bases or base sequences of length 5 or less, and it should be able to recognize the base motifs in any context in an input sequence. A base-level 1D convolution is thus able to learn about base morphology.

Global Average Pooling

Another aspect of convolutional neural networks that may be useful or utilized in the present contexts relates to global average pooling. In particular, global average pooling can be use used to replace fully connected (FC) layers for classification by taking the spatial average of features in the last layer for scoring. This reduces the training load and bypasses overfitting issues. Global average pooling applies a structural prior to the model and it is equivalent to linear transformation with predefined weights. Global average pooling reduces the number of parameters and eliminates the fully connected layer. Fully connected layers are typically the most parameter and connection intensive layers, and global average pooling provides much lower-cost approach to achieve similar results. The main idea of global average pooling is to generate the average value from each last layer feature map as the confidence factor for scoring, feeding directly into the softmax layer.

Global average pooling may provide certain benefits including, but not limited to: (1) there are no extra parameters in global average pooling layers thus overfitting is avoided at global average pooling layers; (2) since the output of global average pooling is the average of the whole feature map, global average pooling is robust to spatial translations; and (3) because of the huge number of parameters in fully connected layers which usually take over 50% in all the parameters of the whole network, replacing them by global average pooling layers can significantly reduce the size of the model, and this makes global average pooling very useful in model compression.

Global average pooling makes sense, since stronger features in the last layer are expected to have a higher average value. In some implementations, global average pooling can be used as a proxy for the classification score. The feature maps under global average pooling can be interpreted as confidence maps, and force correspondence between the feature maps and the categories. Global average pooling can be particularly effective if the last layer features are at a sufficient abstraction for direct classification; however, global average pooling alone may not be sufficient or suitable if multilevel features should be combined into groups like parts models, which may be more suitably addressed by adding a simple fully connected layer or other classifier after the global average pooling.

IX. Computer System

Figure 42:
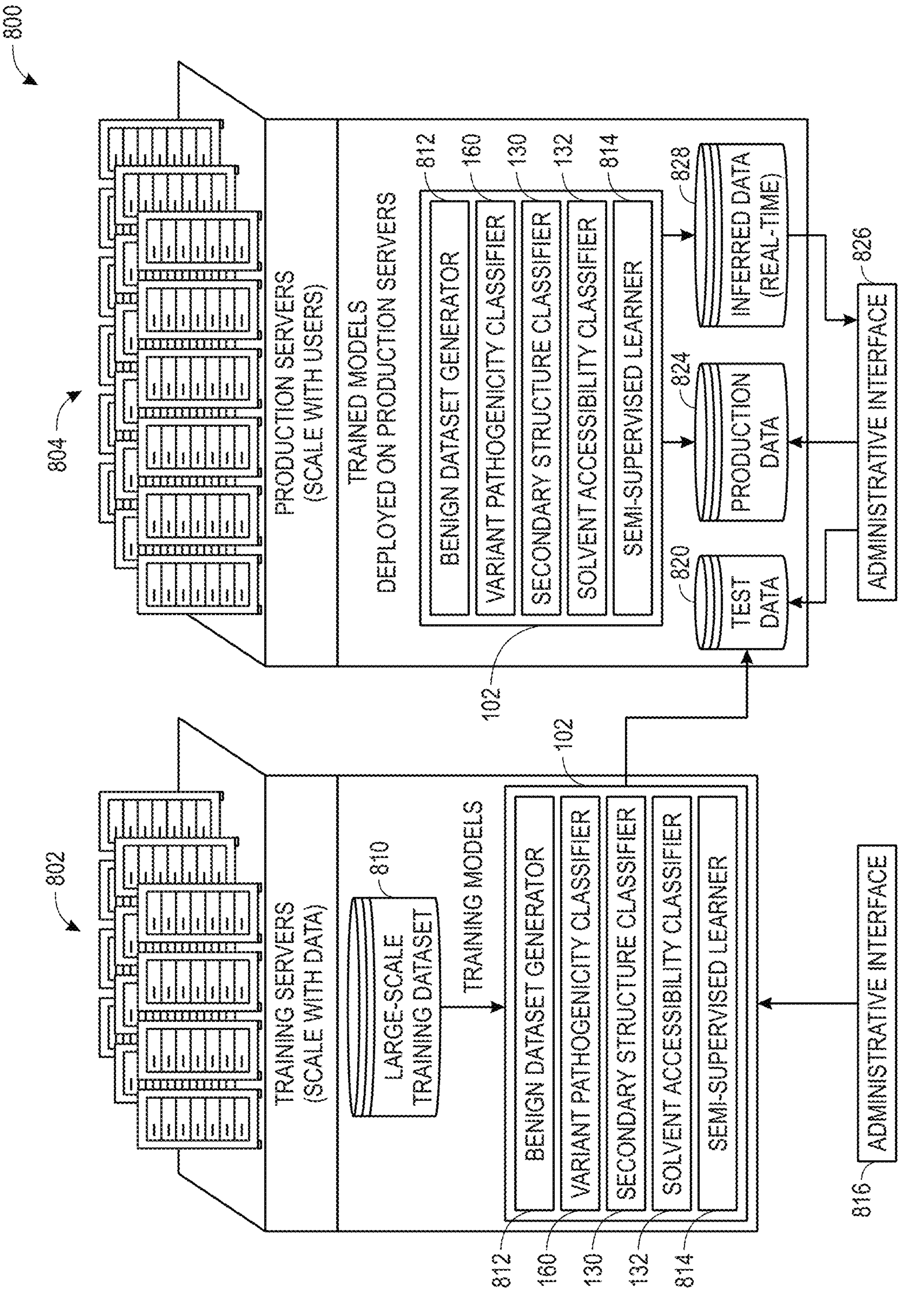
FIG. 42 shows an example computing environment in which the technology disclosed can be operated.

As may be appreciated, the neural network aspects of the present discussion, as well as the analytics and processing performed on the pathogenicity classifier output by the described neural network may be implemented on a computer system or systems. With this in mind, and by way of further context, FIG. 42 shows an example computing environment 800 in which the technology presently disclosed can be operated. The deep convolutional neural network 102 having a pathogenicity classifier 160, secondary structure subnetwork 130, and solvent accessibility subnetwork 132 are trained on one or more training servers 802 (the number of which may be scaled based on the amount of data to be processed or computational load). Other aspects of this approach that may be accessed, generated, and/or utilized by the training servers include, but are not limited to, the training dataset 810 used in the training process, a benign dataset generator 812 as discussed herein, and a semi-supervised learner 814 aspect as discussed herein. An administrative interface 816 may be provided to allow interaction with and/or control over the training server operation. The output of the trained models, as shown in FIG. 42, may include, but is not limited to, a set of test data 820, that may be provided to the production servers 804 for use in the operation and/or testing of the production environment.

With respect to the production environment, and as shown in FIG. 42, the trained deep convolutional neural network 102, having the pathogenicity classifier 160, secondary structure subnetwork 130, and solvent accessibility subnetwork 132 are deployed on one or more production servers 804 that receive input sequences (e.g., production data 824) from requesting clients via a client interface 826. The number of production servers 804 may be scaled based on the number of users, the amount of data to be processed, or, more generally, based on the computational load. The production servers 804 process the input sequences through at least one of the pathogenicity classifier 160, secondary structure subnetwork 130, and solvent accessibility subnetwork 132 to produce outputs (i.e., inferred data 828, which may include pathogenicity score or class) that are transmitted to the clients via the client interface 826. The inferred data 828 may include, but is not limited to, pathogenicity scores or classifiers, selection coefficients, depletion metrics, correction factors or recalibrated metrics, heatmaps, allele frequencies and cumulative allele frequencies, and so forth, as discussed herein.

Figure 43:
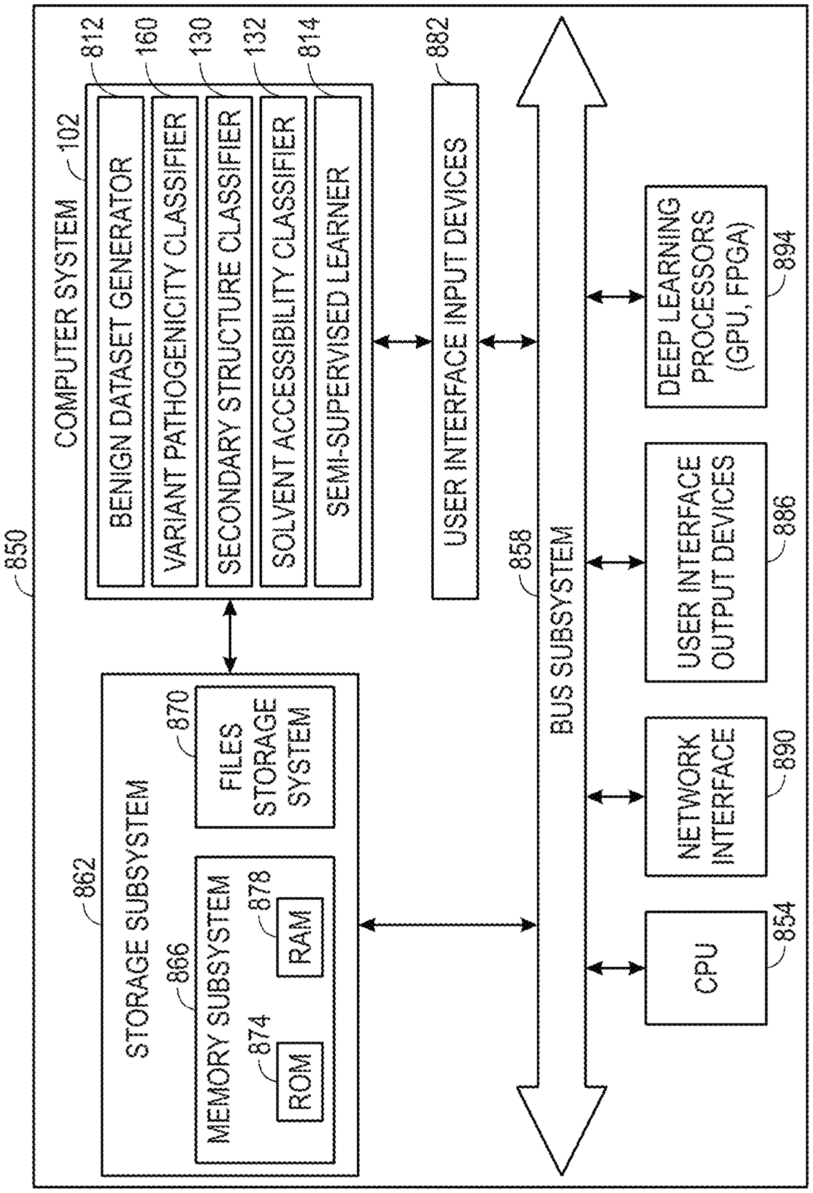
FIG. 43 is a simplified block diagram of a computer system that can be used to implement the technology disclosed.

With respect to the actual hardware architecture that may be employed to run or support the training servers 802, production servers 804, administrative interface 816, and/or client interface(s) 826, such hardware may be physically embodied as one or more computer systems (e.g., servers, workstations, and so forth). Examples of components which may be found in such a computer system 850 are illustrated in FIG. 43, though it should be appreciated that the present example may include components not found in all embodiments of such a system or may not illustrate all components that may be found in such a system. Further, in practice aspects of the present approach may be implemented in part or entirely in a virtual server environment or as part of a cloud platform. However, in such contexts the various virtual server instantiations will still be implemented on a hardware platform as described with respect to FIG. 43, though certain functional aspects described may be implemented at the level of the virtual server instance.

With this in mind FIG. 43 is a simplified block diagram of a computer system 850 that can be used to implement the technology disclosed. Computer system 850 typically includes at least one processor (e.g., CPU) 854 that communicates with a number of peripheral devices via bus subsystem 858. These peripheral devices can include a storage subsystem 862 including, for example, memory devices 866 (e.g., RAM 874 and ROM 878) and a file storage subsystem 870, user interface input devices 882, user interface output devices 886, and a network interface subsystem 890. The input and output devices allow user interaction with computer system 850. Network interface subsystem 890 provides an interface to outside networks, including an interface to corresponding interface devices in other computer systems.

In one implementation in which the computer system 850 is used to implement or train a pathogenicity classifier, the neural networks 102 such as benign dataset generator 812, variant pathogenicity classifier 160, secondary structure classifier 130, solvent accessibility classifier 132, and semi-supervised learner 814 are communicably linked to the storage subsystem 862 and user interface input devices 882.

In the depicted example, and in the context in which the computer system 850 is used to implement or train a neural network as discussed herein, one or more deep learning processors 894 may be present as part of the computer system 850 or otherwise in communication with the computer system 850. In such an embodiment, the deep learning processors can be GPUs or FPGAs and can be hosted by a deep learning cloud platforms such as Google Cloud Platform, Xilinx, and Cirrascale. Examples of deep learning processors include Google's Tensor Processing Unit (TPU), rackmount solutions like GX4 Rackmount Series, GX8 Rackmount Series, NVIDIA DGX-1, Microsoft' Stratix V FPGA, Graphcore's Intelligent Processor Unit (IPU), Qualcomm's Zeroth platform with Snapdragon processors, NVIDIA's Volta, NVIDIA's DRIVE PX, NVIDIA's JETSON TX1/TX2 MODULE, Intel's Nirvana, Movidius VPU, Fujitsu DPI, ARM's DynamicIQ, IBM TrueNorth, and others.

In the context of the computer system 850, the user interface input devices 882 can include a keyboard; pointing devices such as a mouse, trackball, touchpad, or graphics tablet; a scanner; a touch screen incorporated into the display; audio input devices such as voice recognition systems and microphones; and other types of input devices. In general, use of the term "input device" may be construed as encompassing all possible types of devices and ways to input information into computer system 850.

User interface output devices 886 can include a display subsystem, a printer, a fax machine, or non-visual displays such as audio output devices. The display subsystem can include a cathode ray tube (CRT), a flat-panel device such as a liquid crystal display (LCD), a projection device, or some other mechanism for creating a visible image. The display subsystem can also provide a non-visual display such as audio output devices. In general, use of the term "output device" may be construed as encompassing all possible types of devices and ways to output information from computer system 850 to the user or to another machine or computer system.

Storage subsystem 862 stores programming and data constructs that provide the functionality of some or all of the modules and methods described herein. These software modules are generally executed by a processor 854 alone or in combination with other processors 854.

Memory 866 used in the storage subsystem 862 can include a number of memories including a main random access memory (RAM) 878 for storage of instructions and data during program execution and a read only memory (ROM) 874 in which fixed instructions are stored. A file storage subsystem 870 can provide persistent storage for program and data files, and can include a hard disk drive, a floppy disk drive along with associated removable media, a CD-ROM drive, an optical drive, or removable media cartridges. The modules implementing the functionality of certain implementations can be stored by file storage subsystem 870 in the storage subsystem 862, or in other machines accessible by the processor 854.

Bus subsystem 858 provides a mechanism for letting the various components and subsystems of computer system 850 communicate with each other as intended. Although bus subsystem 858 is shown schematically as a single bus, alternative implementations of the bus subsystem 858 can use multiple busses.

The computer system 850 itself can be of varying types including a personal computer, a portable computer, a workstation, a computer terminal, a network computer, a television, a mainframe, a stand-alone server, a server farm, a widely-distributed set of loosely networked computers, or any other data processing system or user device. Due to the ever-changing nature of computers and networks, the description of computer system 850 depicted in FIG. 43 is intended only as a specific example for purposes of illustrating the technology disclosed. Many other configurations of computer system 850 are possible having more or less components than the computer system 850 depicted in FIG. 43.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method for classifying a variant of interest, the method comprising:

executing, on one or more processors of a computer system, stored instructions for classifying the variant of interest, wherein the stored instructions, when executed, cause the one or more processors to perform acts comprising:

generating a pathogenicity score for a variant of interest of a gene using a neural network trained using both human sequence data and non-human primate date sequence data;

comparing the pathogenicity score for the variant of interest to a gene-specific pathogenicity threshold determined for the gene, wherein different genes have different respective pathogenicity thresholds; and classifying the variant of interest as a pathogenic variant in response to the pathogenicity score exceeding the gene-specific pathogenicity threshold determined for the gene.

2. The method of claim 1, wherein the pathogenicity score is based on an extent of purifying selection for the variant of interest represented in the human sequence data and non-human primate date sequence data.

3. The method of claim 1, further comprising:

determining a correlation between mean pathogenicity scores for pathogenic variants and percentiles of pathogenicity scores;

wherein the correlation between the mean pathogenicity scores for pathogenic variants and the percentiles of pathogenicity scores is used to define the gene-specific pathogenic threshold.

4. The method of claim 1, wherein the pathogenicity score is generated based on an amino acid sequence processed by the neural network, wherein the neural network is trained to generate the pathogenicity score from amino acid sequences.

5. The method of claim 4, wherein a central amino acid of the amino acid sequence corresponds to the variant of interest.

6. The method of claim 1, wherein the gene-specific pathogenic threshold is in the range defined by and including the $51^{st}$ percentile to the $99^{th}$ percentile.

7. The method of claim 1, wherein the gene-specific pathogenic threshold is in the range defined by and including the $75^{th}$ percentile to the $99^{th}$ percentile.

8. The method of claim 1, wherein the stored instructions, when executed, cause the one or more processors to perform further acts comprising:

comparing the pathogenicity score for the variant of interest to a gene-specific benign threshold determined for the gene, wherein different genes have different respective benign thresholds; and in response to the pathogenicity score being less than the gene-specific benign threshold, classifying the variant of interest as benign.

9. The method of claim 8, further comprising:

determining a correlation between mean pathogenicity scores for benign variants and percentiles of pathogenicity scores;

wherein the correlation between the mean pathogenicity scores for benign variants and the percentiles of pathogenicity scores is used to define the gene-specific benign threshold.

10. The method of claim 8, wherein the gene-specific benign threshold is in the range defined by and including the $1^{st}$ percentile to the $49^{th}$ percentile.

11. The method of claim 8, wherein the gene-specific benign threshold is in the range defined by and including the $1^{st}$ percentile to the $25^{th}$ percentile.

12. The method of claim 1, further comprising:

determining the gene-specific pathogenicity threshold for the gene based on a correlation between mean pathogenicity scores for pathogenic variants of the gene and pathogenicity scores at the $51^{st}$ percentile or greater of missense variants of the gene.

13. A non-transitory computer-readable medium storing processor- executable instructions that, when executed by one or more processors, cause the one or more processors to perform steps comprising:

processing a variant of interest for a gene using a pathogenicity scoring neural network to generate a pathogenicity score for the variant of interest, wherein the pathogenicity scoring neural network is trained using both human sequence data and non-human primate date sequence data;

comparing the pathogenicity score for the variant of interest to a pathogenicity threshold specific to the gene and a benign threshold specific to the gene, wherein different genes have different respective pathogenicity thresholds and benign thresholds; and classifying the variant of interest as pathogenic, benign, or neither pathogenic or benign based on the comparison of the pathogenicity score to the pathogenicity threshold specific to the gene and the comparison of the pathogenicity score to the benign threshold specific to the gene.

14. The non-transitory computer-readable medium of claim 13, wherein the variant is classified as pathogenic in response to the pathogenicity score exceeding the pathogenicity threshold specific to the gene.

15. The non-transitory computer-readable medium of claim 13, wherein the variant is classified as benign in response to the pathogenicity score being below the benign threshold specific to the gene.

16. The non-transitory computer-readable medium of claim 13, wherein the variant is classified as neither pathogenic nor benign in response to the pathogenicity score being between the benign threshold specific to the gene and the pathogenic threshold specific to the gene.

17. The non-transitory computer-readable medium of claim 13, wherein comparing the pathogenicity score for the variant of interest to the pathogenicity threshold specific to the gene and the benign threshold specific to the gene comprises comparing the pathogenicity score for the variant of interest to the pathogenicity threshold prior to the benign threshold, wherein comparison to the benign threshold is contingent upon the outcome of the comparison to the first pathogenicity threshold.

18. The non-transitory computer-readable medium of claim 13, wherein comparing the pathogenicity score for the variant of interest to the pathogenicity threshold specific to the gene and the benign threshold specific to the gene comprises comparing the pathogenicity score for the variant of interest to the pathogenicity threshold and to the benign threshold in parallel.

19. A variant classification system, comprising:

one or more memory structures encoding processor-executable instructions;

one or more processors in communication with the one or more memory structures, wherein the one or more processors execute the instructions to perform operations comprising:

generating a pathogenicity score for a variant of interest of a gene using a neural network trained using both human sequence data and non-human primate date sequence data;

comparing the pathogenicity score for the variant of interest to a pathogenicity threshold specific to the gene and a benign threshold specific to the gene, wherein different genes have different respective pathogenicity thresholds and benign thresholds; and classifying the variant of interest as pathogenic, benign, or neither pathogenic or benign based on the comparison of the pathogenicity score to the pathogenicity threshold specific to the gene and the comparison of the pathogenicity score to the benign threshold specific to the gene.

20. The variant classification system of claim 19, wherein the variant of interest is classified as pathogenic in response to the pathogenicity score exceeding the gene specific pathogenicity threshold specific to the gene.

21. The variant classification system of claim 19, wherein the variant of interest is classified as benign in response to the pathogenicity score being below the benign threshold specific to the gene.

* * * * *